US005706212A

United States Patent [19]

Thompson et al.

[11] Patent Number: 5,706,212

[45] Date of Patent: Jan. 6, 1998

[54] INFRARED ELLIPSOMETER/ POLARIMETER SYSTEM, METHOD OF CALIBRATION, AND USE THEREOF

[75] Inventors: Daniel W. Thompson; Blaine D. Johs, both of Lincoln, Nebr.

[73] Assignees: Board of Regents of University of Nebraska; J.A. Woollam Co. Inc., both of Lincoln, Nebr.

[21] Appl. No.: 618,820

[22] Filed: Mar. 20, 1996

[51] Int. Cl.$^6$ .............................. G01N 21/21; G01J 3/447

[52] U.S. Cl. .......................... 364/525; 356/367; 356/368; 356/382; 250/339.09; 250/339.12; 250/345

[58] Field of Search ..................................... 356/369, 367, 356/351, 357, 368, 381, 382, 73, 364, 327, 243, 365; 250/343, 225, 345, 339.12, 339.09, 338.1; 359/159, 834, 837, 637

[56] References Cited

U.S. PATENT DOCUMENTS

| | | | |
|---|---|---|---|
| 3,594,058 | 7/1971 | Wilmanss . | |
| 3,638,004 | 1/1972 | Sloane et al. | 235/156 |
| 3,700,912 | 10/1972 | Glass et al. | 307/88.3 |
| 3,873,207 | 3/1975 | Bryngdahl | 356/106 R |
| 3,880,524 | 4/1975 | Dill et al. | 356/118 |
| 3,927,945 | 12/1975 | Bates | 356/108 |
| 4,053,232 | 10/1977 | Dill et al. | 356/118 |
| 4,076,423 | 2/1978 | Bates | 356/364 |
| 4,298,283 | 11/1981 | Makosch et al. | 356/351 |
| 4,373,816 | 2/1983 | Laib | 356/375 |
| 4,508,832 | 4/1985 | Carter et al. . | |
| 4,518,231 | 5/1985 | Muchel et al. | 350/516 |
| 4,647,207 | 3/1987 | Björk et al. . | |
| 4,686,631 | 8/1987 | Ruud | 364/508 |
| 4,790,659 | 12/1988 | Erman et al. . | |
| 5,045,701 | 9/1991 | Goldstein et al. | 250/339 |
| 5,191,391 | 3/1993 | Tsai | 356/351 |
| 5,247,176 | 9/1993 | Goldstein | 250/338.1 |
| 5,293,216 | 3/1994 | Maslehi . | |
| 5,333,052 | 7/1994 | Finarov | 356/369 |
| 5,347,387 | 9/1994 | Rice | 359/152 |
| 5,354,575 | 10/1994 | Dgenais et al. | 427/10 |
| 5,483,161 | 1/1996 | Deeter et al. | 324/244.1 |
| 5,504,582 | 4/1996 | Johs et al. | 356/369 |
| 5,519,218 | 5/1996 | Chang | 250/339.07 |
| 5,521,706 | 5/1996 | Green et al. | 356/369 |
| 5,539,668 | 7/1996 | Tokuda et al. | 364/525 |
| 5,557,544 | 9/1996 | Simon et al. | 364/525 |
| 5,563,807 | 10/1996 | Kashiwagi et al. | 364/525 |
| 5,581,350 | 12/1996 | Chen et al. | 356/369 |

FOREIGN PATENT DOCUMENTS

| | | | |
|---|---|---|---|
| 701940 | 3/1931 | France . | |
| 57-49822 | 3/1982 | Japan | G01J 1/42 |
| 907679 | 10/1962 | United Kingdom . | |
| WO83/00257 | 7/1981 | WIPO | G01J 3/38 |

OTHER PUBLICATIONS

A critical evaluation of Rhomb-Type Quarterwave Retarders, Bennett, "Applied Optics" vol. 9,No. 9, Sep. 1970.

Analysis of a novel ellipsometric technique with special advantages for infrared, Stobie et al., "Applied Optics", 14,999, (1975).

Regression Calibration Method for Rotating Element Ellipsometers, Johs, "Thin Solid Films", 234 (1993).

(List continued on next page.)

*Primary Examiner*—James P. Trammell
*Assistant Examiner*—Cuong H. Nguyen
*Attorney, Agent, or Firm*—James D. Welch

[57] ABSTRACT

A sample system investigation system, such as an ellipsometer or polarimeter system, for use in investigating sample systems with electromagnetic wavelengths in the infrared range, and a calibration method for compensating nonidealities in multi-dimensional system rotated and non-rotated component representing matricies, are disclosed. An essentially achromatic compensator of dual-rhomb construction, which introduces a (3*LAMBDA/4) phase shift, but essentially no deviation in the direction of propagation of a polarized beam of electromagnetic wavelengths caused to pass therethrough, even when said compensator is caused to continuously rotate, is also disclosed.

29 Claims, 5 Drawing Sheets

OTHER PUBLICATIONS

J. M. Bennett, A Critical Evaluation of Rhomb–Type Quarterwave Retarders, Applied Optics vol. 9, No. 9, pp. 2125, 2128–2129, Sep.1970.

Stoyan H. Russev, "Correction for nonlinearity and polarization–dependent sensitivity in the detection system of rotating analyzer ellipsometers." Applied Optics, vol. 28, No. 8, pp. 1504–1507, Apr. 15, 1989.

Thompson, et al. "Measurement of polarized light interactions via the Mueller matrix", Applied Optics, vol. 19, No. 8, pp. 1323–1332, Apr. 15, 1980.

Aspnes and Studna, "High Precision Scanning Ellipsometer", Applied Optics, vol. 14, No. 1, pp. 220–228, Jan. 1975.

Stobie, et al. "Analysis of a novel ellipsometric technique with special advantages for infrared spectroscopy," Journal of the Optical Society of America, vol. 65, No. 1, pp. 25–28, Jan. 1975.

Hamilton, et al. "Rudolph AutoEL II Ellipsometer Users Manual", Micro Fabrication Facility of U.C. Davis.

Jones, "Ellipsometry: Jones Matrices", D. J. De Smet, 1995.

INFRARED ELLIPSOMETER/ POLARIMETER SYSTEM, METHOD OF CALIBRATION, AND USE THEREOF

TECHNICAL FIELD

The present invention is a Sample System Investigation System such as an Ellipsometer or Polarimeter System. More particularly the present invention is a Sample System Investigation System which is designed for use primarily in the Infrared Range of Wavelengths, preferably comprising an essentially Achromatic Dual-Rhomb Shaped Rotatable Compensator that is designed to operate at Infrared Wavelengths without introducing significant Deviation or Displacement in the Direction of Propagation of a Polarized Beam of Electromagnetic Wavelengths caused to pass therethrough. The present invention also comprises a Regression Method of Calibration for Evaluating Non-Ideality Compensating Calibration Parameters in Mathematical Representations of both Rotated and Non-Rotated System Components, which Nonidealities become particularly significant in the Infrared Wavelength range.

BACKGROUND

The use of ellipsometer systems to investigate the physical and optical properties of sample systems is well established. Generally, ellipsometry and polarimetry are practices in which a beam of electromagnetic wavelength(s), in a known state of polarization, is caused to interact with a sample system. A change in the state of polarization of said beam of electromagnetic wavelength(s) resulting from said interaction with said sample system is measured and is identifying of sample system physical and optical properties. Typically, data is experimentally obtained by measuring the change in intensity of a polarized beam of electromagnetic wavelength(s) which has interacted with a sample system. Next, a sample system model is proposed and calculations based upon Snell's law and known relationships between angles of incidence and reflection and phase change upon reflection utilized to calculate what change in polarization state would be expected to result if a polarized beam of electromagnetic wavelength(s) were caused to interact therewith. A Square error reducing regression procedure, (eg. Levenberg-Marquardt), is then typically practiced to determine if the proposed model is consistent with said measured data. Said regression procedure can involve varying values of physical and optical parameters in the proposed model until a "good-fit", based upon a low square error, is achieved.

Most ellipsometry and polarimetry to date has been practiced utilizing wavelengths shorter than infrared, (eg. shorter than two (2) to fourteen (14) microns), and has been concerned with obtaining information which allows determining the thickness and complex refractive index, (ie. complex dielectric constant), of thin films, or systems thereof, present at the surface of a sample system.

It is to be appreciated that use of infrared wavelengths allows investigation of chemical bonding, atomic level vibrational modes, and resistivity, (ie. present carrier concentrations), of or in sample system materials. That is, the information provided by practice of ellipsometry using the infrared range of wavelengths, expands the range of what sample system properties can be investigated beyond that of, for instance, thin film system thicknesses and refractive indicies.

With an eye to the present invention a search for relevant references in the area has provided an article by Bennett, titled "A Critical Evaluation of Rhomb-Type Quarter Wavelength Retarders", Applied Optics, Vol. 9, No. 9, September, 1970. This article is a provides an overview of Rhomb-Type Compensators, of the type utilized in the present invention system.

Another article, by Stobie et al., titled "Analysis of a Novel Ellipsometric Technique with Special Advantage for Infrared Spectroscopy", Appl. Opt. 14, 999, (1975). Briefly the technique disclosed involves use of a Rotating Analyzer or Rotating Polarizer and describes sensitivity calculations which serve to provide measurement of a signal phase angle.

A German Patent No. 1572 19 to Roeseler is disclosed as it describes an ellipsometer system for application in the IR range of wavelengths.

Another Patent identified is that to Goldstein, U.S. Pat. No. 5,247,176, titled "Infrared Laser Polarimetry". A Polarimeter System for measuring the Mueller Matrix of a sample system is described. An infrared laser source for projecting an infrared beam of a preselected wavelength, (eg. 3–14 microns), along an optical axis in which at least one polarizing element is positioned and in which are positioned first and second rotatable optical retarders, is disclosed. In use the second retarder is rotated at least five times faster than the first.

Additional Patents related to the area of Ellipsometry were identified and are mentioned herein because they include the term "infrared" therein. Said Patents, while not felt to be particulary relevant to the present invention, are U.S. Pat. No. 4,647,207 to Bjork et al.; No. 4,508,832 to Carter et al., No. 3,594,085 to Wilmanns; No. 5,293,216 to Moslehi; and No. 4,790,659 to Erman et al.

An Article by Blaine Johs, titled "Regression Calibration Method For Rotating Element Ellipsometers", This Solid Films, 234, (1993), is also disclosed as it describes a regression based approach to calibrating ellipsometer system Analyzer and Polarizer Angle Offsets and Electronic Circuitry Attenuation Factors. This reference, however, does not describe application of a regression based approach to evaluating Calibration Parameters in both rotated and non-rotated ellipsometer system components, nor does it address the evaluation of the numerous Calibration Parameters required in ellipsometer systems operated in the Infrared range of wavelengths.

A book titled "Numerical Recipes in C", Cambridge University Press, 1988 is disclosed as it describes the "Levenburg-Marquard" error reducing algorithm often utilized in mathematical regression procedures.

Finally, a book by Arnulf Roeseler, titled "Infrared Spectroscopic Ellipsometry", which was published by Akademe-Verlag, 1990, is disclosed as it focuses on the practice of Ellipsometry in the infrared range of wavelengths.

It should be appreciated that Ellipsometer Systems and Methods for application thereof in the investigation of sample system material attributes such as chemical bonding, atomic level vibrational modes, and resistivity, (ie. present carrier concentrations), of or in said sample system materials, provide utility.

A need exists for an improved ellipsometer system which can be applied to accurately investigate sample systems utilizing electromagnetic beams comprised of infrared wavelength(s).

DISCLOSURE OF THE INVENTION

The Preferred Embodiment of the present invention has two focal points, said focal points being:

1. The use of a Compensator means of a "Dual-Rhomb" type in which "P" and "S" Cartesian Coordinate Basis Vector Components of a Beam of Polarized Electromagnetic Wavelengths caused to travel therethrough are subjected to a relative retardation of, in the preferred embodiment, (3*LAMBDA/4) therebetween, via a sequence of four (4) (3*LAMBDA/16) phase shifts effected by internal reflections. A significant feature of said present invention Compensator means is that it does not introduce any significant Deviation or Displacement in the Propagation Direction of a Polarized Electromagnetic Beam caused to pass therethrough. As a result said present invention Compensator means can be utilized in a Rotating Mode without introducing any significant Variable Change in said Direction of Propagation; and
2. The use of a Mathematical Regression based Calibration Procedure, which Mathematical Regression based calibration Procedure can be described as serving to evaluate present invention System Component Non-Ideality Compensating Calibration Parameters present in Mathematical. Representations of IR Ellipsometer System Component, (or "Lumped" Combinations of System Components), Characterizing Transfer Function Matrix Element Determining Equations, which Calibration Parameters serve to compensate said IR Ellipsometer System Characterizing Transfer Function Matrices for said Non-Idealities of IR Ellipsometer System Components.

It is generally to be understood that while the Type, (ie. Dual-Rhomb), of preferred embodiment Compensator means utilized in the present invention is not per se. new and novel, the specific Design thereof utilized is original, and the Inventor knows of no prior use of such a Compensator means in an Ellipsometer System, particularly where operated in the Infrared Electromagnetic Wavelength Range, (eg. two (2) microns to fourteen (14) microns Wavelength), and where a phase shift of (3*LAMBDA/4), rather than a direct (LAMBDA/4), is introduced between quadrature components of a Polarized Electromagnetic Beam thereby to provide a relative (−LAMBDA/4) phase shift between said quadrature components.

It is also generally pointed out that the Method of the present invention Calibration Procedure could theoretically be applied to Ellipsometer Systems operating outside the Infrared Electromagnetic Wavelength Range. The only reason it probably would not be so applied is that the effects, (eg. System Component Non-idealities), for which the present invention Calibration Procedure compensates, are typically not significant outside the Infrared Wavelength Range.

COMPENSATOR

The preferred embodiment of the present invention Compensator means is a Dual-Rhomb essentially Achromatic System, which does not introduce significant Deviation or Displacement into a Beam of Polarized Electromagnetic Wavelengths even when caused to rotate. To date, the preferred embodiment of the present invention Compensator been specially fabricated from two abutted contact Three-Dimensional Parallelogram shaped elements made of Zinc-Selenide or Zinc-Sulfide, said abutted contact being between short length sides of the Three-Dimensional Parallelogram shaped elements. (Note that any material with an Index of Refraction greater than approximately one-and-eight-tenths (1.8), including, silver-chloride, diamond, cadnium-sulfide, titanium-oxide, amorphous selenium, silicon, germanium irtran-2(™), irtran-4(™), irtran-6(™), KRS-5 and KRS-6 (™) etc. can possibly be utilized. Irtran is a trademark of Eastman Kodak Co.). A Polarized Electromagnetic Beam traveling therethrough is caused to encounter four (4) internal reflections, at each of which a phase shift between quadrature (eg. "P" and "S"), components of said Polarized Electromagnetic Beam occurs, the sum of which four (4) phase shifts is, in the Compensator means utilized, (3*LAMBDA/4), where LAMBDA is the IR Wavelength being utilized. That is, each reflection provides a (3*LAMBDA/16) phase shift. It should be understood that the present invention Compensator means provides an effective (−LAMBDA/4) phase shift between quadrature components of a Polarized Electromagnetic Beam by actually effecting a (3*LAMBDA/4) phase shift therebetween. This approach to providing an effective quarter wavelength magnitude phase shift between said quadrature components was adopted because the Angle Of Incidence (AOI) at which an internal reflection in a Dual-Rhomb structure occurs must be larger if a direct (LAMBDA/4) phase shift is desired. A larger (AOI) means an effectively physically longer Compensator means. That is, a Dual-Rhomb shaped Compensator means which provides a (3*LAMBDA/4) phase shift can be of a shorter length dimension than a similar Dual-Rhomb Compensator means which provides a phase shift of (LAMBDA/4). Shorter overall length of a Dual-Rhomb Compensator means can be an important consideration as space in an IR Ellipsometer System can become cramped. The shape and design of the present invention Dual-Rhomb shaped Compensator means will be better understood by reference to the Detailed Description Section of this Disclosure, in conjunction with the Drawings.

It is also disclosed that alternative Compensators which provide relative retardance between quadrature components in a Polarized Beam of Electromagetic Waves can be utilized in a Sample System Investigation System and the present invention Calibration Procedure, which is described directly, practiced. Alternative Compensators include those which have optical axes parallel, as well as perpendicular (Berek-type), to the surface thereof, said Compensators allowing the setting of retardance provided thereby by rotation and by tilting, respectively. As well, Compensators which effect the setting of retardance provided thereby by application of Electric or Magnetic Fields (eg. Kerr, Pockles, Liquid Crystal, Voight and Coton-Mouton), or by sliding, (eg. wedge shaped Babinet/Soleil type Variable Compensators), might be utilized in a Sample System Investigating System and be within the scope of the present invention Calibration Procedure. The general requirement being, however, that whatever type of Compensator is utilized, it be essentially achromatic and not introduce significant Deviation or Displacement in the Propagation Direction of a Polarized Electromagnetic Beam caused to pass therethrough in use. A book titled, "ELLIPSOMETRY AND POLARIZED LIGHT", by Azzam & Bashara, North-Holland, 1977, is incorporated by reference herein as a source of additional description of alternative Compensators.

CALIBRATION PROCEDURE

The present invention Calibration Procedure assumes the presence of a Sample System investigating System, (typically exemplified as an Infra-Red (IR) Ellipsometer System in what follows), comprised of the following Components:

1. A Continuous Spectral Source of IR Wavelength radiation, (eg. a Michelson FTIR Source), (LS);

2. A Polarizer means, (3.-4.) Compensator means, (C), (see infra);

(4.-3.) A Removable Sample System (SS);

5. An Analyzer means, (A); and

6. A Detector System, (DET).

(Note that Compensator means can be present prior to, and/or after a Sample System in the Optical Electromagnetic Beam Path. When two (2) Compensator means are present they are referred to as First and Second Compensator means.)

Each of the identified IR Ellipsometer System Components has associated therewith a Transfer Function which can be Mathematically Represented, (ie. the IR System Component can be Characterized), by a "Shell Form Matrix", Calibration Parameters in Equations which determine Elements of which "Shell Form Matrix" must be Evaluated to "Calibrate" said "Shell Form Matrix" and make it directly representative of a specific IR Ellipsometer System Component. Once said "Shell Form Matrix" Element determining Calibration Parameters are Evaluated, (in simultaneous combination with Rotation Matrices Rotation Angles), the effect of Matrix Transfer Function Modeled IR Ellipsometer System Components upon the Polarization State of an Electromagnetic Beam of wavelengths which is caused to pass therethrough can be calculated by using said "Calibrated" IR Ellipsometer System Characterizing Matrices in a Matrix Multiplication procedure.

It will be described supra that several approaches to Calibration involving setting Azimuthal Rotation Angles of two (2) Ellipsometer or Polarimeter System Components are possible. Primary examples are Rotated Analyzer Means-Rotated Polarizer means (RARP); Rotated Polarizer Means-Rotated Compensator means (RPRC); and Rotated Compensator Means-Rotated Compensator means (RCRC). The later assumes that Compensator means are present on both sides of a Sample System. It is noted that an additional approach, (ie. RARC), which is similar to the (RPRC) case, can be practiced wherein an Analyzer Means and a Compensator Means are Rotated.

GENERALIZED ELLIPSOMETER OR POLARIMETER SYSTEM

It is instructive to first consider the Overall Transfer Function of a Generalized Representation of a Sample System Investigating System, (eg. an IR Ellipsometer or Polarimeter System), comprising two (2) Rotatable Components, in terms of an Intensity Equation:

$$I(\Theta a,\Theta b)=A*R(\Theta b)*Mb(-\Theta b)*R(-\Theta bs)*Ms*R(\Theta as)*R(\Theta a)*Ma*R(-\Theta a)*S; \quad \text{EQ. 1}$$

where I(θa,θb) is an Intensity signal and where (Θa) and (Θb) are the Azimuthal offset angles of two (2) Stationary Components, (eg. Source and Detector); and where (Θas) and (Θbs) are the Azimuthal offset angles of two (2) Rotatable Components, (eg. Polarizer means, Compensator means and/or Analyzer means); and where (A) represents the polarization-dependent intensity response of a Detector system to a Source Stokes Vector (S); and where (Ma) and (Mb) are the Mueller Matrix representations of said Two (2) Rotatable Components; and (Ms) is a Mueller Matrix representation of a Sample System under investigation.

Continuing, a Rotation Matrix, which serves to rotate a signal Azimuthal Angle through Θ Degrees, is generally represented by:

$$R(\theta)=\begin{bmatrix}1 & 0 & 0 & 0\\ 0 & \cos(2\cdot\theta) & \sin(2\cdot\theta) & 0\\ 0 & -\sin(2\cdot\theta) & \cos(2\cdot\theta) & 0\\ 0 & 0 & 0 & 1\end{bmatrix} \quad \text{EQ.2}$$

Next, a Generalized Ellipsometer or Polarimeter System is represented by a sequence of Matrices as follows:

$$I(\theta_a,\theta_b)=A_0\begin{bmatrix}I\\ A_1\\ A_2\\ A_3\end{bmatrix}^T\begin{bmatrix}1 & 0 & 0 & 0\\ 0 & \cos(2\cdot\theta_b) & \sin(2\cdot\theta_b) & 0\\ 0 & -\sin(2\cdot\theta_b) & \cos(2\cdot\theta_b) & 0\\ 0 & 0 & 0 & 1\end{bmatrix}\cdot \quad \text{EQ.3}$$

$$\begin{bmatrix}M_{b11} & M_{b12} & M_{b13} & M_{b14}\\ M_{b21} & M_{b22} & M_{b23} & M_{b24}\\ M_{b31} & M_{b32} & M_{b33} & M_{b34}\\ M_{b41} & M_{b42} & M_{b43} & M_{b44}\end{bmatrix}\cdot\begin{bmatrix}1 & 0 & 0 & 0\\ 0 & \cos(2\cdot\theta_b) & -\sin(2\cdot\theta_b) & 0\\ 0 & \sin(2\cdot\theta_b) & \cos(2\cdot\theta_b) & 0\\ 0 & 0 & 0 & 1\end{bmatrix}\ldots$$

$$\begin{bmatrix}1 & 0 & 0 & 0\\ 0 & \cos(2\cdot\theta_{bs}) & -\sin(2\cdot\theta_{bs}) & 0\\ 0 & \sin(2\cdot\theta_{bs}) & \cos(2\cdot\theta_{bs}) & 0\\ 0 & 0 & 0 & 1\end{bmatrix}\cdot\begin{bmatrix}M_{s11} & M_{s12} & M_{s13} & M_{s14}\\ M_{s21} & M_{s22} & M_{s23} & M_{24}\\ M_{s31} & M_{s32} & M_{s33} & M_{s34}\\ M_{s41} & M_{s42} & M_{s43} & M_{s44}\end{bmatrix}\cdot$$

$$\begin{bmatrix}1 & 0 & 0 & 0\\ 0 & \cos(2\cdot\theta_{as}) & \sin(2\cdot\theta_{as}) & 0\\ 0 & -\sin(2\cdot\theta_{as}) & \cos(2\cdot\theta_{as}) & 0\\ 0 & 0 & 0 & 1\end{bmatrix}\ldots$$

$$\begin{bmatrix}1 & 0 & 0 & 0\\ 0 & \cos(2\cdot\theta_a) & \sin(2\cdot\theta_a) & 0\\ 0 & -\sin(2\cdot\theta_a) & \cos(2\cdot\theta_a) & 0\\ 0 & 0 & 0 & 1\end{bmatrix}\cdot\begin{bmatrix}M_{a11} & M_{a12} & M_{a13} & M_{a14}\\ M_{a21} & M_{a22} & M_{a23} & M_{a24}\\ M_{a31} & M_{a32} & M_{a33} & M_{a34}\\ M_{a41} & M_{a42} & M_{a43} & M_{a44}\end{bmatrix}\cdot$$

$$\begin{bmatrix}1 & 0 & 0 & 0\\ 0 & \cos(2\cdot\theta_a) & -\sin(2\cdot\theta_a) & 0\\ 0 & \sin(2\cdot\theta_a) & \cos(2\cdot\theta_a) & 0\\ 0 & 0 & 0 & 1\end{bmatrix}\cdot\begin{bmatrix}1\\ S_1\\ S_2\\ S_3\end{bmatrix}\cdot S_0$$

where (Mb_) and (Ma_) Matrix Elements are descriptive of Rotated Components, and where (Ms_) Matrix Elements are descriptive of a Stationary Sample System or "Lumped" "Sample System and Compensator means", for instance.

It can be shown that carrying out the indicated Matrix multiplication provides an expression:

$$\begin{aligned}I(\Theta a,\Theta b) = {} & a00 + a01*COS(2\Theta a) + a02*SIN(2\Theta a) + \quad \text{EQ. 4}\\ & a03*COS(4\Theta a) + a04*SIN(4\Theta a) + a10*COS(2\Theta b) +\\ & a11*COS(2\Theta b)*COS(2\Theta a) + a12*COS(2\Theta b)*SIN(2\Theta a) +\\ & a13*COS(2\Theta b)*COS(4\Theta a) + a14*COS(2\Theta b)*SIN(4\Theta a) +\\ & a20*SIN(2\Theta b) + a21*SIN(2\theta b)*COS(2\Theta a) +\\ & a22*SIN(2\Theta b)*SIN(2\Theta a) + a23*SIN(2\Theta b)*COS(4\Theta a) +\\ & a24*SIN(2\Theta b)*SIN(4\Theta a) + a30*COS(4\Theta b) +\\ & a31*COS(4\Theta b)*COS(2\Theta a) + a32*COS(4\Theta b)*Sin(2\Theta a) +\\ & a33*COS(4\Theta b)*COS(4\Theta a) + a34*COS(4\Theta b)*SIN(4\Theta a) +\\ & a40*SIN(4\Theta b) + a41*SIN(4\Theta b)*COS(2\Theta a) +\\ & a42*SIN(4\Theta b)*SIN(2\Theta a) + a43*SIN(4\Theta b)*COS(4\Theta a) +\\ & a44*SIN(4\Theta b)*SIN(4\Theta a).\end{aligned}$$

which mathematically can be generally expressed in terms of a Double Fourier Series with Basis Functions φ0, φ1, φ2, φ3, and 100 4;

$$zI(\theta_a,\theta_b) = \sum_m \sum_n a_{mn} \cdot \phi_m(\theta_b) \cdot \phi_n(\theta_a) \quad \text{EQ. 5}$$

where $m = 0 \ldots 4$ and $n = 0 \ldots 4$ where:

$$\phi0(\Theta) = 1; \quad \text{EQS. 6}$$
$$\phi1(\Theta) = COS(2\Theta);$$
$$\phi2(\Theta) = SIN(2\Theta);$$
$$\phi3(\Theta) = COS(4\Theta);$$
$$\phi4(\Theta) = SIN(4\Theta);$$

It is to be noted that each Double Fourier Series Coefficient (a00, a01, a02, a03, a04, a10, a11, a12, a13, a14, a20, a21, a22, a23, a24, a30, a31, a32, a33, a34, a40, a41, a42, a43, a44), in the above Intensity Equation is a Function of Calibration Parameters present in Mathematical Representations, (eg. "Shell Form Matrices"), of IR Ellipsometer System Components. (Note, to assure full disclosure, Print-Outs of the actual Functional Relationships between Calibration Parameters and Double Fourier Series Coefficients for various approaches to Calibration, (eg. where two (2) Rotated Components are selected to be the Rotated Analyzer and Rotated Polarizer (RARP); the Rotated Polarizer and Rotated Compensator (RPRC); or the Rotated Compensator and the Rotated Compensator (RCRC)), are specifically provided supra herein).

It is convenient to note that Double Fourier Series Coefficients of the above Intensity Equation can be expressed as elements in a Matrix:

TABLE 1

| | 1 | COS(2Θa) | SIN(2Θa) | COS(4Θa) | SIN(4Θa) |
|---|---|---|---|---|---|
| 1 | a00 | a01 | a02 | a03 | a04 |
| COS(2Θb) | a10 | a11 | a12 | a13 | a14 |
| SIN(2Θb) | a20 | a21 | a22 | a23 | a24 |
| COS(4Θb) | a30 | a31 | a32 | a33 | a34 |
| SIN(4Θb) | a40 | a41 | a42 | a43 | a44 |

where Θa and Θb are the Azimuthal Angles through which Rotation two Rotatable Components are caused to Rotate. It will be shown supra, in TABLE 2 of the "DATA ACQUISITION" Section herein, that a Form-wise Equivalent Twenty-Five (25) Element Matrix can be arrived at by Application of Mathematical Equations to Empirically arrived at Intensity Value Data.

With the foregoing "Generalized Introduction" in mind, it is to be understood that the following discussion will focus upon a present invention embodiment for an IR Ellipsometer or Polarimeter System in which two (2) Components of which are caused to Rotate to various Azimuthal Angle Settings during Data Acquisition in a Calibration Procedure. In work performed to date each Rotated Component has been caused to assume Nine (9) Settings, leading to measurement of a total of Eighty-One (81), (eg. 9×9=81). It is to be understood, however, that a Triple Fourier Series approach could be utilized by causing three (3) present invention Ellipsometer or Polarimeter System Components to Rotate during a Calibration Procedure, and in general a "Multiple" Fourier Series approach to Calibration could be practiced with the Degree of the Fourier Series being determined generally by the number of present invention IR Ellipsometer or Polarimeter System Components which are caused to assume Rotated Settings at various Azimuthal Angles while Intensity Value Data are acquired. If Three (3) Components were caused to so Rotate, the formation of a Data Set with Three-Dimensions, and many more Elements would occur, (eg. where Nine (9) Azimuthal Settings for each of Three (3) Rotated IR Ellipsometer System Components are involved, there will be (9×9×9)=729 such Three (3) Dimensional Data Set rather the (9×9=81) for a Two (2) Dimensional Data Set). Fortunately, the added complexity has not been found necessary to practice the present invention, however.

It is again noted that Component settings can alternatively be achieved by Tilting Berek-type Variable Compensators, or application of Electric or Magnetic Fields to Variable Compensators known as Kerr, Pockles, Liquid Crystal, Voight and Coton-Mouton, or by sliding Babinet/Soleil type Variable Compensators. That is any appropriate approach to "Setting" a Component is to be considered within the scope of the present invention, and functionally equivalent to "Rotation" of a Component.

As well, it should be understood that Coefficients of a Mathematical Series other than a Fourier Series can be used in a similar manner and such use is within the scope of the present invention. To date, however, realization efforts have been focused upon use of Fourier Series Coefficients, and in the following Fourier Series Coefficients will be used to demonstrate the present invention.

Continuing, for insight, it is to be noted that in the (RARP) Calibration Procedure a present Compensator means will be found in a fixed Azimuthal Angle relationship with a Sample System (SS). In the (RPRC) scenario, a similar result exists, but it is the Analyzer means and Detector System which can not be distinguished one from the other. In the (RCRC) scenario the Source-Polarizer means combination, and the Analyzer means-Detector System combination groups will each appear as single "Lumped" elements. Also, in an (RARC) scenario the Polarizer and Source would be "Lumped". In said Generalized Overall Transfer Function Representation it is then to be understood that any two (2) or more Ellipsometer or Polarimeter System Components which maintain a fixed Azimuthal Angle with respect to one another during use or during a Calibration Procedure, are, by necessity, considered as "Lumped" In effect, the overall Ellipsometer or Polarimeter System will be unable to distinguish that two (2) Stationary Components are present. Again, a Sample System and a Compensator means which is not required to be rotated during a Calibration Procedure are "Lumped" into the Sample Mueller Matrix (MS); and a Source and a Polarizer Means, in a Calibration Procedure which does not require the rotation of said Polarizer means are considered as "Lumped" into a Stokes Vector (S); and a Detector and a Analyzer means, in a Calibration Procedure which does not require rotation of said Analyzer means are "Lumped" into said Detector Vector (A). The present invention Calibration Procedure however, does allow for distinguishing individual Components which comprise such "Lumped" elements, by providing that additional Data can be taken with one Component of a "Lumped" system of elements removed, (and perhaps replaced with an alternative component, such as effected by removing a present Sample System (SS) and inserting an "Alternative Sample System" including equivalents thereto, in its place. Note that an "Alternative Sample System" can be formed as a Composite of an original Sample System per se, in series with, for instance, a Berek-type Compensator). It should, at this point, be understood that a particularly relevant situation develops in the case where a Sample System and a Compensator means comprise a "Lumped" component or element. That is, it is necessary to distinguish a Compensator means and obtain specific Compensator Component Calibration Parameters in order that the present invention be applicable in general Sample System investigation.

Proceeding then, it is noted that Evaluated Calibration Parameters contained in Matrix Element Determining Equations serve to compensate for certain Non-Idealities in specific Mathematical Representations, (ie. Mathematical Models), of IR Ellipsometer System Components, (or perhaps "Lumped" combinations of Components or Component(s) and a Sample System), and said Matrix Element Determining Equations can equivalently be viewed as Determining of Double Fourier Series Coefficients. That is for instance, Multiplication of a series of IR Ellipsometer System Component Transfer Function Characterizing Matrices, in simultaneous conjunction with Rotation Matrices, (which serve to shift Coordinate Systems between System Component Transfer Function representing Matrices), in an appropriate IR Ellipsometer System representing order, provides an overall Transfer Function for a specific IR Ellipsometer System Configuration. Said Transfer Function can be represented as an Intensity Value Transfer Function Matrix with Elements thereof corresponding to Double Fourier Series Coefficients, said Matrix Elements thereof each being defined by Equations which include said Calibration Parameters therein. When known, Values for Calibration Parameters make it possible to arrive at Calibrated IR Ellipsometer Component Representing Matrices by application thereof to IR Ellipsometer System representing "Shell Form trices" With Calibrated "Shell Form Matrices" in place, it then becomes possible, knowing the Polarization State of a Polarized Electromagnetic Beam entered to the Calibrated Matrix Represented IR Ellipsometer or Polarimeter System, to calculate the expected Polarization State of a Polarized Electromagnetic Beam exiting therefrom. (Note, Calibration Parameter containing Equations for Double Fourier Series Coefficients are preferably achieved by way of an IR Ellipsometer or Polarimeter System Component Representing Matrix Multiplication Procedure. It is noted, however, that the a Functional Relationship between Input and Exiting Polarized Beam Polarization States can be achieved by other than Matrix Multiplication and be within the scope of the present invention).

It is described supra that Empirically Measured Numerical Values analogically corresponding to each effective Matrix Element Double Fourier Series Coefficient Defining Calibration Parameter containing Equation can be obtained, and the present invention Calibration Method utilizes such via a Mathematical Regression, (eg. Levenburg-Marquard), process to arrive simultaneously at "Mean-Square-Error-Best-Fit" values, or a similar approach, for said Calibration Parameters which are present. A book which describes Mathematical Regression is titled "Mathematical Recipes in C", Cambridge University Press, 1988, and said book is incorporated by reference hereinto.

In summary of the foregoing then, to practice the present invention certain Calibration Parameters which are present in Matrix Element Determining Equations of Mathematical Representations, (Characterizing "Shell-Form" Matrices), of said IR Ellipsometer System Component, (or perhaps "Lumped" IR Ellipsometer System Component Transfer Function), must be evaluated. When Two (2) IR Ellipsometer System Components are caused to rotate to various Angle Settings during Intensity Data Acquisition in the present invention Calibration Method, said Matrix Elements can be identified and calculated as the Coefficients of Double Fourier Series. Once evaluated, said Calibration Parameter Values can be thought of as then being "plugged into" Elements of "Shell Form Matrices" which "Shell Form Matrices" then accurately Characterize and Mathematically Represent, in Matrix Form, above mentioned, "Calibrated", IR Ellipsometer System Component, (or perhaps "Lumped" IR Ellipsometer System Components), Transfer Functions. Calibrated "Shell Form Matrices" which Mathematically Represent IR Ellipsometer System Components, (Discrete or "Lumped"), are then utilized, via a Matrix Multiplication Procedure, to calculate what effect said IR Ellipsometer System should have on a Polarized Electromagnetic Beam caused to pass therethrough, so that the effect a Sample System (SS) placed in the path of a Polarized Electromagnetic Beam in said IR Ellipsometer System has on said Polarized Electromagnetic Beam can be distinguished, thereby allowing determination of PSI and DELTA Values, or perhaps a full Mueller Matrix (MS) of an investigated Sample System. That is, otherwise unexplained effects can be attributed to an investigated Sample System. As discussed below, Calibration Parameter evaluation is accomplished by performing Mathematical Regression of said Calibration Parameter containing present invention System Component Characterizing Matrix Element Determining Equations onto certain analogically corresponding Empirically Determined Numerical Values for Double Fourier Series Coefficients, which Empirically Determined Numerical Values are found as Elements in Matrices which correspond to a Double Fourier Series. This Calibration procedure will become more clearly understood by reference to the disclosure which follows directly.

DATA ACQUISITION

Continuing, to provide Numerical Values for said required Calibration Parameters, a number of mathematical steps are performed involving Empirically obtained data.

First, the Method of the present invention Calibration Procedure requires that a Polarized Electromagnetic Beam, typically comprised of a plurality of Wavelengths in the IR Range, be accessed. In the presently investigated IR Ellipsometry System, a Michelson Fourier Transform Infra-Red (FTIR) Continuous Wavelength Black Body Source System, in combination with a Polarizer means, is the Source thereof. In work performed to date Five-Hundred-Seventy-Two (572) IR Range Wavelengths, (eg. between two (2) microns and fourteen (14) microns long), were selected for use.

Next, for Calibration Parameter evaluation purposes, an IR Ellipsometer System is typically oriented in a "Straight-Through" configuration, such that no Sample System, (which is effectively the equivalent of utilizing a transparent Sample System), is present in the path of said Polarized Electromagnetic Beam. That is, an Electromagnetic Beam exiting the Source of an Electromagnetic Beam of IR Wavelengths is caused to pass through a Polarizer means, (thereby becoming polarized), and through at least a First Compensator means and Analyzer means IR Ellipsometer System Components, and is then received at the IR Ellipsometer System Detector whereat its Intensity is measured. With the IR Ellipsometer System so configured, Data relating Detector Measured Signal Intensity Values for various Azimuthal settings of two (2) Rotatable Elements (eg. Polarizer means and/or Analyzer means and/or Compensator means), is typically acquired. (Note that two (2) Compensator means, one before and one after a Sample System, can also be Rotated). The next step is to proceed through a series of Azimuthal Settings for one of said IR Ellipsometer Rotatable System Components, and at each said setting, proceed through a series of Azimuthal Settings for the other Rotatable IR Ellipsometer System Component. At each combination of Azimuthal Settings Intensity Detector Derived Readings are obtained. Present invention results were obtained utilizing a total of Nine (9) Settings for each selected Rotatable IR Ellipsometer System Component, with the result being that at each Wavelength Eighty-One (81) Intensity Values are Empirically Acquired. As Five-Hundred-Seventy-Two (572) Different Wavelengths are involved, a large Data Set of Intensity Value Data are acquired.

As a sideline, it should then be obvious that a number of Three-Dimensional Contour Plots, (ie. one for each wavelength present, which in presently documented work is Five-Hundred-Seventy-Two (572), but which number is not a imitation), in which a Vertical axis presents Detector measured Intensity, and two Mutually Orthogonal axes identify simultaneous Azimuthal Settings of the Rotatable System Components, can be formed, (see FIG. 7*a* for instance). For convenience, said Three-Dimensional Contour Plots for the various Wavelengths investigated can be visually displayed. As well, by selection of Intensity Readings corresponding to similar simultaneous Azimuthal Angle Settings from each Wavelength specific Three-Dimensional Contour Plot, a series of Two-Dimensional Plots of Intensity vs. Wavelength can be constructed and displayed, (see FIG. 7*b* for instance). In presently documented work, wherein Nine (9) Azimuthal Angle Settings were utilized in each Rotatable System Component, a total of Eighty-One (81) such Two-Dimensional Plots were achievable, each of which can provide Intensity vs. Wavelength over five-Hundred-Seventy-Two (572) Wavelenghts. That is, Eighty-One (81) combinations of distinguishable simultaneous Azimuthal Settings of two IR Ellipsometer System Rotatable System Components were available. (Note that it is not necessary to actually form the identified Plots to practice the described present invention Calibration Procedure, but rather said Plots are a convenient way to quickly visualize the results).

Next, the Method of the presently described Calibration Procedure typically provides that an arbitrary "Sample System" be placed into the IR Ellipsometer System, (between the Polarizer means and Analyzer means), with a fixed Angle-Of-Incidence (AOI) effected between the perpendicular to the surface of said arbitrary Sample System and the investigating Polarized Electromagnetic Beam of IR Wavelengths. (Note, The (AOI) selected for use is typically not critical to the Calibration procedure). In this "Sample Present" configuration a second Data Set of Eighty-One (81) Intensity Values are acquired for each Wavelength utilized, and Three-Dimensional Contour, and Two-Dimensional Plots of Intensity vs. Wavelength can again be achieved. (Again, note that it is not necessary to actually form the identified Plots to practice the presently described Calibration Procedure). It is to be understood that the Polarized Electromagnetic Beam of IR Wavelengths can be caused to reflect from or pass through said Sample System during this procedure.

It is also disclosed that where the Rotated Polarizer Means-Rotated Analyzer means approach is utilized, one (1) or two (2) additional Data acquisition cases are typically utilized. That is Data can be taken for the Straight-Through, and for the Arbitrary Sample System present IR Ellipsometer System, configurations, with the Compensator means removed therefrom, or perhaps with an Alternative Sample System replacing the original Sample System. Acquisition and use of said additional Data allows more accurate determination of Calibration Parameter values, and allows specific identification of Compensator means Calibration Parameters as distinct from a "Lumped" combination thereof with a Sample System. It is emphasized, however, that where any present Compensator means is a Rotated Component it has been found unnecessary to determine the identified additional Data because said additional data, if achieved, would serve to distinguish, for instance, Calibration Parameters for the Source and Polarizer means in a "Lumped" "Source and Polarizer means" combination, or for the Detector and Analyzer means in a "Lumped" "Detector and Analyzer means" combination. Generally there is no need to determine said distinctions, as it is a Sample System which is to be investigated, and the IR Ellipsometer System Component it typically becomes "Lumped" together with is a Compensator Means.

Continuing, it is to be understood that a typical Twenty-Five (25) Element Square Matrix of Double Fourier Series Coefficients, (eg. a Matrix with Five (5) Horizontal and Five (5) Vertical Elements), can be constructed utilizing the Empirically obtained identified Intensity Data.

In work performed to date specific Numerical Values for The Twenty-Five (25) Elements of each presently described Five (5)×Five (5) Double Fourier Series Coefficients containing Square Matrix, have been mathematically provided by utilizing the described Empirically obtained Detector Provided Intensity Value Data in the following Fourier Series Coefficient Evaluating Equations:

$$a(0,0) := \frac{1}{4}\left(\sum_{l=0}^{L}\left(\sum_{k=0}^{K} V(\theta a, \theta b)\right)\right)$$

$$a(m,0) := \frac{1}{2}\left(\sum_{l=0}^{L}\left(\sum_{k=0}^{K} V(\theta a, \theta b)\,\phi\, m(\theta b)\right)\right)$$

$$a(0,n) := \frac{1}{2}\left(\sum_{l=0}^{L}\left(\sum_{k=0}^{K} V(\theta a, \theta b)\,\phi\, n(\theta a)\right)\right)$$

$$a(m,n) := \sum_{l=0}^{L}\left(\sum_{k=0}^{K} V(\theta a, \theta b)\,\phi\, m(\theta b)\,\phi\, n(\theta a)\right) \quad \text{EQS.7}$$

where "l" and "k" identify the Matrix Element, and where L and K are the number of Samples taken per revolution for each of the Rotated components respectively, and V(O1,O2) is the voltage signal measured at each azimuthal angle combination, and where:

$$\phi 0\,(\theta) := 1$$

$$\phi 1\,(\theta) := \mathrm{Cos}\,(2\theta)$$

$$\phi 2\,(\theta) := \mathrm{Sin}\,(2\theta)$$

$$\phi 3\,(\theta) := \mathrm{Cos}\,(4\theta)$$

$$\phi 4\,(\theta) := \mathrm{Sin}\,(4\theta) \quad \text{EQS. 8}$$

A single equation which can calculate all Elements of an "N" Element Matrix can be used to express the above, where Kronecker delta functions are used to provide the fraction in front of the Summation Signs, said single Equation being:

$$a(m,n) := \frac{1}{(1+\delta_K(m,0))(1+\delta_K(n,0))}\sum_{l=0}^{L}\left(\sum_{k=0}^{K} V(\theta a, \theta b)\,\phi\, m(\theta b)\,\phi\, n(\theta a)\right) \quad \text{EQ.9}$$

In light of the above, it is helpful to note that Fourier Coefficients, (eg. A, B, C, D, and E) of a Single Fourier Series, in combination with Basis Functions can be represented by:

A*(D.C.);

B*(Sin (2w));

C*(Cos (2w));

D*(Sin (4w));

and

E*(Cos (4w)). EQ. 10

Values for said Fourier Coefficients can be obtained by performing a Fourier Analysis of Data obtained Empirically during stepwise Rotation of the Azimuthal Angle of One (1) IR Ellipsometer Rotatable System Component. If the Azimuthal Angles of two (2) such IR Ellipsometer System Rotatable Components are set by Rotation thereof, a Twenty-Five (25) Element Square Matrix results. (Note that a Nine (9) element Matrix could be formed and utilized if only the D.C. term and the Sin (2w) and Cos (2w) Basis Function terms are utilized, or a Forty-Nine (49) Element Matrix could be formed if Sin (6w) and Cos (6w) Basis Function terms are utilized. The use of a Twenty-Five (25) Element Square Matrix is thus not a limitation of the present invention).

A representative Twenty-Five (25) Element Matrix is:

TABLE 2

| | 1 | COS(2Θa) | SIN(2Θa) | COS(4Θa) | SIN(4Θa) |
|---|---|---|---|---|---|
| 1 | a00 | a01 | a02 | a03 | a04 |
| COS(2Θb) | a10 | a11 | a12 | a13 | a14 |
| SIN(2Θb) | a20 | a21 | a22 | a23 | a24 |
| COS(4Θb) | a30 | a31 | a32 | a33 | a34 |
| SIN(4Θb) | a40 | a41 | a42 | a43 | a44 |

The Elements of the Twenty-Five Element Matrix; a00, a01, a02, a03, a04, a10, a11, a12, a13, a14, a20, a21, a22, a23, a24, a30, a31, a32, a33, a34, a40, a41, a42, a43, a44, are Coefficients of a Double Fourier Series arrived at from Data acquired while setting the Azimuthal Angles of two IR Ellipsometer System Components. (eg. for instance:

a11*(Cos (2Θa))*(Cos (2Θb));

and a22*(Sin (2Θa))*(Sin (2Θb)); EQS. 11 are terms of said Double Fourier Series, where (Θa) and (Θb) are azimuthal angles of First and Second IR Ellipsometer System Rotatable Components respectively), (see evaluating equations 7 infra).

(Note the equivalence in Form of the just presented TABLE 2, Twenty-Five (25) Element Matrix which is arrived at by application of Mathematical Equations to Empirically obtained Intensity Data, to the TABLE 1 Twenty-Five (25) Element Matrix which was presented infra, in the "GENERALIZED ELLIPSOMETER OR POLARIMETER SYSTEM" Section herein, which was arrived at by, for instance, Analytical Matrix Multiplication).

(Derivation and discussion of the Double Fourier Series is provided in a book titled "Fourier Series & Integrals of Boundary Value Problems", Wiley 1982, which reference is incorporated by reference herein).

CALIBRATION PARAMETER EVALUATION

With TABLE 2 presented Numerical Values for the resulting Elements of the above identified Empirically obtained Wavelength specific typically Twenty-Five (25) Element Square Matrices available, it is then possible to, by way of a Regression, (eg. Levenburg-Marquard), procedure, simultaneously evaluate Calibration Parameters in Matrix Element Determining Equations of the "Shell Form Matrices" which characterize the above identified IR Ellipsometer System Components. That is, the required Values of Calibration Parameters which plug into Elements of said "Shell Form Matrices" mentioned infra and presented supra, which resulting "Calibrated" "Shell Form Matrices" characterize each of the above identified IR Ellipsometer System Components, or "Lumped" combinations thereof, (when said Matrices are calibrated for non-idealities in the System Components), are simultaneously achieved by application of said Regression Procedure. (Note, it is a non-limiting practice to normalize each Matrix of typically Twenty-Five (25) Elements to one of the Elements present therein. Typically the product of the D.C. terms in each Single Fourier Series serves as the Normalization Element. Similar practice is appropriate with respect where other number of Element Matrices are utilized. Also note that it is not necessary to evaluate every possible Calibration Parameter in a Regression Procedure. That is, a user might elect to fix one or more Calibration Parameter Values and evaluate the remaining Calibration Parameters via a Regression Procedure. This might be done where values for certain Calibration Parameters are already known, or where one or more Sample System Investigation System Components are assumed to be ideal).

It is then to be understood that the approach taken to evaluation of the Calibration Parameters which plug into said "Shell Form Matrices" is regression of Calibration Parameter containing Equations onto Values, obtained by Empirical efforts, for analogically corresponding Elements of the Twenty-Five (25) Element Square Matrices. This is possible because Mathematical Multiplication of appropriate Rotation Matrices and Matrices which represent a Detector, a Polarizer means, one or more Compensator mean(s) and an Analyzer means, (along with a Sample System where appropriate), in an IR Ellipsometer System representing order, provide Calibration Parameter containing Equations which analogically correspond to the Empirically Evaluated Elements in the described Empirically Determined Twenty-five (25) Element Square Matrix, Values of Elements of which are evaluated by application of Mathematical Equations to Empirically obtained Intensity Value Data.

To aide with understanding, it should be appreciated that one could expand each Empirically determined Twenty-five (25) Element Square Matrix into a series summation of terms in a Twenty-Five Term Double Fourier Series representing Equation which would equate to an analogically equivalent measured Intensity Value such as generally represented by EQ. 1 infra, wherein said TABLE 2 Matrix Elements are present as Coefficients of appropriate terms of said resulting Double Fourier Series. It will be recalled that an equation, (EQ. 4), with appropriate terms and with Coefficients associated therewith, in fact is obtained if one multiplies through all Rotation, Polarizer means (P), Compensator means (C), Analyzer means (A) and Detector (DET), (and Sample System if present), representing Matrices, an IR Ellipsometer System representing order. Thus, simultaneous Regression of each said Mathematically Determined Coefficient defining Calibration Parameter containing Equation, onto each of the analogically corresponding Empirically determined Numerical Values for the Twenty-five (25) Empirically obtained Matrix Elements, for each such Wavelength and Component Setting case Square Matrix, provides values of Calibration Parameters in the Mathematically Determined Coefficient defining Calibration Parameter containing Equations. Said Calibration Parameter values being determined so as to simultaneously provide a good fit to all said Empirically achieved Data.

It is again noted that in work actually performed, Numerical Values for Elements in at least two (2) Twenty-Five (25) Element Square Matrices are Empirically obtained at each of five-Hundred-Seventy-Two (572) Wavelenghts. As described infra, one of said Twenty-Five (25) Element Square Matrix at a Wavelength typically corresponds to a Straight-Through IR Ellipsometer System configuration, and another to an IR Ellipsometer System in which an Arbitrary Sample System is present. (Note, however, that a procedure involving two "Sample-Present" Configurations, wherein two different Arbitrary Samples are used, could be utilized as well. Also, note that a "Straight-Through" Configuration is an effective "Sample-Present" Configuration wherein the Sample is transparent). As described infra, Matrix Multiplication of a series of IR Ellipsometer System Component representing Matrices, (including appropriate Rotation Matrices), said Matrices being oriented in a IR Ellipsometer System representing order, can be caused to provide Calibration Parameter containing Equations for corresponding Matrix Elements. The large amount of Data utilized in the Regression between Empirically Determined Matrix Element Numerical Values, and Mathematically Determined Calibration Parameter containing Equations which correspond thereto, serves to allow determination of precise Calibration Parameter Values. It is noted that said described present invention Calibration Procedure actually leads to determination of PSI and DELTA, (or perhaps Elements of a Sample System representing Mueller Matrix-see (RCRC) Calibration procedure supra), Values for the arbitrary Sample System, along with Calibration Parameters in the Equations which determine various IR Ellipsometer System Component representing "Shell Form Matrix" Elements. In fact the described Calibration procedure could be utilized to provide Sample System PSI and DELTA Values for any Sample System. However, once Calibration Parameters for use in the "Shell Form Matrix" Elements, (which "Shell Form Matracies" represent IR Ellipsometer System Components), are known and utilized by incorporation into appropriate Matrix Element Determining Equations, it has been found that it is usually necessary to Rotate only a single Rotatable IR Ellipsometer System Component while Empirically obtaining Data, to allow determination of PSI and DELTA values for a Sample System. This is fortunate as it greatly reduces the amount of Data which must be obtained when applying a Calibrated IR Ellipsometer System. It must be understood, however, that Rotation of two Components during Data Acquisition, allows evaluation of Elements of a Mueller Matrix for a Sample System.

The following is a listing of the "Shell Form Matrices" showing the Elements thereof where Calibration Procedure Regression Determined Numerical Values for the above indicated Calibration Parameters, (as utilized in the Computer Program Print-Outs included herein supra), are plugged to provide Calibrated System Component Transfer Function Characterizing Matrices:

ROTATION OF COORDINATE AXES $$\begin{bmatrix} 1 & 0 & 0 & 0 \\ 0 & \cos(2\theta) & \sin(2\theta) & 0 \\ 0 & -\sin(2\theta) & \cos(2\theta) & 0 \\ 0 & 0 & 0 & 1 \end{bmatrix} \quad \text{EQ.12}$$

where for various Rotation cases θ is:

Polarizer—Ps;

Analyzer—As;

Single Compensator—Cs;

Where Two Compensators are Present:

First Compensator—θa;

Second Compensator—θb;

Detector (used in RARP case) D.

(Note that Ps,Sa,Cs and D can be positive or negative).

SAMPLE $$\begin{bmatrix} 1 & -\cos(2\psi) & 0 & 0 \\ -\cos(2\psi) & 1 & 0 & 0 \\ 0 & 0 & \sin(2\psi)\cos(\Delta) & \sin(2\psi)\sin(\Delta) \\ 0 & 0 & -\sin(2\psi)\sin(\Delta) & \sin(2\psi)\cos(\Delta) \end{bmatrix} \quad \text{EQ.13}$$

COMPENSATOR(S)

$$\begin{bmatrix} 1 & -\cos(2\psi x) & 0 & 0 \\ -\cos(2\psi x) & 1 & 0 & 0 \\ 0 & 0 & \sin(2\psi x)\cos(\Delta x) & \sin(2\psi x)\sin(\Delta x) \\ 0 & 0 & -\sin(2\psi x)\sin(\Delta x) & \sin(2\psi x)\cos(\Delta x) \end{bmatrix} \quad \text{EQ.14}$$

(where "x" is replaced by "c" if one Compensator is present, and where "x" is replaced by each of "a" and "b" respectively, where Two (2) Compensators are present)

POLARIZER $$\begin{bmatrix} 1+\alpha p & 1-\alpha p & 0 & 0 \\ 1-\alpha p & 1+\alpha p & 0 & 0 \\ 0 & 0 & 2\sqrt{\alpha}\, p & 0 \\ 0 & 0 & 0 & 2\sqrt{\alpha}\, p \end{bmatrix} \quad \text{EQ.15}$$

ANALYZER $$\begin{bmatrix} 1+\alpha a & 1-\alpha a & 0 & 0 \\ 1-\alpha a & 1+\alpha a & 0 & 0 \\ 0 & 0 & 2\sqrt{\alpha}\, p & 0 \\ 0 & 0 & 0 & 2\sqrt{\alpha}\, p \end{bmatrix} \quad \text{EQ.16}$$

DETECTOR (ROTATING COMPENSATOR CASES (EG. (RPRC) RCRC))

[1 A2 A2 A3] EQ. 17

DETECTOR (ROTATING ANALYZER CASES (EG. (RARP) (RARC))

[1 βd Cos (2 D) βd Sin (2 D) 0] EQ. 18

SOURCE $$\begin{bmatrix} 1 \\ S1 \\ S2 \\ S3 \end{bmatrix} \quad \text{EQ.19}$$

(Note, Forms of the "Shell Form Matrices" vary depending on the number of Components Rotated while obtaining Empirical Data. The "Shell Form Matrices" provided are appropriate for the case in which a Twenty-Five (25) Element Double Fourier Series representing Matrix is utilized, that is, where two (2) Components are Rotated).

With Transfer Function Characterizing Calibration Parameters for entry into said "Shell-Form Matrices", (which represent various System Components), then available, the Calibration Procedure is completed.

SPECIFIC CALIBRATION PROCEDURE CASES

For the purpose of providing complete disclosure, the following provides specific discussion and the TABLE 1 System Component representing Matrix Element Calibration Parameter Containing Equations which regress onto each of the Matrix Element Values of an appropriate TABLE 2 Empirically determined Twenty-Five (25) Element Matrix, for the cases where:

a. The IR System Components Rotated while obtain the Empirical date which are used in determining the Numerical Values of Elements of a Twenty-Five (25) Element Matrix are the Polarizer means and the Analyzer means (RPRA).

b. The IR System Components Rotated while obtain the Empirical data which are used in determining the Numerical Values of Elements of a Twenty-Five (25) Element Matrix are the Polarizer means and the Compensator means (RPRC). While not specifically presented, it is to be understood that a similar approach applies to a Rotated Analyzer means and Compensator means (RARC).

c. The IR System Components Rotated while obtain the Empirical data which are used in determining the Numerical Values of Elements of a Twenty-Five (25) Element Matrix are two Compensator means (RCRC).

(It is felt that by providing the following discussion of each identified specific case and the final results of the many pages of MathCad calculations necessary to arrive at the disclosed final results that the requirement of full disclosure is met, and that it is unnecessary to provide said many pages of MathCad calculations. It is also noted that the Analytically Derived Calibration Parameter containing equations for Double Fourier Series Coefficients which are provided in the following, are not necessarily "expressly" derived in practice of the present invention method. The relationships are, however, "effectively" derived and utilized in error reducing Calibration Parameter evaluation regression. The term "effective", as regards such Analytically derived Equations, is utilized to make this point clear. That is, even though for disclosure purposes, definite specific Calibration Parameter containing Equations for Multiple Fourier Series Coefficients will be provided, in practice of the present invention it is permissible, and within the scope of the present invention, to do a mathematically equivalent procedure which does not result in said specifically calculating said Matrix Element Representation Calibration Parameter containing Multiple Fourier Series Coefficient Equations. It is also to be understood that the Method of the present invention could be practiced utilizing Calibration Parameter containing Coefficients from a Mathematical Series other than a Fourier Series, (eg. a series based upon Bessel Functions or Legendra Polynomials). In such a case the Calibration Parameter containing Equations for the Coefficients thereof would not be the same as those presented herein, but the application of a regression procedure, onto analogically corresponding numerical values, to evaluate Calibration Coefficients therein in said Equations would similarly be performed. As well, different Mathematical Formula would have to be employed to arrive at the Empirically derived Numerical Values obtained from measured Intensities which are regressed onto).

In the following discussion, for demonstrative purposes, it is assumed that a Two-Dimensional Fourier Series approach is utilized.

FOR ROTATING ANALYZER AND ROTATING POLARIZER CALIBRATION PROCEDURE (RPRA)

The method of Calibrating for Non-Idealities in Mathematical Representations of Rotated and Non-Rotated Components of a Sample System Investigating System described directly is applicable to Ellipsometers and Polarimeters which are sequentially comprised of a Source of a Beam of Electromagnetic wavelengths, a Polarizer means, typically for imposing a state of polarization upon said Beam of Electromagnetic wavelengths, a Stage for supporting a Sample System, an Analyzer means, typically for selecting a state of polarization in said Beam of Electromagnetic wavelengths and a Detector System. In addition, the Sample System Investigating System is further comprised of at least a First Compensator means, said at least a First Compensator means being positioned in said Sample System Investigating System at a location selected from the group consisting of, before and after, said Stage for supporting said Sample System. The Sample System Investigating System can also optionally comprise a Second Compensator means positioned in said Sample System Investigating System at a location complementary to said First Compensator means, said position being selected from the group consisting of, respectively, after and before, said Stage for supporting said Sample System.

An exemplary (RPRA) Calibration Method comprises the steps of:

Step a. Empirically obtaining at least three data sets, each of which data sets consists of intensity values measured by said detector system. Said intensity values being a function of wavelength and of rotated settings of azimuthal angles of said analyzer means and said polarizer means of said sample system investigating system. One of said data sets being obtained with said sample system investigating system oriented in a "sample-present" configuration. And a second of which data sets being obtained with said sample system investigating system oriented in a configuration selected from the group consisting of an "Alternative Sample-Present" and a "Straight-Through" configuration. And a third of which data sets is obtained with said sample system investigating system oriented in a configuration selected from the group consisting of, (wherein a present compensator means is removed, and wherein an "Alternative Sample-System" is substituted for a previously present "Sample-System"). Said "Straight-Through" configuration results from orienting said sample system investigating system such that a beam of electromagnetic wavelengths provided by said source of a beam of electromagnetic wavelengths is caused to pass through said polarization means, through said analyzer means and into said detector system, and the "Sample-Present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that in either of said "Straight-Through" or "Sample-Present" configurations of said sample system investigating system, said beam of electromagnetic wavelengths is also caused to pass through any present compensator means;

Step b. Applying mathematical formula to said data sets to provide empirically derived numerical values for coefficients of two-dimensional mathematical series, said dimension of said two-dimensional mathematical series being determined by the number of sample system investigating system components, namely the analyzer means and the polarizer means, which were caused to assume various azimuthal angle settings during the obtaining of data sets in step a.;

Step c. Effectively deriving analytical non-ideality compensating calibration parameter containing equations for two-dimensional mathematical series coefficients, each of which effective analytically derived non-ideality compensating calibration parameter containing equations for two-dimensional mathematical series coefficients is analogically equivalent to numerical values for corresponding two-dimensional mathematical series coefficients empirically determined by applying mathematical formula to the data sets as in Step b., said analogically equivalent non-ideality compensating calibration parameter containing equations for two-dimensional mathematical series coefficients being achievable by performing matrix multiplication of non-ideality compensating calibration parameter containing matrices which represent sample system investigating system components and rotation matrices, each thereof being oriented in a series of said sample system investigating system component and rotation matrices to appropriately represent a "straight-through" or a "sample present" configuration of said sample system investigating system;

Step d. performing a simultaneous mathematical regression of Step c., analytically arrived at effective non-ideality compensating calibration parameter containing equations for mathematical of two-dimensional mathematical coefficients, onto analogically equivalent numerical value for two-dimensional mathematical series coefficients as arrived at in Step b.; such that non-ideality compensating calibration parameters in said effective non-ideality compensating calibration parameter containing equations for two-dimensional mathematical series coefficients are simultaneously evaluated, based upon an error reducing criteria; said non-ideality compensating calibration parameters being for said source of a beam of electromagnetic wavelengths, said polarizer means, said compensator means, said analyzer means and said detector system, each separately, with the arbitrary sample system characterization (PSI & DELTA) also being provided.

(Note, It is possible that the (RPRA) approach can be practiced utilizing only two Data Sets, wherein one Data Set is empirically obtained with only a Sample System present, and wherein one Data set is empirically obtained with a Sample System and a Compensator are present. The only drawback of such a simplified approach is that, typically Calibration Parameter evaluation accuracy might be reduced as compared to results achievable when the above recited Method is practiced).

Following directly are Print-Outs showing specific Calibration Parameter Containing Equations which analogically correspond to the Empirically Determined Numerical Values for the Double Fourier Series Matrix Elements, (ie. Coefficients), which Calibration Parameter Containing Equations are Regressed onto said Matrix Element Numerical Values to simultaneously provide Numerical Values for each Calibration Parameter.

In this (RPRA) case, the following Calibration Parameters are simultaneously evaluated:

| | Print-Out Symbol |
|---|---|
| Source: | |
| S0 (not present as normalization basis for S1, S2 and S3) | |
| S1 | Sr1 |
| S2 | Sr2 |
| S3 | Sr3 |
| Polarizer: | |
| ALPHAp | αp |
| Lumped Sample System and Compensator: | |
| PSI (1) | ψ |
| DELTA (1) | Δ |
| Sample System: | |
| PSIs | ψ |
| DELTAs | Δ |
| Compensator: | |
| PSIc | ψ |
| DELTAc | Δ |
| Analyzer: | |
| ALPHAa | ψa |
| Detector: | |
| A0 (not used) | |
| A1 (not used) | |
| A2 (not used) | |
| A3 (not used) | |
| equivalent data containing alternative parameters utilized | βD & D |
| Rotation Angles: | |
| Rotation Azimuthal Angle to Analyzer | As |
| Rotation Azimuthal Angle to Polarizer | Ps |

(NOTE, the same PSI and DELTA in the Calibration Parameter containing Fourier Coefficient Equations represent Compensator Means, or Sample, or Lumped combination thereof based upon presence during specific data acquisition. That is, the Calibration Parameter containing Matrix Element Equations do not change because the Sample or Compensator Means or both are present. The user of the present invention must simply keep track of what Data Set corresponds to what configuration of present Sample System, and/or Compensator Means).

(Note that values for "Lumped" Sample System and Compensator Calibration Parameters are distributed by the obtaining of a Third Data Set as described above. That is, even though the Azimuthal Angle between the Sample System and the Stationary Compensator is constant during the (RPRA) Calibration Procedure, the obtaining of Data with said Compensator removed, as well as present in a "Sample Present" System Orientation, allows distinguishing the Sample System and Compensator per se. It is also to be understood that the same Matrix element equations apply in the case where a Compensator is, and is not, present. One must simply keep in mind what PSI and DELTA are being achieved, that is, for a composite "Lumped" Sample System and Compensator, or for a Sample System per se.)

Rotating Polaizer/Rotating Analyzer $$\gamma_{Ap}=\frac{(1+\sqrt{\alpha_A}\ )^2}{2}\qquad \gamma_{An}=\frac{(1-\sqrt{\alpha_A}\ )^2}{2}\qquad \gamma_{Pp}=\frac{(1+\sqrt{\alpha_P}\ )^2}{2}\qquad \gamma_{Pn}=\frac{(1-\sqrt{\alpha_P}\ )^2}{2}$$

$$\begin{aligned}a_{00} = {} & 1+\alpha_P+\alpha_A+\alpha_A\cdot\alpha_P-\gamma_{Ap}\cdot\beta D\cdot\cos(2\cdot D)\cdot\cos(2\cdot\psi)-\gamma_{Ap}\cdot\beta D\cdot\cos(2\cdot D)\cdot\cos(2\cdot\psi)\cdot\alpha_p\ldots+\\ & (-\gamma_{Pp}\cdot\cos(2\cdot\psi)\cdot\cos(2\cdot Ps)\cdot Sr1-\gamma_{Pp}\cdot\cos(2\cdot\psi)\cdot\sin(2\cdot Ps)\cdot Sr2)-\gamma_{Pp}\cdot\cos(2\cdot\psi)\cdot\alpha_A\cdot\cos(2\cdot Ps)\cdot Sr1\ldots+\\ & -\gamma_{Pp}\cdot\cos(2\cdot\psi)\cdot\alpha_A\cdot\sin(2\cdot Ps)\cdot Sr2+\gamma_{Pp}\cdot\gamma_{Ap}\cdot\beta D\cdot\cos(2\cdot D)\cdot\cos(2\cdot Ps)\cdot Sr1\ldots+\\ & \gamma_{Pp}\cdot\gamma_{Ap}\cdot\beta D\cdot\cos(2\cdot D)\cdot\sin(2\cdot Ps)\cdot Sr2+\gamma_{Ap}\cdot\beta D\cdot\sin(2\cdot D)\cdot\sin(2\cdot\psi)\cdot\cos(\Delta)\cdot\gamma_{Pp}\cdot\sin(2\cdot Ps)\cdot Sr1\ldots+\\ & \gamma_{Ap}\cdot\beta D\cdot\sin(2\cdot D)\cdot\sin(2\cdot\psi)\cdot\cos(\Delta)\cdot\gamma_{Pp}\cdot\cos(2\cdot Ps)\cdot Sr2\ldots+-2\cdot\gamma_{Ap}\cdot\beta D\cdot\sin(2\cdot D)\cdot\sin(2\cdot\psi)\cdot\sin(\Delta)\cdot\sqrt{\alpha_P}\ \cdot Sr3\end{aligned}$$

$$a_{01}=(1-\alpha_P)\cdot\left(\begin{array}{l}Sr1+Sr1\cdot\alpha_A-Sr1\cdot\gamma_{Ap}\cdot\beta D\cdot\cos(2\cdot D)\cdot\cos(2\cdot\psi)-\cos(2\cdot Ps)\cdot\cos(2\cdot\psi)\ldots+\\ -\cos(2\cdot Ps)\cdot\cos(2\cdot\psi)\cdot\alpha_A\ldots+\\ \cos(2\cdot Ps)\cdot\gamma_{Ap}\cdot\beta D\cdot\cos(2\cdot D)+\gamma_{Ap}\cdot\beta D\cdot\sin(2\cdot D)\cdot\sin(2\cdot\psi)\cdot\cos(\Delta)\cdot\sin(2\cdot Ps)\end{array}\right)$$

$$a_{02}=-(1-\alpha_P)\cdot\left(\begin{array}{l}Sr2+Sr2\cdot\alpha_A-Sr2\cdot\gamma_{Ap}\cdot\beta D\cdot\cos(2\cdot D)\cdot\cos(2\cdot\psi)-\sin(2\cdot Ps)\cdot\cos(2\cdot\psi)\ldots+\\ -\sin(2\cdot Ps)\cdot\cos(2\cdot\psi)\cdot\alpha_A+\sin(2\cdot Ps)\cdot\gamma_{Ap}\cdot\beta D\cdot\cos(2\cdot D)\ldots+\\ -\gamma_{Ap}\cdot\beta D\cdot\sin(2\cdot D)\cdot\sin(2\cdot\psi)\cdot\cos(\Delta)\cdot\cos(2\cdot Ps)\end{array}\right)$$

$$a_{03}=\gamma_{Pn}\cdot\left[\begin{array}{l}-\cos(2\cdot\psi)\cdot\cos(2\cdot Ps)\cdot Sr1+\cos(2\cdot\psi)\cdot\sin(2\cdot Ps)\cdot Sr2-\cos(2\cdot\psi)\cdot\alpha_A\cdot\cos(2\cdot Ps)\cdot Sr1\ldots+\\ \cos(2\cdot\psi)\cdot\alpha_A\cdot\sin(2\cdot Ps)\cdot Sr2+\gamma_{Ap}\cdot\beta D\cdot\cos(2\cdot D)\cdot\cos(2\cdot Ps)\cdot Sr1\ldots+\\ -\gamma_{Ap}\cdot\beta D\cdot\cos(2\cdot D)\cdot\sin(2\cdot Ps)\cdot Sr2+\gamma_{Ap}\cdot\beta D\cdot\sin(2\cdot D)\cdot\sin(2\cdot\psi)\cdot\cos(\Delta)\cdot\sin(2\cdot Ps)\cdot Sr1\ldots+\\ \gamma_{Ap}\cdot\beta D\cdot\sin(2\cdot D)\cdot\sin(2\cdot\psi)\cdot\cos(\Delta)\cdot\cos(2\cdot Ps)\cdot Sr2\end{array}\right]$$

$$a_{04}=-\gamma_{Pn}\cdot\left[\begin{array}{l}-\cos(2\cdot\psi)\cdot\sin(2\cdot Ps)\cdot Sr1-\cos(2\cdot\psi)\cdot\cos(2\cdot Ps)\cdot Sr2-\cos(2\cdot\psi)\cdot\alpha_A\cdot\sin(2\cdot Ps)\cdot Sr1\ldots+\\ -\cos(2\cdot\psi)\cdot\alpha_A\cdot\cos(2\cdot Ps)\cdot Sr2+\gamma_{Ap}\cdot\beta D\cdot\cos(2\cdot D)\cdot\sin(2\cdot Ps)\cdot Sr1\ldots+\\ \gamma_{Ap}\cdot\beta D\cdot\cos(2\cdot D)\cdot\cos(2\cdot Ps)\cdot Sr2-\gamma_{Ap}\cdot\beta D\cdot\sin(2\cdot D)\cdot\sin(2\cdot\psi)\cdot\cos(\Delta)\cdot\cos(2\cdot Ps)\cdot Sr1\ldots+\\ \gamma_{Ap}\cdot\beta D\cdot\sin(2\cdot D)\cdot\sin(2\cdot\psi)\cdot\cos(\Delta)\cdot\sin(2\cdot Ps)\cdot Sr2\end{array}\right]$$

$$a_{10}=(1-\alpha_A)\cdot\left[\begin{array}{l}\beta D\cdot\cos(2\cdot D-2\cdot As)+\beta D\cdot\cos(2\cdot D-2\cdot As)\cdot\alpha_P-\cos(2\cdot As)\cdot\cos(2\cdot\psi)\ldots+\\ -\cos(2\cdot As)\cdot\cos(2\cdot\psi)\cdot\alpha_P-\gamma_{Pp}\cdot\beta D\cdot\cos(2\cdot D-2\cdot As)\cdot\cos(2\cdot\psi)\cdot\cos(2\cdot Ps)\cdot Sr1\ldots+\\ -\gamma_{Pp}\cdot\beta D\cdot\cos(2\cdot D-2\cdot As)\cdot\cos(2\cdot\psi)\cdot\sin(2\cdot Ps)\cdot Sr2+\gamma_{Pp}\cdot\cos(2\cdot As)\cdot\cos(2\cdot Ps)\cdot Sr1\ldots+\\ \gamma_{Pp}\cdot\cos(2\cdot As)\cdot\sin(2\cdot Ps)\cdot Sr2+\sin(2\cdot As)\cdot\sin(2\cdot\psi)\cdot\cos(\Delta)\cdot\gamma_{Pp}\cdot\sin(2\cdot Ps)\cdot Sr1\ldots+\\ -\sin(2\cdot As)\cdot\sin(2\cdot\psi)\cdot\cos(\Delta)\cdot\gamma_{Pp}\cdot\cos(2\cdot Ps)\cdot Sr2-2\cdot\sin(2\cdot As)\cdot\sin(2\cdot\psi)\cdot\sin(\Delta)\cdot\sqrt{\alpha_P}\ \cdot Sr3\end{array}\right]$$

$$a_{11}=(1-\alpha_A)\cdot(1-\alpha_P)\cdot\left(\begin{array}{l}Sr1\cdot\beta D\cdot\cos(2\cdot D-2\cdot As)-Sr1\cdot\cos(2\cdot As)\cdot\cos(2\cdot\psi)\ldots+\\ -\cos(2\cdot Ps)\cdot\beta D\cdot\cos(2\cdot D-2\cdot As)\cdot\cos(2\cdot\psi)\ldots+\\ \cos(2\cdot Ps)\cdot\cos(2\cdot As)+\sin(2\cdot As)\cdot\sin(2\cdot\psi)\cdot\cos(\Delta)\cdot\sin(2\cdot Ps)\end{array}\right)$$

$$a_{12}=-(1-\alpha_P)\cdot(1-\alpha_A)\cdot\left(\begin{array}{l}Sr2\cdot\beta D\cdot\cos(2\cdot D-2\cdot As)-Sr2\cdot\cos(2\cdot As)\cdot\cos(2\cdot\psi)\ldots+\\ -\sin(2\cdot Ps)\cdot\beta D\cdot\cos(2\cdot D-2\cdot As)\cdot\cos(2\cdot\psi)\ldots+\\ \sin(2\cdot Ps)\cdot\cos(2\cdot As)-\sin(2\cdot As)\cdot\sin(2\cdot\psi)\cdot\cos(\Delta)\cdot\cos(2\cdot Ps)\end{array}\right)$$

$$a_{13}=(1-\alpha_A)\cdot\gamma_{Pn}\cdot\left[\begin{array}{l}-\beta D\cdot\cos(2\cdot D-2\cdot As)\cdot\cos(2\cdot\psi)\cdot\cos(2\cdot Ps)\cdot Sr1\ldots+\\ \beta D\cdot\cos(2\cdot D-2\cdot As)\cdot\cos(2\cdot\psi)\cdot\cos(2\cdot Ps)\cdot Sr2\ldots+\\ \cos(2\cdot As)\cdot\cos(2\cdot Ps)\cdot Sr1-\cos(2\cdot As)\cdot\sin(2\cdot Ps)\cdot Sr2\ldots+\\ \sin(2\cdot As)\cdot\sin(2\cdot\psi)\cdot\cos(\Delta)\cdot\sin(2\cdot Ps)\cdot Sr1\ldots+\\ \sin(2\cdot As)\cdot\sin(2\cdot\psi)\cdot\cos(\Delta)\cdot\cos(2\cdot Ps)\cdot Sr2\end{array}\right]$$

$$a_{14}=(1-\alpha_A)\cdot-\gamma_{Pn}\cdot\left[\begin{array}{l}-\beta D\cdot\cos(2\cdot D-2\cdot As)\cdot\cos(2\cdot\psi)\cdot\sin(2\cdot Ps)\cdot Sr1\ldots+\\ -\beta D\cdot\cos(2\cdot D-2\cdot As)\cdot\cos(2\cdot\psi)\cdot\cos(2\cdot Ps)\cdot Sr2\ldots+\\ \cos(2\cdot As)\cdot\sin(2\cdot Ps)\cdot Sr1+\cos(2\cdot As)\cdot\cos(2\cdot Ps)\cdot Sr2\ldots+\\ -\sin(2\cdot As)\cdot\sin(2\cdot\psi)\cdot\cos(\Delta)\cdot\cos(2\cdot Ps)\cdot Sr1\ldots+\\ \sin(2\cdot As)\cdot\sin(2\cdot\psi)\cdot\cos(\Delta)\cdot\sin(2\cdot Ps)\cdot Sr2\end{array}\right]$$

-continued
Rotating Polaizer/Rotating Analyzer $$a_{20} = -(1-\alpha_A) \cdot \begin{bmatrix} -\beta D \cdot \sin(2 \cdot D - 2 \cdot As) - \beta D \cdot \sin(2 \cdot D - 2 \cdot As) \cdot \alpha_P - \sin(2 \cdot As) \cdot \cos(2 \cdot \psi) \ldots + \\ -\sin(2 \cdot As) \cdot \cos(2 \cdot \psi) \cdot \alpha_P + \gamma_{Pp} \cdot \beta D \cdot \sin(2 \cdot D - 2 \cdot As) \cdot \cos(2 \cdot \psi) \cdot \cos(2 \cdot Ps) \cdot Sr1 \ldots + \\ \gamma_{Pp} \cdot \beta D \cdot \sin(2 \cdot D - 2 \cdot As) \cdot \cos(2 \cdot \psi) \cdot \sin(2 \cdot Ps) \cdot Sr2 + \gamma_{Pp} \cdot \sin(2 \cdot As) \cdot \cos(2 \cdot Ps) \cdot Sr1 \ldots + \\ \gamma_{Pp} \cdot \sin(2 \cdot As) \cdot \sin(2 \cdot Ps) \cdot Sr2 - \cos(2 \cdot As) \cdot \sin(2 \cdot \psi) \cdot \cos(\Delta) \cdot \gamma_{Pp} \cdot \sin(2 \cdot Ps) \cdot Sr1 \ldots + \\ \cos(2 \cdot As) \cdot \sin(2 \cdot \psi) \cdot \cos(\Delta) \cdot \gamma_{Pp} \cdot \cos(2 \cdot Ps) \cdot Sr2 + 2 \cdot \cos(2 \cdot As) \cdot \sin(2 \cdot \psi) \cdot \sin(\Delta) \cdot \sqrt{\alpha_P} \cdot Sr3 \end{bmatrix}$$

$$a_{21} = -(1-\alpha_A) \cdot (1-\alpha_P) \cdot \begin{pmatrix} -Sr1 \cdot \beta D \cdot \sin(2 \cdot D - 2 \cdot As) - Sr1 \cdot \sin(2 \cdot As) \cdot \cos(2 \cdot \psi) \ldots + \\ \cos(2 \cdot Ps) \cdot \beta D \cdot \sin(2 \cdot D - 2 \cdot As) \cdot \cos(2 \cdot \psi) \ldots + \\ \cos(2 \cdot Ps) \cdot \sin(2 \cdot As) - \cos(2 \cdot As) \cdot \sin(2 \cdot \psi) \cdot \cos(\Delta) \cdot \sin(2 \cdot Ps) \end{pmatrix}$$

$$a_{22} = (-1+\alpha_A) \cdot (-1+\alpha_P) \cdot \begin{pmatrix} -Sr2 \cdot \beta D \cdot \sin(2 \cdot D - 2 \cdot As) - Sr2 \cdot \sin(2 \cdot As) \cdot \cos(2 \cdot \psi) \ldots + \\ \sin(2 \cdot Ps) \cdot \beta D \cdot \sin(2 \cdot D - 2 \cdot As) \cdot \cos(2 \cdot \psi) \ldots + \\ \sin(2 \cdot Ps) \cdot \sin(2 \cdot As) + \cos(2 \cdot As) \cdot \sin(2 \cdot \psi) \cdot \cos(\Delta) \cdot \cos(2 \cdot Ps) \end{pmatrix}$$

$$a_{23} = (-1+\alpha_A) \cdot \gamma_{Pn} \cdot \begin{pmatrix} \beta D \cdot \sin(2 \cdot D - 2 \cdot As) \cdot \cos(2 \cdot \psi) \cdot \cos(2 \cdot Ps) \cdot Sr1 - \beta D \cdot \sin(2 \cdot D - 2 \cdot As) \cdot \cos(2 \cdot \psi) \cdot \sin(2 \cdot Ps) \cdot Sr2 \ldots + \\ \sin(2 \cdot As) \cdot \cos(2 \cdot Ps) \cdot Sr1 - \sin(2 \cdot As) \cdot \sin(2 \cdot Ps) \cdot Sr2 \ldots + \\ -\cos(2 \cdot As) \cdot \sin(2 \cdot \psi) \cdot \cos(\Delta) \cdot \sin(2 \cdot Ps) \cdot Sr1 \ldots + -\cos(2 \cdot As) \cdot \sin(2 \cdot \psi) \cdot \cos(\Delta) \cdot \cos(2 \cdot Ps) \cdot Sr2 \end{pmatrix}$$

$$a_{24} = -(-1+\alpha_A) \cdot \gamma_{Pn} \cdot \begin{pmatrix} \beta D \cdot \sin(2 \cdot D - 2 \cdot As) \cdot \cos(2 \cdot \psi) \cdot \sin(2 \cdot Ps) \cdot Sr1 + \beta D \cdot \sin(2 \cdot D - 2 \cdot As) \cdot \cos(2 \cdot \psi) \cdot \cos(2 \cdot Ps) \cdot Sr2 \ldots + \\ \sin(2 \cdot As) \cdot \sin(2 \cdot Ps) \cdot Sr1 + \sin(2 \cdot As) \cdot \cos(2 \cdot Ps) \cdot Sr2 \ldots + \\ \cos(2 \cdot As) \cdot \sin(2 \cdot \psi) \cdot \cos(\Delta) \cdot \cos(2 \cdot Ps) \cdot Sr1 \ldots + -\cos(2 \cdot As) \cdot \sin(2 \cdot \psi) \cdot \cos(\Delta) \cdot \sin(2 \cdot Ps) \cdot Sr2 \end{pmatrix}$$

$$a_{30} = \beta D \cdot \gamma_{An} \cdot \begin{bmatrix} -\cos(2 \cdot D - 4 \cdot As) \cdot \cos(2 \cdot \psi) - \cos(2 \cdot D - 4 \cdot As) \cdot \cos(2 \cdot \psi) \cdot \alpha_P \ldots + \\ \cos(2 \cdot D - 4 \cdot As) \cdot \gamma_{Pp} \cdot \cos(2 \cdot Ps) \cdot Sr1 + \cos(2 \cdot D - 4 \cdot As) \cdot \gamma_{Pp} \cdot \sin(2 \cdot Ps) \cdot Sr2 \ldots + \\ -\sin(2 \cdot D - 4 \cdot As) \cdot \sin(2 \cdot \psi) \cdot \cos(\Delta) \cdot \gamma_{Pp} \cdot \sin(2 \cdot Ps) \cdot Sr1 \ldots + \\ \sin(2 \cdot D - 4 \cdot As) \cdot \sin(2 \cdot \psi) \cdot \cos(\Delta) \cdot \gamma_{Pp} \cdot \cos(2 \cdot Ps) \cdot Sr2 \ldots + \\ 2 \cdot \sin(2 \cdot D - 4 \cdot As) \cdot \sin(2 \cdot \psi) \cdot \sin(\Delta) \cdot \sqrt{\alpha_P} \cdot Sr3 \end{bmatrix}$$

$$a_{31} = \beta D \cdot \gamma_{An} \cdot (1-\alpha_P) \cdot \begin{pmatrix} -\cos(2 \cdot D - 4 \cdot As) \cdot \cos(2 \cdot \psi) \cdot Sr1 + \cos(2 \cdot D - 4 \cdot As) \cdot \cos(2 \cdot Ps) \ldots + \\ -\sin(2 \cdot D - 4 \cdot As) \cdot \sin(2 \cdot \psi) \cdot \cos(\Delta) \cdot \sin(2 \cdot Ps) \end{pmatrix}$$

$$a_{32} = \beta D \cdot \gamma_{An} \cdot (-1+\alpha_P) \cdot \begin{pmatrix} -\cos(2 \cdot D - 4 \cdot As) \cdot \cos(2 \cdot \psi) \cdot Sr2 + \cos(2 \cdot D - 4 \cdot As) \cdot \sin(2 \cdot Ps) \ldots + \\ \sin(2 \cdot D - 4 \cdot As) \cdot \sin(2 \cdot \psi) \cdot \cos(\Delta) \cdot \cos(2 \cdot Ps) \end{pmatrix}$$

$$a_{33} = \beta D \cdot \gamma_{An} \cdot \gamma_{Pn} \cdot \begin{pmatrix} \cos(2 \cdot D - 4 \cdot As) \cdot \cos(2 \cdot Ps) \cdot Sr1 - \cos(2 \cdot D - 4 \cdot As) \cdot \sin(2 \cdot Ps) \cdot Sr2 \ldots + \\ -\sin(2 \cdot D - 4 \cdot As) \cdot \sin(2 \cdot \psi) \cdot \cos(\Delta) \cdot \sin(2 \cdot Ps) \cdot Sr1 \ldots + \\ -\sin(2 \cdot D - 4 \cdot As) \cdot \sin(2 \cdot \psi) \cdot \cos(\Delta) \cdot \cos(2 \cdot Ps) \cdot Sr2 \end{pmatrix}$$

$$a_{34} = -\beta D \cdot \gamma_{An} \cdot \gamma_{Pn} \cdot \begin{pmatrix} \cos(2 \cdot D - 4 \cdot As) \cdot \sin(2 \cdot Ps) \cdot Sr1 + \cos(2 \cdot D - 4 \cdot As) \cdot \cos(2 \cdot Ps) \cdot Sr2 \ldots + \\ \sin(2 \cdot D - 4 \cdot As) \cdot \sin(2 \cdot \psi) \cdot \cos(\Delta) \cdot \cos(2 \cdot Ps) \cdot Sr1 \ldots + \\ -\sin(2 \cdot D - 4 \cdot As) \cdot \sin(2 \cdot \psi) \cdot \cos(\Delta) \cdot \sin(2 \cdot Ps) \cdot Sr2 \end{pmatrix}$$

$$a_{40} = -\beta D \cdot \gamma_{An} \cdot \begin{bmatrix} \sin(2 \cdot D - 4 \cdot As) \cdot \cos(2 \cdot \psi) + \sin(2 \cdot D - 4 \cdot As) \cdot \cos(2 \cdot \psi) \cdot \alpha_P - \sin(2 \cdot D - 4 \cdot As) \cdot \gamma_{Pp} \cdot \cos(2 \cdot Ps) \cdot Sr1 \ldots + \\ -\sin(2 \cdot D - 4 \cdot As) \cdot \gamma_{Pp} \cdot \sin(2 \cdot Ps) \cdot Sr2 - \cos(2 \cdot D - 4 \cdot As) \cdot \sin(2 \cdot \psi) \cdot \cos(\Delta) \cdot \gamma_{Pp} \cdot \sin(2 \cdot Ps) \cdot Sr1 \ldots + \\ \cos(2 \cdot D - 4 \cdot As) \cdot \sin(2 \cdot \psi) \cdot \cos(\Delta) \cdot \gamma_{Pp} \cdot \cos(2 \cdot Ps) \cdot Sr2 \ldots + 2 \cdot \cos(2 \cdot D - 4 \cdot As) \cdot \sin(2 \cdot \psi) \cdot \sin(\Delta) \cdot \sqrt{\alpha_P} \cdot Sr3 \end{bmatrix}$$

$$a_{41} = -\beta D \cdot \gamma_{An} \cdot (1-\alpha_P) \cdot \begin{pmatrix} \sin(2 \cdot D - 4 \cdot As) \cdot \cos(2 \cdot \psi) \cdot Sr1 - \sin(2 \cdot D - 4 \cdot As) \cdot \cos(2 \cdot Ps) \ldots + \\ -\cos(2 \cdot D - 4 \cdot As) \cdot \sin(2 \cdot \psi) \cdot \cos(\Delta) \cdot \sin(2 \cdot Ps) \end{pmatrix}$$

$$a_{42} = -\beta D \cdot \gamma_{An} \cdot (-1+\alpha_P) \cdot \begin{pmatrix} \sin(2 \cdot D - 4 \cdot As) \cdot \cos(2 \cdot \psi) \cdot Sr2 - \sin(2 \cdot D - 4 \cdot As) \cdot \sin(2 \cdot Ps) \ldots + \\ \cos(2 \cdot D - 4 \cdot As) \cdot \sin(2 \cdot \psi) \cdot \cos(\Delta) \cdot \cos(2 \cdot Ps) \end{pmatrix}$$

$$a_{43} = -\beta D \cdot \gamma_{An} \cdot \gamma_{Pn} \cdot \begin{pmatrix} -\sin(2 \cdot D - 4 \cdot As) \cdot \cos(2 \cdot Ps) \cdot Sr1 + \sin(2 \cdot D - 4 \cdot As) \cdot \sin(2 \cdot Ps) \cdot Sr2 \ldots + \\ -\cos(2 \cdot D - 4 \cdot As) \cdot \sin(2 \cdot \psi) \cdot \cos(\Delta) \cdot \sin(2 \cdot Ps) \cdot Sr1 \ldots + \\ -\cos(2 \cdot D - 4 \cdot As) \cdot \sin(2 \cdot \psi) \cdot \cos(\Delta) \cdot \cos(2 \cdot Ps) \cdot Sr2 \end{pmatrix}$$

$$a_{44} = \beta D \cdot \gamma_{An} \cdot \gamma_{Pn} \cdot \begin{pmatrix} -\sin(2 \cdot D - 4 \cdot As) \cdot \sin(2 \cdot Ps) \cdot Sr1 - \sin(2 \cdot D - 4 \cdot As) \cdot \cos(2 \cdot Ps) \cdot Sr2 \ldots + \\ \cos(2 \cdot D - 4 \cdot As) \cdot \sin(2 \cdot \psi) \cdot \cos(\Delta) \cdot \cos(2 \cdot Ps) \cdot Sr1 \ldots + \\ -\cos(2 \cdot D - 4 \cdot As) \cdot \sin(2 \cdot \psi) \cdot \cos(\Delta) \cdot \sin(2 \cdot Ps) \cdot Sr2 \end{pmatrix}$$

FOR ROTATING POLARIZER AND ROTATING COMPENSATOR CALIBRATION PROCEDURE (RPRC)

The method of Calibrating for Non-Idealities in Mathematical Representations of Rotated and Non-Rotated Components of a Sample System Investigating System described directly is applicable to Ellipsometers and Polarimeters which are sequentially comprised of a Source of a Beam of Electromagnetic wavelengths, a Polarizer means, typically for imposing a state of polarization upon said Beam of Electromagnetic wavelengths, a Stage for supporting a Sample System, an Analyzer means, typically for selecting a state of polarization in said Beam of Electromagnetic wavelengths and a Detector System. In addition, the Sample System Investigating System is further comprised of at least a First Compensator means, said at least a First Compensator means being positioned in said Sample System Investigating System at a location selected from the group consisting of, before and after, said Stage for supporting said Sample System. The Sample System Investigating System can also optionally comprise a Second Compensator means positioned in said Sample System Investigating System at a location complementary to said First Compensator means, said position being selected from the group consisting of, respectively, after and before, said Stage for supporting said Sample System.

An exemplary (RPRC) Calibration Method comprises the steps of:

Step a. Empirically obtaining at least two Data Sets, each of which Data Sets consists of Intensity Values measured by said Detector system, said Intensity values being a function of settings of Azimuthal angles of said Polarizer means and one said Compensator means of said Sample System Investigating System. One of said Data sets being obtained with said Sample System Investigating System oriented in a "Sample-Present" configuration, and one of said Data being obtained with said Sample System Investigating System oriented in a configuration selected from the group consisting of "Alternative Sample-Present" and "Straight-Through" Which "Straight-Through" configuration results from orienting said Sample System Investigating System such that a Beam of Electromagnetic wavelengths provided by said Source of a Beam of Electromagnetic wavelengths is caused to pass through said Polarization means, through said Analyzer means and into said Detector system. And which "Sample Present" configuration results from orienting said Sample System Investigating System such that a Beam of Electromagnetic wavelengths provided by said Source of a Beam of Electromagnetic wavelengths is caused to pass through said Polarization means, interact with an Arbitrary Sample System supported by said Stage for supporting a Sample System, pass through said Analyzer means and into said Detector system. In either of said "Straight Through" or "Sample Present" configurations of said Sample System investigating system, said Beam of Electromagnetic wavelengths is also caused to pass through present Compensator means.

Step b. Applying mathematical formula to said Data Sets to provide Empirically derived Numerical Values for Coefficients of Two-Dimensional Mathematical Series, said Dimension of said Two-Dimensional Mathematical Series being determined by the number of Sample System Investigating System components, namely the Polarizer means and Compensator means, which were caused to assume various Azimuthal Angle settings during the obtaining of Data Sets in step a.

Step c. Effectively deriving Analytical Non-Ideality Compensating Calibration Parameter containing Equations for Two-Dimensional Mathematical Series Coefficients, each of which effective Analytically Derived Non-Ideality Compensation Calibration Parameter containing Equations for Two-Dimensional Mathematical Series Coefficients is analogically equivalent to Numerical Values for corresponding Two-Dimensional Mathematical Series Coefficients Empirically determined by applying Mathematical Formula to the Data Sets as in Step b. Said analogically equivalent Non-Ideality Compensating Calibration Parameter containing Equations for Two-Dimensional Mathematical Series Coefficients being provided by, for instance, performing Matrix Multiplication of Non-Ideality Compensating Calibration Parameter containing Matrices which represent Sample System Investigating System components and Rotation Matrices, each thereof being oriented in a series of said Sample System Investigating System component and Rotation Matrices to appropriately represent a "Straight-Through" or a "Sample Present" configuration of said Sample System investigating system.

Step d. Performing a simultaneous Mathematical Regression of Step c., Analytically arrived at Non-Ideality Compensating Calibration Parameter containing Equation for Coefficients of Two-Dimensional Mathematical series, onto analogically equivalent Numerical Value for Two-Dimensional Mathematical Series Coefficients as arrived at in Step b.

The result being that each Non-Ideality Compensating Calibration Parameters in said effective Non-Ideality Compensating Calibration Parameter containing Equations for Two-Dimensional Mathematical Series Coefficients are simultaneously Evaluated, based upon an error reducing criteria. Said Non-Ideality Compensating Calibration Parameters being for said Source of a Beam of Electromagnetic wavelengths, said Polarizer means, said Compensator Means, and for a Lumped combination of said Analyzer means and said Detector system, with the Arbitrary Sample System Characterization (PSI & DELTA) also being provided.

Following directly are Print-Outs showing specific Calibration Parameter Containing Equations which analogically correspond the to Empirically Determined Numerical Values for the Double Fourier Series Matrix Elements, (ie. Coefficients), which Calibration Parameter Containing Equations are Regressed onto said Matrix Element Numerical Values to simultaneously provide Numerical Values for each Calibration Parameter.

In this (RPRC) case, the following Calibration Parameters are simultaneously evaluated:

| | Print-Out Symbol |
|---|---|
| Source: | |
| S0 (not present as normalization basis for S1, S2 and S3) | |
| S1 | Sr1 |
| S2 | Sr2 |
| S3 | Sr3 |
| Polarizer: | |
| ALPHAp | αp |

-continued

| | Print-Out Symbol |
|---|---|
| Sample System: | |
| PSIs | $\psi$ |
| DELTAs | $\delta$ |
| Compensator: | |
| PSIc | $\psi c$ |
| DELTAc | $\delta c$ |
| Lumped Analyzer and Detector: | |
| A0 (not present as normalization basis for A1 & A2) | |
| A1 | A1 |
| A2 | A2 |
| A3 (is equal to zero (0.0)) | |

-continued

| | Print-Out Symbol |
|---|---|
| Rotation Angles: | |
| Rotation Azimuthal Angle to Compensator | Cs |
| Rotation Azimuthal Angle to Polarizer | Ps |

(Note it typically is not necessary to distinguish the Lumped Analyzer and Detector as the Lumped Calibration Parameter Values do not involve the Sample System. Also note that a similar print-out could be achieved for a (RARC) scenario wherein symetry between the Lumped Source and Analyzer in the (RPRC) scenario analogically corresponds to that between the Lumped Polarizer and Detector in the (RARC) scenario, for instance. Said print-out is not provided).

Rotating Polarizer/Rotating Compensator $$\gamma_{P_p} = \frac{(1+\sqrt{\alpha_P})^2}{2} \quad \gamma_{P_n} = \frac{(1+\sqrt{\alpha_P})^2}{2}$$

$$q = 1 + \sin(2\cdot\psi_c)\cdot\cos(\delta_c) \quad r = \sin(2\cdot\psi_c)\cdot\sin(\delta_c) \quad s = \cos(2\cdot\psi_c)$$

$$\begin{aligned}
a_{00} = {} & 1 + \alpha_p - \frac{1}{2}\cdot\cos(2\cdot\psi)\cdot A1\cdot q\cdot\cos(2\cdot Cs) - \frac{1}{2}\cdot\cos(2\cdot\psi)\cdot A1\cdot q\cdot\cos(2\cdot Cs)\cdot\alpha_p - \frac{1}{2}\cdot \\
& \cos(2\cdot\psi)\cdot A2\cdot q\cdot\sin(2\cdot Cs)\ldots + -\frac{1}{2}\cdot\cos(2\cdot\psi)\cdot A2\cdot q\cdot\sin(2\cdot Cs)\cdot\alpha_P - \gamma_{P_p}\cdot \\
& \cos(2\cdot\psi)\cdot\cos(2\cdot Ps)\cdot Sr1 - \gamma_{P_p}\cdot\cos(2\cdot\psi)\cdot\sin(2\cdot Ps)\cdot Sr2\ldots + \frac{1}{2}\cdot\gamma_{P_p}\cdot A1\cdot q\cdot \\
& \cos(2\cdot Cs)\cdot\cos(2\cdot Ps)\cdot Sr1 + \frac{1}{2}\cdot\gamma_{P_p}\cdot A1\cdot q\cdot\cos(2\cdot Cs)\cdot\sin(2\cdot Ps)\cdot Sr2\ldots + \\
& \frac{1}{2}\cdot\gamma_{P_p}\cdot A2\cdot q\cdot\sin(2\cdot Cs)\cdot\cos(2\cdot Ps)\cdot Sr1\ldots + \frac{1}{2}\gamma_{P_p}\cdot A2\cdot q\cdot\sin(2\cdot Cs)\cdot \\
& \sin(2\cdot Ps)\cdot Sr2 + \frac{1}{2}\cdot q\cdot\sin(2\cdot\psi)\cdot\cos(\Delta)\cdot\gamma_{P_p}\cdot A1\cdot\sin(2\cdot Cs)\cdot\sin(2\cdot Ps)\cdot \\
& Sr1\ldots + -\frac{1}{2}\cdot q\cdot\sin(2\cdot\psi)\cdot\cos(\Delta)\cdot\gamma_{P_p}\cdot A1\cdot\sin(2\cdot Cs)\cdot\cos(2\cdot Ps)\cdot Sr2\ldots + \\
& \frac{-1}{2}\cdot q\cdot\sin(2\cdot\psi)\cdot\cos(\Delta)\cdot\gamma_{P_p}\cdot A2\cdot\cos(2\cdot Cs)\cdot\sin(2\cdot Ps)\cdot Sr1\ldots + \frac{1}{2}\cdot q\cdot \\
& \sin(2\cdot\psi)\cdot\cos(\Delta)\cdot\gamma_{P_p}\cdot A2\cdot\cos(2\cdot Cs)\cdot\cos(2\cdot Ps)\cdot Sr2 - q\cdot\sin(2\cdot\psi)\cdot\sin(\Delta)\cdot \\
& \sqrt{\alpha_p}\cdot Sr3\cdot A1\cdot\sin(2\cdot Cs)\ldots + q\cdot\sin(2\cdot\psi)\cdot\sin(\Delta)\cdot\sqrt{\alpha_p}\cdot Sr3\cdot A2\cdot\cos(2\cdot Cs)
\end{aligned}$$

$$a_{01} = (1-\alpha_p)\cdot\begin{bmatrix} Sr1 - \frac{1}{2}\cdot Sr1\cdot\cos(2\cdot\psi)\cdot A1\cdot q\cdot\cos(2\cdot Cs) - \frac{1}{2}\cdot Sr1\cdot\cos(2\cdot\psi)\cdot A2\cdot q\cdot\sin(2\cdot Cs) - \\ \cos(2\cdot Ps)\cdot\cos(2\cdot\psi)\ldots + \frac{1}{2}\cdot\cos(2\cdot Ps)\cdot A1\cdot q\cdot\cos(2\cdot Cs) + \frac{1}{2}\cdot\cos(2\cdot Ps)\cdot \\ A2\cdot q\cdot\sin(2\cdot Cs)\ldots + \frac{1}{2}\cdot q\cdot\sin(2\cdot\psi)\cdot\cos(\Delta)\cdot\sin(2\cdot Ps)\cdot A1\cdot\sin(2\cdot Cs)\ldots + -\frac{1}{2}\cdot \\ q\cdot\sin(2\cdot\psi)\cdot\cos(\Delta)\cdot\sin(2\cdot Ps)\cdot A2\cdot\cos(2\cdot Cs) \end{bmatrix}$$

$$a_{02} = -(1-\alpha_p)\cdot\begin{bmatrix} Sr2 - \frac{1}{2}\cdot Sr2\cdot\cos(2\cdot\psi)\cdot A1\cdot q\cdot\cos(2\cdot Cs) - \frac{1}{2}\cdot Sr2\cdot\cos(2\cdot\psi)\cdot A2\cdot q\cdot\sin(2\cdot Cs) - \\ \sin(2\cdot Ps)\cdot\cos(2\cdot\psi)\ldots + \frac{1}{2}\cdot\sin(2\cdot Ps)\cdot A1\cdot q\cdot\cos(2\cdot Cs) + \frac{1}{2}\cdot\sin(2\cdot Ps)\cdot \\ A2\cdot q\cdot\sin(2\cdot Cs)\ldots + \frac{1}{2}\cdot q\cdot\sin(2\cdot\psi)\cdot\cos(\Delta)\cdot\cos(2\cdot Ps)\cdot A1\cdot\sin(2\cdot Cs)\ldots + \frac{1}{2}\cdot \\ q\cdot\sin(2\cdot\psi)\cdot\cos(\Delta)\cdot\cos(2\cdot Ps)\cdot A2\cdot\cos(2\cdot Cs) \end{bmatrix}$$

-continued

Rotating Polarizer/Rotating Compensator $$a_{03}=\gamma_{P_n}\cdot\begin{bmatrix}-\cos(2\cdot\psi)\cdot\cos(2\cdot Ps)\cdot Sr1+\cos(2\cdot\psi)\cdot\sin(2\cdot Ps)\cdot Sr2+\frac{1}{2}\cdot A1\cdot q\cdot\\ \cos(2\cdot Cs)\cdot\cos(2\cdot Ps)\cdot Sr1\ldots+\frac{-1}{2}\cdot A1\cdot q\cdot\cos(2\cdot Cs)\cdot\sin(2\cdot Ps)\cdot\\ Sr2+\frac{1}{2}\cdot A2\cdot q\cdot\sin(2\cdot Cs)\cdot\cos(2\cdot Ps)\cdot Sr1\ldots+\frac{-1}{2}\cdot A2\cdot q\cdot\\ \sin(2\cdot Cs)\cdot\sin(2\cdot Ps)\cdot Sr2+\frac{1}{2}\cdot q\cdot\sin(2\cdot\psi)\cdot\cos(\Delta)\cdot A1\cdot\sin(2\cdot Cs)\cdot\\ \sin(2\cdot Ps)\cdot Sr1\ldots+\frac{1}{2}\cdot q\cdot\sin(2\cdot\psi)\cdot\cos(\Delta)\cdot A1\cdot\sin(2\cdot Cs)\cdot\cos(2\cdot Ps)\cdot\\ Sr2-\frac{1}{2}\cdot q\cdot\sin(2\cdot\psi)\cdot\cos(\Delta)\cdot A2\cdot\cos(2\cdot Cs)\cdot\sin(2\cdot Ps)\cdot Sr1\ldots+-\frac{1}{2}\cdot\\ q\cdot\sin(2\cdot\psi)\cdot\cos(\Delta)\cdot A2\cdot\cos(2\cdot Cs)\cdot\cos(2\cdot Ps)\cdot Sr2\end{bmatrix}$$

$$a_{04}=-\gamma_{P_n}\cdot\begin{bmatrix}-\cos(2\cdot\psi)\cdot\sin(2\cdot Ps)\cdot Sr1-\cos(2\cdot\psi)\cdot\cos(2\cdot Ps)\cdot Sr2+\frac{1}{2}\cdot A1\cdot q\cdot\\ \cos(2\cdot Cs)\cdot\sin(2\cdot Ps)\cdot Sr1\ldots+\frac{1}{2}\cdot A1\cdot q\cdot\cos(2\cdot Cs)\cdot\cos(2\cdot Ps)\cdot\\ Sr2+\frac{1}{2}\cdot A2\cdot q\cdot\sin(2\cdot Cs)\cdot\sin(2\cdot Ps)\cdot Sr1\ldots+\frac{1}{2}\cdot A2\cdot q\cdot\\ \sin(2\cdot Cs)\cdot\cos(2\cdot Ps)\cdot Sr2-\frac{1}{2}\cdot q\cdot\sin(2\cdot\psi)\cdot\cos(\Delta)\cdot A1\cdot\sin(2\cdot Cs)\cdot\\ \cos(2\cdot Ps)\cdot Sr1\ldots+\frac{1}{2}\cdot q\cdot\sin(2\cdot\psi)\cdot\cos(\Delta)\cdot A1\cdot\sin(2\cdot Cs)\cdot\sin(2\cdot Ps)\cdot\\ Sr2+\frac{1}{2}\cdot q\cdot\sin(2\cdot\psi)\cdot\cos(\Delta)\cdot A2\cdot\cos(2\cdot Cs)\cdot\cos(2\cdot Ps)\cdot Sr1\ldots+-\frac{1}{2}\cdot\\ q\cdot\sin(2\cdot\psi)\cdot\cos(\Delta)\cdot A2\cdot\cos(2\cdot Cs)\cdot\sin(2\cdot Ps)\cdot Sr2\end{bmatrix}$$

$$\begin{aligned}a_{10}=\;&-A1\cdot s-A1\cdot s\cdot\alpha_p+s\cdot\cos(2\cdot Cs)\cdot\cos(2\cdot\psi)+s\cdot\cos(2\cdot Cs)\cdot\cos(2\cdot\psi)\cdot\alpha_p+\gamma_{P_p}\cdot A1\cdot\\ &s\cdot\cos(2\cdot\psi)\cdot\cos(2\cdot Ps)\cdot Sr1\ldots+\gamma_{P_p}\cdot A1\cdot s\cdot\cos(2\cdot\psi)\cdot\sin(2\cdot Ps)\cdot Sr2-\gamma_{P_p}\cdot s\cdot\cos(2\cdot Cs)\cdot\\ &\cos(2\cdot Ps)\cdot Sr1-\gamma_{P_p}\cdot s\cdot\cos(2\cdot Cs)\cdot\sin(2\cdot Ps)\cdot Sr2\ldots+-\gamma_{P_p}\cdot s\cdot\sin(2\cdot Cs)\cdot\sin(2\cdot\psi)\cdot\\ &\cos(\Delta)\cdot\sin(2\cdot Ps)\cdot Sr1+\gamma_{P_p}\cdot s\cdot\sin(2\cdot Cs)\cdot\sin(2\cdot\psi)\cdot\cos(\Delta)\cdot\cos(2\cdot Ps)\cdot Sr2\ldots+\gamma_{P_p}\cdot A2\cdot r\cdot\\ &\sin(2\cdot\psi)\cdot\sin(\Delta)\cdot\sin(2\cdot Ps)\cdot Sr1-\gamma_{P_p}\cdot A2\cdot r\cdot\sin(2\cdot\psi)\cdot\sin(\Delta)\cdot\cos(2\cdot Ps)\cdot Sr2\ldots+2\cdot\\ &\sqrt{\alpha_p}\cdot Sr3\cdot s\cdot\sin(2\cdot Cs)\cdot\sin(2\cdot\psi)\cdot\sin(\Delta)+2\cdot\sqrt{\alpha_p}\cdot Sr3\cdot A2\cdot r\cdot\sin(2\cdot\psi)\cdot\cos(\Delta)\end{aligned}$$

$$a_{11}=(1-\alpha_p)\cdot\begin{pmatrix}-Sr1\cdot A1\cdot s+Sr1\cdot s\cdot\cos(2\cdot Cs)\cdot\cos(2\cdot\psi)+\cos(2\cdot Ps)\cdot A1\cdot s\cdot\cos(2\cdot\psi)-\cos(2\cdot Ps)\cdot\\ s\cdot\cos(2\cdot Cs)\ldots+-\sin(2\cdot Ps)\cdot s\cdot\sin(2\cdot Cs)\cdot\sin(2\cdot\psi)\cdot\cos(\Delta)+\sin(2\cdot Ps)\cdot A\,2\cdot r\cdot\\ \sin(2\cdot\psi)\cdot\sin(\Delta)\end{pmatrix}$$

$$a_{12}=-(1-\alpha_p)\cdot\begin{pmatrix}-Sr2\cdot A1\cdot s+Sr2\cdot s\cdot\cos(2\cdot Cs)\cdot\cos(2\cdot\psi)+\sin(2\cdot Ps)\cdot A1\cdot s\cdot\cos(2\cdot\psi)-\sin(2\cdot Ps)\cdot\\ s\cdot\cos(2\cdot Cs)\ldots+\cos(2\cdot Ps)\cdot s\cdot\sin(2\cdot Cs)\cdot\sin(2\cdot\psi)\cdot\cos(\Delta)-\cos(2\cdot Ps)\cdot A\,2\cdot r\cdot\\ \sin(2\cdot\psi)\cdot\sin(\Delta)\end{pmatrix}$$

$$a_{13}=\gamma_{P_n}\cdot\begin{pmatrix}A1\cdot s\cdot\cos(2\cdot\psi)\cdot\cos(2\cdot Ps)\cdot Sr1-A1\cdot s\cdot\cos(2\cdot\psi)\cdot\sin(2\cdot Ps)\cdot Sr2-s\cdot\cos(2\cdot Cs)\cdot\\ \cos(2\cdot Ps)\cdot Sr1\ldots+s\cdot\cos(2\cdot Cs)\cdot\sin(2\cdot Ps)\cdot Sr2\ldots+-s\cdot\sin(2\cdot Cs)\cdot\sin(2\cdot\psi)\cdot\cos(\Delta)\cdot\\ \sin(2\cdot Ps)\cdot Sr1-s\cdot\sin(2\cdot Cs)\cdot\sin(2\cdot\psi)\cdot\cos(\Delta)\cdot\cos(2\cdot Ps)\cdot Sr2\ldots+A2\cdot r\cdot\sin(2\cdot\psi)\cdot\\ \sin(\Delta)\cdot\sin(2\cdot Ps)\cdot Sr1+A2\cdot r\cdot\sin(2\cdot\psi)\cdot\sin(\Delta)\cdot\cos(2\cdot Ps)\cdot Sr2\end{pmatrix}$$

$$a_{14}=-\gamma_{P_n}\cdot\begin{pmatrix}A1\cdot s\cdot\cos(2\cdot\psi)\cdot\sin(2\cdot Ps)\cdot Sr1+A1\cdot s\cdot\cos(2\cdot\psi)\cdot\cos(2\cdot Ps)\cdot Sr2-s\cdot\cos(2\cdot Cs)\cdot\\ \sin(2\cdot Ps)\cdot Sr1\ldots+-s\cdot\cos(2\cdot Cs)\cdot\cos(2\cdot Ps)\cdot Sr2\ldots+s\cdot\sin(2\cdot Cs)\cdot\sin(2\cdot\psi)\cdot\cos(\Delta)\cdot\\ \cos(2\cdot Ps)\cdot Sr1-s\cdot\sin(2\cdot Cs)\cdot\sin(2\cdot\psi)\cdot\cos(\Delta)\cdot\sin(2\cdot Ps)\cdot Sr2\ldots+-A2\cdot r\cdot\sin(2\cdot\psi)\cdot\\ \sin(\Delta)\cdot\cos(2\cdot Ps)\cdot Sr1+A2\cdot r\cdot\sin(2\cdot\psi)\cdot\sin(\Delta)\cdot\sin(2\cdot Ps)\cdot Sr2\end{pmatrix}$$

$$\begin{aligned}a_{20}=\;&A2\cdot s+A2\cdot s\cdot\alpha_p-s\cdot\sin(2\cdot Cs)\cdot\cos(2\cdot\psi)-s\cdot\sin(2\cdot Cs)\cdot\cos(2\cdot\psi)\cdot\alpha_p+\gamma_{P_p}\cdot A2\cdot\\ &s\cdot\cos(2\cdot\psi)\cdot\cos(2\cdot Ps)\cdot Sr1\ldots+-\gamma_{P_p}\cdot A2\cdot s\cdot\cos(2\cdot\psi)\cdot\sin(2\cdot Ps)\cdot Sr2+\gamma_{P_p}\cdot s\cdot\sin(2\cdot Cs)\cdot\\ &\cos(2\cdot Ps)\cdot Sr1+\gamma_{P_p}\cdot s\cdot\sin(2\cdot Cs)\cdot\sin(2\cdot Ps)\cdot Sr2\ldots+-\gamma_{P_p}\cdot s\cdot\cos(2\cdot Cs)\cdot\sin(2\cdot\psi)\cdot\\ &\cos(\Delta)\cdot\sin(2\cdot Ps)\cdot Sr1+\gamma_{P_p}\cdot s\cdot\cos(2\cdot Cs)\cdot\sin(2\cdot\psi)\cdot\cos(\Delta)\cdot\cos(2\cdot Ps)\cdot Sr2\ldots+\gamma_{P_p}\cdot A1\cdot r\cdot\\ &\sin(2\cdot\psi)\cdot\sin(\Delta)\cdot\sin(2\cdot Ps)\cdot Sr1-\gamma_{P_p}\cdot A1\cdot r\cdot\sin(2\cdot\psi)\cdot\sin(\Delta)\cdot\cos(2\cdot Ps)\cdot Sr2\ldots+2\cdot\\ &\sqrt{\alpha_p}\cdot Sr3\cdot s\cdot\cos(2\cdot Cs)\cdot\sin(2\cdot\psi)\cdot\sin(\Delta)+2\cdot\sqrt{\alpha_p}\cdot Sr3\cdot A1\cdot r\cdot\sin(2\cdot\psi)\cdot\cos(\Delta)\end{aligned}$$

-continued

Rotating Polarizer/Rotating Compensator $$a_{21} = (1 - \alpha_p) \cdot \left( \begin{array}{l} Sr1 \cdot A2 \cdot s - Sr1 \cdot s \cdot \sin(2 \cdot Cs) \cdot \cos(2 \cdot \psi) - \cos(2 \cdot Ps) \cdot A2 \cdot s \cdot \cos(2 \cdot \psi) + \cos(2 \cdot Ps) \cdot \\ s \cdot \sin(2 \cdot Cs) \ldots + -\sin(2 \cdot Ps) \cdot s \cdot \cos(2 \cdot Cs) \cdot \sin(2 \cdot \psi) \cdot \cos(\Delta) + \sin(2 \cdot Ps) \cdot A1 \cdot r \cdot \\ \sin(2 \cdot \psi) \cdot \sin(\Delta) \end{array} \right)$$

$$a_{22} = -(1 - \alpha_p) \cdot \left( \begin{array}{l} Sr2 \cdot A2 \cdot s - Sr2 \cdot s \cdot \sin(2 \cdot Cs) \cdot \cos(2 \cdot \psi) - \sin(2 \cdot Ps) \cdot A2 \cdot s \cdot \cos(2 \cdot \psi) + \sin(2 \cdot Ps) \cdot \\ s \cdot \sin(2 \cdot Cs) \ldots + \cos(2 \cdot Ps) \cdot s \cdot \cos(2 \cdot Cs) \cdot \sin(2 \cdot \psi) \cdot \cos(\Delta) - \cos(2 \cdot Ps) \cdot A1 \cdot r \cdot \\ \sin(2 \cdot \psi) \cdot \sin(\Delta) \end{array} \right)$$

$$a_{23} = \gamma_{Pn} \cdot \left( \begin{array}{l} -A2 \cdot s \cdot \cos(2 \cdot \psi) \cdot \cos(2 \cdot Ps) \cdot Sr1 + A2 \cdot s \cdot \cos(2 \cdot \psi) \cdot \sin(2 \cdot Ps) \cdot Sr2 + s \cdot \sin(2 \cdot Cs) \cdot \\ \cos(2 \cdot Ps) \cdot Sr1 \ldots + -s \cdot \sin(2 \cdot Cs) \cdot \sin(2 \cdot Ps) \cdot Sr2 \ldots + -s \cdot \cos(2 \cdot Cs) \cdot \sin(2 \cdot \psi) \cdot \cos(\Delta) \cdot \\ \sin(2 \cdot Ps) \cdot Sr1 - s \cdot \cos(2 \cdot Cs) \cdot \sin(2 \cdot \psi) \cdot \cos(\Delta) \cdot \cos(2 \cdot Ps) \cdot Sr2 \ldots + A1 \cdot r \cdot \sin(2 \cdot \psi) \cdot \\ \sin(\Delta) \cdot \sin(2 \cdot Ps) \cdot Sr1 + A1 \cdot r \cdot \sin(2 \cdot \psi) \cdot \sin(\Delta) \cdot \cos(2 \cdot Ps) \cdot Sr2 \end{array} \right)$$

$$a_{24} = -\gamma_{Pn} \cdot \left( \begin{array}{l} -A2 \cdot s \cdot \cos(2 \cdot \psi) \cdot \sin(2 \cdot Ps) \cdot Sr1 - A2 \cdot s \cdot \cos(2 \cdot \psi) \cdot \cos(2 \cdot Ps) \cdot Sr2 + s \cdot \sin(2 \cdot Cs) \cdot \\ \sin(2 \cdot Ps) \cdot Sr1 \ldots + s \cdot \sin(2 \cdot Cs) \cdot \cos(2 \cdot Ps) \cdot Sr2 \ldots + s \cdot \cos(2 \cdot Cs) \cdot \sin(2 \cdot \psi) \cdot \cos(\Delta) \cdot \\ \cos(2 \cdot Ps) \cdot Sr1 - s \cdot \cos(2 \cdot Cs) \cdot \sin(2 \cdot \psi) \cdot \cos(\Delta) \cdot \sin(2 \cdot Ps) \cdot Sr2 \ldots + -A1 \cdot r \cdot \sin(2 \cdot \psi) \cdot \\ \sin(\Delta) \cdot \cos(2 \cdot Ps) \cdot Sr1 + A1 \cdot r \cdot \sin(2 \cdot \psi) \cdot \sin(\Delta) \cdot \sin(2 \cdot Ps) \cdot Sr2 \end{array} \right)$$

$$a_{30} = \frac{2 - q}{2} \cdot \left| \begin{array}{l} \cos(2 \cdot \psi) \cdot A2 \cdot \sin(2 \cdot Cs) + \cos(2 \cdot \psi) \cdot A2 \cdot \sin(2 \cdot Cs) \cdot \alpha_p - \cos(2 \cdot \psi) \cdot A1 \cdot \\ \cos(2 \cdot Cs) \ldots + -\cos(2 \cdot \psi) \cdot A1 \cdot \cos(2 \cdot Cs) \cdot \alpha_p - \gamma_{P_p} \cdot A2 \cdot \sin(2 \cdot Cs) \cdot \\ \cos(2 \cdot Ps) Sr1 \ldots + -\gamma_{P_p} \cdot A2 \cdot \sin(2 \cdot Cs) \cdot \sin(2 \cdot Ps) \cdot Sr2 + \gamma_{P_p} \cdot A1 \cdot \\ \cos(2 \cdot Cs) \cdot \cos(2 \cdot Ps) \cdot Sr1 \ldots + \gamma_{P_p} \cdot A1 \cdot \cos(2 \cdot Cs) \cdot \sin(2 \cdot Ps) \cdot \\ Sr2 + \sin(2 \cdot \psi) \cdot \cos(\Delta) \cdot \gamma_{P_p} \cdot A1 \cdot \sin(2 \cdot Cs) \cdot \sin(2 \cdot Ps) \cdot Sr1 \ldots + -\sin(2 \cdot \psi) \cdot \\ \cos(\Delta) \cdot \gamma_{P_p} \cdot A1 \cdot \sin(2 \cdot Cs) \cdot \cos(2 \cdot Ps) \cdot Sr2 \ldots + \sin(2 \cdot \psi) \cdot \cos(\Delta) \cdot \\ \gamma_{P_p} \cdot A2 \cdot \cos(2 \cdot Cs) \cdot \sin(2 \cdot Ps) \cdot Sr1 \ldots + -\sin(2 \cdot \psi) \cdot \cos(\Delta) \cdot \gamma_{P_p} \cdot A2 \cdot \\ \cos(2 \cdot Cs) \cdot \cos(2 \cdot Ps) \cdot Sr2 - 2 \cdot \sin(2 \cdot \psi) \cdot \sin(\Delta) \cdot \sqrt{\alpha_p} \cdot Sr3 \cdot A1 \cdot \\ \sin(2 \cdot Cs) \ldots + -2 \cdot \sin(2 \cdot \psi) \cdot \sin(\Delta) \cdot \sqrt{\alpha_p} \cdot Sr3 \cdot A2 \cdot \cos(2 \cdot Cs) \end{array} \right|$$

$$a_{31} = \frac{2 - q}{2} \cdot (1 - \alpha_p) \cdot \left( \begin{array}{l} \cos(2 \cdot \psi) \cdot Sr1 \cdot A2 \cdot \sin(2 \cdot Cs) - \cos(2 \cdot \psi) \cdot Sr1 \cdot A1 \cdot \cos(2 \cdot Cs) - \cos(2 \cdot Ps) \cdot \\ A2 \cdot \sin(2 \cdot Cs) \ldots + \cos(2 \cdot Ps) \cdot A1 \cdot \cos(2 \cdot Cs) \ldots + \sin(2 \cdot \psi) \cdot \cos(\Delta) \cdot \\ \sin(2 \cdot Ps) \cdot A1 \cdot \sin(2 \cdot Cs) + \sin(2 \cdot \psi) \cdot \cos(\Delta) \cdot \sin(2 \cdot Ps) \cdot A2 \cdot \cos(2 \cdot Cs) \end{array} \right)$$

$$a_{32} = \frac{2 - q}{2} \cdot (1 - \alpha_p) \cdot \left( \begin{array}{l} \cos(2 \cdot \psi) \cdot Sr2 \cdot A2 \cdot \sin(2 \cdot Cs) - \cos(2 \cdot \psi) \cdot Sr2 \cdot A1 \cdot \cos(2 \cdot Cs) - \sin(2 \cdot Ps) \cdot \\ A2 \cdot \sin(2 \cdot Cs) \ldots + \sin(2 \cdot Ps) \cdot A1 \cdot \cos(2 \cdot Cs) \ldots + -\sin(2 \cdot \psi) \cdot \cos(\Delta) \cdot \\ \cos(2 \cdot Ps) \cdot A1 \cdot \sin(2 \cdot Cs) - \sin(2 \cdot \psi) \cdot \cos(\Delta) \cdot \cos(2 \cdot Ps) \cdot A2 \cdot \cos(2 \cdot Cs) \end{array} \right)$$

$$a_{33} = \frac{2 - q}{2} \gamma_{Pn} \cdot \left( \begin{array}{l} -A2 \cdot \sin(2 \cdot Cs) \cdot \cos(2 \cdot Ps) \cdot Sr1 + A2 \cdot \sin(2 \cdot Cs) \cdot \sin(2 \cdot Ps) \cdot Sr2 + A1 \cdot \cos(2 \cdot Cs) \cdot \\ \cos(2 \cdot Ps) \cdot Sr1 \ldots + -A1 \cdot \cos(2 \cdot Cs) \cdot \sin(2 \cdot Ps) \cdot Sr2 \ldots + \sin(2 \cdot \psi) \cdot \cos(\Delta) \cdot A1 \cdot \\ \sin(2 \cdot Cs) \cdot \sin(2 \cdot Ps) \cdot Sr1 \ldots + \sin(2 \cdot \psi) \cdot \cos(\Delta) \cdot A1 \cdot \sin(2 \cdot Cs) \cdot \cos(2 \cdot Ps) \cdot Sr2 + \\ \sin(2 \cdot \psi) \cdot \cos(\Delta) \cdot A2 \cdot \cos(2 \cdot Cs) \cdot \sin(2 \cdot Ps) \cdot Sr1 \ldots + \sin(2 \cdot \psi) \cdot \cos(\Delta) \cdot A2 \cdot \\ \cos(2 \cdot Cs) \cdot \cos(2 \cdot Ps) \cdot Sr2 \end{array} \right)$$

$$a_{34} = \frac{2 - q}{2} - \gamma_{Pn} \cdot \left( \begin{array}{l} -A2 \cdot \sin(2 \cdot Cs) \cdot \sin(2 \cdot Ps) \cdot Sr1 - A2 \cdot \sin(2 \cdot Cs) \cdot \sin(2 \cdot Ps) \cdot Sr2 + A1 \cdot \cos(2 \cdot Cs) \cdot \\ \sin(2 \cdot Ps) \cdot Sr1 \ldots + A1 \cdot \cos(2 \cdot Cs) \cdot \cos(2 \cdot Ps) \cdot Sr2 - \sin(2 \cdot \psi) \cdot \cos(\Delta) \cdot A1 \cdot \\ \sin(2 \cdot Cs) \cdot \cos(2 \cdot Ps) \cdot Sr1 \ldots + \sin(2 \cdot \psi) \cdot \cos(\Delta) \cdot A1 \cdot \sin(2 \cdot Cs) \cdot \sin(2 \cdot Ps) \cdot Sr2 - \\ \sin(2 \cdot \psi) \cdot \cos(\Delta) \cdot A2 \cdot \cos(2 \cdot Cs) \cdot \cos(2 \cdot Ps) \cdot Sr1 \ldots + \sin(2 \cdot \psi) \cdot \cos(\Delta) \cdot A2 \cdot \\ \cos(2 \cdot Cs) \cdot \sin(2 \cdot Ps) \cdot Sr2 \end{array} \right)$$

-continued

Rotating Polarizer/Rotating Compensator $$a_{40}=\frac{2-q}{2}\cdot\left(\begin{array}{l}\cos(2\cdot\psi)\cdot A1\cdot\sin(2\cdot Cs)+\cos(2\cdot\psi)\cdot A1\cdot\sin(2\cdot Cs)\cdot\ \alpha_p+\cos(2\cdot\psi)\cdot\\ A2\cdot\cos(2\cdot Cs)\ldots+\cos(2\cdot\psi)\cdot A2\cdot\cos(2\cdot Cs)\cdot\ \alpha_p-\gamma_{P_p}\cdot A1\cdot\sin(2\cdot Cs)\cdot\\ \cos(2\cdot Ps)\,Sr1\ldots+-\gamma_{P_p}\cdot A1\cdot\sin(2\cdot Cs)\cdot\sin(2\cdot Ps)\cdot Sr2-\gamma_{P_p}\cdot A2\cdot\\ \cos(2\cdot Cs)\cdot\cos(2\cdot Ps)\cdot Sr1\ldots+-\gamma_{P_p}\cdot A2\cdot\cos(2\cdot Cs)\cdot\sin(2\cdot Ps)\cdot\\ Sr2-\sin(2\cdot\psi)\cdot\cos(\Delta)\cdot\gamma_{P_p}\cdot A2\cdot\sin(2\cdot Cs)\cdot\sin(2\cdot Ps)\cdot Sr1\ldots+\sin(2\cdot\psi)\cdot\\ \cos(\Delta)\cdot\gamma_{P_p}\cdot A2\cdot\sin(2\cdot Cs)\cdot\cos(2\cdot Ps)\cdot Sr2\ldots+\sin(2\cdot\psi)\cdot\cos(\Delta)\cdot\\ \gamma_{P_p}\cdot A1\cdot\cos(2\cdot Cs)\cdot\sin(2\cdot Ps)\cdot Sr1\ldots+-\sin(2\cdot\psi)\cdot\cos(\Delta)\cdot\ \gamma_{P_p}\cdot A1\cdot\\ \cos(2\cdot Cs)\cdot\cos(2\cdot Ps)\cdot Sr2+2\cdot\sin(2\cdot\psi)\cdot\sin(\Delta)\cdot\sqrt{\alpha_p}\cdot Sr3\cdot A2\cdot\\ \sin(2\cdot Cs)\ldots+-2\cdot\sin(2\cdot\psi)\cdot\sin(\Delta)\cdot\sqrt{\alpha_p}\cdot Sr3\cdot A2\cdot\cos(2\cdot Cs)\end{array}\right)$$

$$a_{41}=\frac{2-q}{2}\cdot(1-\alpha_p)\cdot\left(\begin{array}{l}\cos(2\cdot\psi)\cdot Sr1\cdot A1\cdot\sin(2\cdot Cs)+\cos(2\cdot\psi)\cdot Sr1\cdot A2\cdot\cos(2\cdot Cs)-\cos(2\cdot Ps)\cdot\\ A1\cdot\sin(2\cdot Cs)\ldots+-\cos(2\cdot Ps)\cdot A2\cdot\cos(2\cdot Cs)-\sin(2\cdot\psi)\cdot\cos(\Delta)\cdot\\ \sin(2\cdot Ps)\cdot A2\cdot\sin(2\cdot Cs)\ldots+\sin(2\cdot\psi)\cdot\cos(\Delta)\cdot\sin(2\cdot Ps)\cdot A1\cdot\cos(2\cdot Cs)\end{array}\right)$$

$$a_{42}=\frac{2-q}{2}\cdot\left(\begin{array}{l}\cos(2\cdot\psi)\cdot Sr2\cdot A1\cdot\sin(2\cdot Cs)+\cos(2\cdot\psi)\cdot Sr2\cdot A2\cdot\cos(2\cdot Cs)-\sin(2\cdot Ps)\cdot\\ A1\cdot\sin(2\cdot Cs)\ldots+-\sin(2\cdot Ps)\cdot A2\cdot\cos(2\cdot Cs)\ldots+\sin(2\cdot\psi)\cdot\cos(\Delta)\cdot\\ \cos(2\cdot Ps)\cdot A2\cdot\sin(2\cdot Cs)-\sin(2\cdot\psi)\cdot\cos(\Delta)\cdot\cos(2\cdot Ps)\cdot A1\cdot\cos(2\cdot Cs)\end{array}\right)$$

$$a_{43}=\frac{2-q}{2}\cdot\left(\begin{array}{l}-A1\cdot\sin(2\cdot Cs)\cdot\cos(2\cdot Ps)\cdot Sr1+A1\cdot\sin(2\cdot Cs)\cdot\sin(2\cdot Ps)\cdot Sr2-A2\cdot\cos(2\cdot Cs)\cdot\\ \cos(2\cdot Ps)\cdot Sr1\ldots+A2\cdot\cos(2\cdot Cs)\cdot\sin(2\cdot Ps)\cdot Sr2-\sin(2\cdot\psi)\cdot\cos(\Delta)\cdot A2\cdot\\ \sin(2\cdot Cs)\cdot\sin(2\cdot Ps)\cdot Sr1\ldots+-\sin(2\cdot\psi)\cdot\cos(\Delta)\cdot A2\cdot\sin(2\cdot Cs)\cdot\cos(2\cdot Ps)\cdot Sr2+\\ \sin(2\cdot\psi)\cdot\cos(\Delta)\cdot A1\cdot\cos(2\cdot Cs)\cdot\sin(2\cdot Ps)\cdot Sr1\ldots+\sin(2\cdot\psi)\cdot\cos(\Delta)\cdot A1\cdot\\ \cos(2\cdot Cs)\cdot\cos(2\cdot Ps)\cdot Sr2\end{array}\right)$$

$$a_{44}=\frac{2-q}{2}-\gamma_{P_n}\cdot\left(\begin{array}{l}-A1\cdot\sin(2\cdot Cs)\cdot\sin(2\cdot Ps)\cdot Sr1-A1\cdot\sin(2\cdot Cs)\cdot\cos(2\cdot Ps)\cdot Sr2-A2\cdot\cos(2\cdot Cs)\cdot\\ \sin(2\cdot Ps)\cdot Sr1\ldots+-A2\cdot\cos(2\cdot Cs)\cdot\cos(2\cdot Ps)\cdot Sr2+\sin(2\cdot\psi)\cdot\cos(\Delta)\cdot A2\cdot\\ \sin(2\cdot Cs)\cdot\cos(2\cdot Ps)\cdot Sr1\ldots+-\sin(2\cdot\psi)\cdot\cos(\Delta)\cdot A2\cdot\sin(2\cdot Cs)\cdot\sin(2\cdot Ps)\cdot Sr2-\\ \sin(2\cdot\psi)\cdot\cos(\Delta)\cdot A1\cdot\cos(2\cdot Cs)\cdot\cos(2\cdot Ps)\cdot Sr1\ldots+\sin(2\cdot\psi)\cdot\cos(\Delta)\cdot A1\cdot\\ \cos(2\cdot Cs)\cdot\sin(2\cdot Ps)\cdot Sr2\end{array}\right)$$

FOR DUAL ROTATING COMPENSATOR CALIBRATION PROCEDURE (RCRC)

The method of Calibrating for Non-Idealities in Mathematical Representations of Rotated and Non-Rotated Components of a Sample System Investigating System described directly is applicable to Ellipsometers and Polarimeters which are sequentially comprised of a Source of a Beam of Electromagnetic wavelengths, a Polarizer means, typically for imposing a state of polarization upon said Beam of Electromagnetic wavelengths, a Stage for supporting a Sample System, an Analyzer means, typically for selecting a state of polarization in said Beam of Electromagnetic wavelengths and a Detector System. In addition, the Sample System Investigating System is further comprised of at least a First Compensator means, said at least a First Compensator means being positioned in said Sample System Investigating System at a location selected from the group consisting of, before and after, said Stage for supporting said Sample System. The Sample System Investigating System can also optionally comprise a Second Compensator means positioned in said Sample System Investigating System at a location complementary to said First Compensator means, said position being selected from the group consisting of, respectively, after and before, said Stage for supporting said Sample System.

An exemplary (RCRC) Calibration Method comprises the steps of:

Step a. Empirically obtaining at least two Data Sets, each of said Data Sets consisting of Intensity Values measured by said Detector system, said Intensity Values being a function of settings of Azimuthal angles of said First Compensator means and said Second Compensator means of said Sample System Investigating System. One of said Data sets being obtained with said Sample System Investigating System oriented in a "Sample-Present" configuration, and one of said Data being obtained with said Sample System Investigating System oriented in a configuration selected from the group consisting of "Alternative Sample-Present" and "Straight-Through". Which "Straight-Through" configuration results from orienting said Sample System Investigating System such that a Beam of Electromagnetic wavelengths provided by said Source of a Beam of Electromagnetic wavelengths is caused to pass through said Polarization means, through said Analyzer means and into said Detector system. And which "Sample Present" configuration results from orienting said Sample System Investigating System such that a Beam of Electromagnetic wavelengths provided by said Source of a Beam of Electromagnetic wavelengths is caused to pass through said Polarization means, interact with an Arbitrary Sample System supported by said Stage for supporting a Sample System, pass through said Analyzer means and into said Detector system. In either of said "Straight Through" or "Sample Present" configurations of said Sample System investigating system, said Beam of Electromagnetic wavelengths is also caused to pass through present First and Second Compensator means.

Step b. Applying mathematical formula to said Data Sets to provide Empirically derived Numerical Values for Coefficients of Two-Dimensional Mathematical Series, said Dimension of said Two-Dimensional Mathematical Series being determined by the number of Sample System Investigating System components, namely the First Compensator means and the Second Compensator means, which were caused to assume various Azimuthal Angle settings during the obtaining of Data Sets in step a.

Step c. Effectively deriving Analytical Non-Ideality Compensating Calibration Parameter containing Equations for Two-Dimensional Mathematical Series Coefficients, each of which effective Analytically Derived Non-Ideality Compensating Calibration Parameter containing Equations for Two-Dimensional Mathematical Series Coefficients is analogically equivalent to Numerical Values for corresponding Two-Dimensional Mathematical Series Coefficients Empirically determined by applying Mathematical Formula to the Data Sets as in Step b. The analogically equivalent Non-Ideality Compensating Calibration Parameter containing Equations for Two-Dimensional Mathematical Series Coefficients being provided by, for instance, performing Matrix Multiplication of Non-Ideality Compensating Calibration Parameter containing Matrices which represent Sample System Investigating System components and Rotation Matrices, each thereof being oriented in a series of said Sample System Investigating System component and Rotation Matrices to appropriately represent a "Straight-Through" or a "Sample Present" configuration of said Sample System investigating system.

Step d. Performing a simultaneous Mathematical Regression of Step c., Analytically arrived at effective Non-Ideality Compensating Calibration Parameter containing Equation for Coefficients of Two-Dimensional Mathematical Series, onto analogically equivalent Numerical Value for Two-Dimensional Mathematical Series Coefficients as arrived at in Step b.

The end result being that said Non-Ideality Compensating Calibration Parameters in said effective Non-Ideality Compensating Calibration Parameter containing Equations for Two-Dimensional Mathematical Series Coefficients are simultaneously Evaluated, based upon an error reducing criteria. Said Non-Ideality Compensating Calibration Parameters being for a Lumped combination of said Source of a Beam of Electromagnetic wavelengths and said Polarizer means, said First Compensator Means, said Second Compensator means, and for a Lumped combination of said Analyzer means and said Detector system, with the Arbitrary Sample System Characterization (PSI & DELTA or Mueller Matrix) also being provided.

Following directly are Print-Outs showing specific Calibration Parameter Containing Equations which analogically correspond the to Empirically Determined Numerical Values for the Double Fourier Series Matrix Elements, (ie. Coefficients), which Calibration Parameter Containing Equations are Regressed onto said Matrix Element Numerical Values to simultaneously provide Numerical Values for each Calibration Parameter.

In this (RCRC) case, the following Calibration Parameters are simultaneously evaluated:

| | Print-Out Symbol |
|---|---|
| Lumped Source and Polarizer: | |
| S0 (not present as normalization basis for S1, S2 and S3) | |
| S1 | S1 |
| S2 | S2 |
| S3 | S3 |
| Compensator 1: | |
| PSI (c1) | ψa |
| DELTA (c1) | δa |
| Sample System: | |
| Generalized Mueller Matrix Representation utilized rather than PSI and DELTA: | |
| $M = \begin{bmatrix} M11 & M12 & M13 & M14 \\ M21 & M22 & M23 & M24 \\ M31 & M32 & M33 & M34 \\ M41 & M42 & M43 & M44 \end{bmatrix}$ | |
| Compensator 2: | |
| PSI (c2) | ψb |
| DELTA (c2) | δb |
| Lumped Analyzer and Detector: | |
| A0 (not present as normalization basis for A1, A2 and A3) | |
| A1 | A1 |
| A2 | A2 |
| A3 | A3 |
| Rotation Angles: | |
| Rotation Azimuthal Angle to First Compensator | Θas |
| Rotation Azimuthal Angle to Second Compensator | Θbs |

(Note it typically is not necessary to distinguish the Lumped Source and Polarizer and the Lumped Analyzer and Detector as the Lumped Calibration Parameter Values do not involve the Sample System).

It is also to be appreciated that even though two Compensators are present, one is before and one after a Sample System. The two Compensators therefore do not have a simple combined effect of causing an undesirable one-hundred-eighty (180) degree phase shift.

Rotating Compensation/Rotating Compensator $$Msam = \begin{bmatrix} M_{11} & M_{12} & M_{13} & M_{14} \\ M_{21} & M_{22} & M_{23} & M_{24} \\ M_{31} & M_{32} & M_{33} & M_{34} \\ M_{41} & M_{42} & M_{43} & M_{44} \end{bmatrix}$$

$q_a = 1 + \sin(2\cdot\psi_a)\cdot\cos(\delta_a)$ $\quad r_a = \sin(2\cdot\psi_a)\cdot\sin(\delta_a)$ $\quad s_a = \cos(2\cdot\psi_a)$ $\quad a_c = \cos(2\cdot\theta_{as})$ $\quad a_s = \sin(2\cdot\theta_{as})$ $q_b = 1 + \sin(2\cdot\psi_b)\cdot\cos(\delta_b)$ $\quad r_b = \sin(2\cdot\psi_b)\cdot\sin(\delta_b)$ $\quad b = \cos(2\cdot\psi_b)$ $\quad b_c = \cos(2\cdot\theta_{bs})$ $\quad b_s = \sin(2\cdot\theta_{bs})$ $$a_{00} = A_0\cdot S_0\cdot\left[\begin{array}{l}
S_3\cdot A_3\cdot M_{44} + S_3\cdot M_{14}\cdot q_a + A_3\cdot M_{41}\cdot q_b + \frac{1}{2}\cdot M_{21}\cdot A_1\cdot q_b\cdot b_c + \frac{1}{2}\cdot M_{21}\cdot A_2\cdot q_b\cdot b_s \ldots + \frac{-1}{2}\cdot M_{31}\cdot A_1\cdot q_b\cdot b_s + \frac{1}{2}\cdot M_{31}\cdot A_2\cdot q_b\cdot b_c - A_3\cdot M_{41} + M_{11} - \frac{1}{4}\cdot M_{23}\cdot A_1\cdot \\
q_b\cdot b_c\cdot a_s\cdot q_a\cdot s_1 \ldots + \frac{1}{4}\cdot M_{32}\cdot A_2\cdot q_b\cdot b_c\cdot a_s\cdot q_a\cdot S_2 + \frac{1}{4}\cdot M_{32}\cdot A_2\cdot q_b\cdot b_c\cdot a_c\cdot q_a\cdot S_1 + \frac{1}{2}\cdot S_3\cdot M_{34}\cdot A_2\cdot q_b\cdot b_c\cdot q_a \ldots + \frac{-1}{2}\cdot S_3\cdot M_{34}\cdot A_1\cdot q_b\cdot b_s\cdot q_a + \frac{1}{2}\cdot S_3\cdot \\
M_{24}\cdot A_2\cdot q_b\cdot b_s\cdot q_a - \frac{1}{4}\cdot M_{32}\cdot A_1\cdot q_b\cdot b_s\cdot a_s\cdot q_a\cdot S_2 \ldots + S_3\cdot A_3\cdot M_{44}\cdot q_b\cdot q_a - \frac{1}{2}\cdot S_3\cdot M_{34}\cdot A_2\cdot q_b\cdot b_c + \frac{1}{2}\cdot S_3\cdot M_{34}\cdot A_1\cdot q_b\cdot b_s \ldots + \frac{1}{2}\cdot S_3\cdot M_{24}\cdot A_1\cdot q_b\cdot b_c\cdot q_a \ldots + \\
-S_3\cdot A_3\cdot M_{44}\cdot q_b - \frac{1}{4}\cdot M_{32}\cdot A_1\cdot q_b\cdot b_s\cdot a_c\cdot q_a\cdot S_1 - \frac{1}{2}\cdot S_3\cdot M_{24}\cdot A_2\cdot q_b\cdot b_s - A_3\cdot M_{44}\cdot q_a \ldots + \frac{1}{4}\cdot M_{22}\cdot A_2\cdot q_b\cdot b_s\cdot a_s\cdot q_a\cdot S_2 - \frac{1}{2}\cdot S_3\cdot M_{24}\cdot A_1\cdot q_b\cdot b_c + \frac{1}{4}\cdot M_{22}\cdot A_2\cdot \\
q_b\cdot b_s\cdot a_c\cdot q_a\cdot S_1 \ldots + \frac{1}{4}\cdot M_{22}\cdot A_1\cdot q_b\cdot b_c\cdot a_s\cdot q_a\cdot S_2 - S_3\cdot M_{14} + \frac{1}{2}\cdot M_{13}\cdot a_c\cdot q_a\cdot S_2 - \frac{1}{2}\cdot M_{13}\cdot a_s\cdot q_a\cdot S_1 \ldots + \frac{1}{2}\cdot A_3\cdot M_{43}\cdot q_b\cdot a_c\cdot q_a\cdot S_2 - \frac{1}{2}\cdot A_3\cdot M_{43}\cdot a_c\cdot q_a\cdot S_2 + \\
\frac{1}{2}\cdot A_3\cdot M_{43}\cdot a_s\cdot q_a\cdot S_1 \ldots + \frac{1}{4}\cdot M_{22}\cdot A_1\cdot q_b\cdot b_c\cdot a_c\cdot q_a\cdot S_1 - \frac{1}{2}\cdot A_3\cdot M_{43}\cdot q_b\cdot a_s\cdot q_a\cdot S_1 + \frac{1}{2}\cdot A_3\cdot M_{42}\cdot q_b\cdot a_s\cdot q_a\cdot S_2 \ldots + \frac{1}{2}\cdot A_3\cdot M_{42}\cdot q_b\cdot a_c\cdot q_a\cdot S_1 + \frac{1}{2}\cdot M_{12}\cdot \\
a_s\cdot q_a\cdot S_2 + \frac{1}{2}\cdot M_{12}\cdot a_c\cdot q_a\cdot S_1 - \frac{1}{2}\cdot A_3\cdot M_{42}\cdot a_s\cdot q_a\cdot S_2 \ldots + \frac{-1}{2}\cdot A_3\cdot M_{42}\cdot a_c\cdot q_a\cdot S_1 + \frac{1}{4}\cdot M_{33}\cdot A_2\cdot q_b\cdot b_c\cdot a_c\cdot q_a\cdot S_2 - \frac{1}{4}\cdot M_{33}\cdot A_2\cdot q_b\cdot b_c\cdot a_s\cdot q_a\cdot S_1 \ldots + \\
\frac{-1}{4}\cdot M_{33}\cdot A_1\cdot q_b\cdot b_s\cdot a_c\cdot q_a\cdot S_2 + \frac{1}{4}\cdot M_{33}\cdot A_1\cdot q_b\cdot b_s\cdot a_s\cdot q_a\cdot S_1 + \frac{1}{4}\cdot M_{23}\cdot A_2\cdot q_b\cdot b_s\cdot a_c\cdot q_a\cdot S_2 \ldots + \frac{-1}{4}\cdot M_{23}\cdot A_2\cdot q_b\cdot b_s\cdot a_s\cdot q_a\cdot S_1 + \frac{1}{4}\cdot M_{23}\cdot A_1\cdot q_b\cdot b_c\cdot a_c\cdot q_a\cdot S_2
\end{array}\right]$$

$$a_{01} = A_0\cdot A_0\cdot\left[\begin{array}{l}
-s_a\cdot S_1\cdot M_{11} - r_a\cdot S_2\cdot M_{14} + \frac{1}{2}\cdot M_{23}\cdot A_2\cdot b_s\cdot a_c\cdot r_a\cdot S_3 - \frac{1}{2}\cdot r_a\cdot S_2\cdot M_{34}\cdot A_2\cdot q_b\cdot b_c \ldots + r_a\cdot S_2\cdot A_3\cdot M_{44} + \frac{1}{2}\cdot r_a\cdot S_2\cdot M_{34}\cdot A_1\cdot q_b\cdot b_s - r_a\cdot S_2\cdot A_3\cdot M_{44}\cdot q_b - \frac{1}{2}\cdot r_a\cdot S_2\cdot M_{24}\cdot \\
A_1\cdot q_b\cdot b_c \ldots + M_{13}\cdot a_c\cdot r_a\cdot S_3 - \frac{1}{2}\cdot r_a\cdot S_2\cdot M_{24}\cdot A_2\cdot q_b\cdot b_s + A_3\cdot M_{43}\cdot q_b\cdot a_c\cdot r_a\cdot S_3 - A_3\cdot M_{43}\cdot a_c\cdot r_a\cdot S_3 \ldots + \frac{1}{2}\cdot M_{33}\cdot A_2\cdot q_b\cdot b_c\cdot a_c\cdot r_a\cdot S_3 - A_3\cdot M_{43}\cdot a_s\cdot s_a + \frac{1}{2}\cdot \\
M_{33}\cdot A_2\cdot q_b\cdot b_c\cdot a_s\cdot s_a \ldots + A_3\cdot M_{43}\cdot q_b\cdot a_s\cdot s_a \ldots + \frac{-1}{2}\cdot M_{33}\cdot A_1\cdot q_b\cdot b_s\cdot a_s\cdot s_a - \frac{1}{2}\cdot M_{33}\cdot A_1\cdot q_b\cdot b_s\cdot a_c\cdot r_a\cdot S_3 + \frac{1}{2}\cdot M_{23}\cdot A_2\cdot q_b\cdot b_s\cdot a_s\cdot s_a \ldots + \frac{-1}{2}\cdot M_{22}\cdot \\
A_2\cdot q_b\cdot b_s\cdot a_c\cdot s_a + \frac{1}{2}\cdot M_{23}\cdot A_1\cdot q_b\cdot b_c\cdot a_c\cdot r_a\cdot S_3 + M_{13}\cdot a_s\cdot s_a \ldots + \frac{1}{2}\cdot M_{23}\cdot A_1\cdot q_b\cdot b_c\cdot a_s\cdot s_a \ldots + A_3\cdot M_{42}\cdot q_b\cdot a_s\cdot r_a\cdot S_3 - A_3\cdot M_{42}\cdot a_s\cdot r_a\cdot S_3 + M_{12}\cdot a_s\cdot r_a\cdot S_3 + \frac{1}{2}\cdot \\
M_{32}\cdot A_2\cdot q_b\cdot b_c\cdot a_s\cdot r_a\cdot S_3 \ldots + -A_3\cdot M_{42}\cdot q_b\cdot a_c\cdot s_a - \frac{1}{2}\cdot M_{32}\cdot A_2\cdot q_b\cdot b_c\cdot a_c\cdot s_a + A_3\cdot M_{42}\cdot a_c\cdot s_a \ldots + \frac{-1}{2}\cdot M_{32}\cdot A_1\cdot q_b\cdot b_s\cdot a_s\cdot r_a\cdot S_3 \ldots + -M_{12}\cdot a_c\cdot s_a + \frac{1}{2}\cdot M_{32}\cdot \\
A_1\cdot q_b\cdot b_s\cdot a_c\cdot s_a + \frac{1}{2}\cdot M_{22}\cdot A_2\cdot q_b\cdot b_s\cdot a_s\cdot r_a\cdot S_3 \ldots + \frac{1}{2}\cdot M_{22}\cdot A_1\cdot q_b\cdot b_c\cdot a_s\cdot r_a\cdot S_3 \ldots + \frac{-1}{2}\cdot M_{22}\cdot A_1\cdot q_b\cdot b_c\cdot a_c\cdot s_a - s_a\cdot S_1\cdot A_3\cdot M_{41}\cdot q_b\cdot s_a\cdot S_1\cdot A_3\cdot M_{41} \ldots + \\
\frac{-1}{2}\cdot s_a\cdot S_1\cdot M_{31}\cdot A_2\cdot q_b\cdot b_c \ldots + \frac{1}{2}\cdot s_a\cdot S_1\cdot M_{31}\cdot A_1\cdot q_b\cdot b_s - \frac{1}{2}\cdot s_a\cdot S_1\cdot M_{21}\cdot A_1\cdot q_b\cdot b_c - \frac{1}{2}\cdot s_a\cdot S_1\cdot M_{21}\cdot A_2\cdot q_b\cdot b_s
\end{array}\right]$$

-continued

Rotating Compensation/Rotating Compensator $$a_{02} = A_0 \cdot S_0 \cdot \Big[ -r_a \cdot S_1 \cdot M_{14} + M_{13} \cdot a_c \cdot s_a + M_{12} \cdot a_s \cdot s_a + s_a \cdot S_2 \cdot M_{11} - \frac{1}{2} \cdot r_a \cdot S_1 \cdot M_{24} \cdot A_1 \cdot q_b \cdot b_c \ldots + \frac{-1}{2} \cdot r_a \cdot S_1 \cdot M_{24} \cdot A_2 \cdot q_b \cdot b_s + A_3 \cdot M_{43} \cdot a_s \cdot r_a \cdot S_3 - M_{13} \cdot a_s \cdot r_a \cdot S_3 - r_a \cdot S_1 \cdot A_3 \cdot M_{44} \cdot q_b \ldots +$$
$$\frac{-1}{2} \cdot M_{23} \cdot A_2 \cdot q_b \cdot b_s \cdot a_s \cdot r_a \cdot S_3 - \frac{1}{2} \cdot M_{33} \cdot A_1 \cdot q_b \cdot b_s \cdot a_c \cdot s_a + \frac{1}{2} \cdot M_{33} \cdot A_2 \cdot q_b \cdot b_c \cdot a_c \cdot s_a \ldots + \frac{-1}{2} \cdot M_{33} \cdot A_2 \cdot q_b \cdot b_c \cdot a_s \cdot r_a \cdot S_3 + A_3 \cdot M_{43} \cdot q_b \cdot a_c \cdot s_a - A_3 \cdot M_{43} \cdot a_c \cdot s_a \ldots +$$
$$-\frac{1}{2} \cdot r_a \cdot S_1 \cdot M_{34} \cdot A_2 \cdot q_b \cdot b_c \ldots + r_a \cdot S_1 \cdot A_3 \cdot M_{44} + \frac{1}{2} \cdot M_{22} \cdot A_1 \cdot q_b \cdot b_c \cdot a_c \cdot r_a \cdot S_3 + \frac{1}{2} \cdot M_{22} \cdot A_2 \cdot q_b \cdot b_s \cdot a_c \cdot r_a \cdot S_3 \ldots + \frac{1}{2} \cdot M_{22} \cdot A_1 \cdot q_b \cdot b_c \cdot a_s \cdot s_a - A_3 \cdot M_{42} \cdot a_s \cdot s_a + \frac{1}{2} \cdot$$
$$M_{22} \cdot A_2 \cdot q_b \cdot b_s \cdot a_s \cdot s_a \ldots + \frac{1}{2} \cdot M_{32} \cdot A_2 \cdot q_b \cdot b_c \cdot a_c \cdot r_a \cdot S_3 \ldots + A_3 \cdot M_{42} \cdot q_b \cdot a_s \cdot s_a + A_3 \cdot M_{42} \cdot q_b \cdot a_c \cdot r_a \cdot S_3 - A_3 \cdot M_{42} \cdot a_c \cdot r_a \cdot S_3 \ldots + M_{12} \cdot a_c \cdot r_a \cdot S_3 - \frac{1}{2} \cdot M_{32} \cdot A_1 \cdot q_b \cdot b_s \cdot$$
$$a_s \cdot s_a - \frac{1}{2} \cdot M_{32} \cdot A_1 \cdot q_b \cdot b_s \cdot a_c \cdot r_a \cdot S_3 \ldots + \frac{1}{2} \cdot M_{32} \cdot A_2 \cdot q_b \cdot b_c \cdot a_s \cdot s_a \ldots + s_a \cdot S_2 \cdot A_3 \cdot M_{41} \cdot q_b - \frac{1}{2} \cdot s_a \cdot S_2 \cdot M_{31} \cdot A_1 \cdot q_b \cdot b_s + \frac{1}{2} \cdot s_a \cdot S_2 \cdot M_{31} \cdot A_2 \cdot q_b \cdot b_c \ldots + \frac{1}{2} \cdot s_a \cdot S_2 \cdot$$
$$M_{21} \cdot A_2 \cdot q_b \cdot b_s - s_a \cdot S_2 \cdot A_3 \cdot M_{41} + \frac{1}{2} \cdot s_a \cdot S_2 \cdot M_{21} \cdot A_1 \cdot q_b \cdot b_c \ldots + \frac{1}{2} \cdot M_{23} \cdot A_1 \cdot q_b \cdot b_c \cdot a_c \cdot s_a - \frac{1}{2} \cdot M_{23} \cdot A_1 \cdot q_b \cdot b_c \cdot a_s \cdot r_a \cdot S_3 + \frac{1}{2} \cdot M_{23} \cdot A_2 \cdot q_b \cdot b_s \cdot a_c \cdot s_a \ldots + \frac{1}{2} \cdot M_{33} \cdot$$
$$A_1 \cdot q_b \cdot b_s \cdot a_s \cdot r_a \cdot S_3 - A_3 \cdot M_{43} \cdot q_b \cdot a_s \cdot r_a \cdot S_3 + \frac{1}{2} \cdot r_a \cdot S_1 \cdot M_{34} \cdot A_1 \cdot q_b \cdot b_s \Big]$$

$$a_{03} = A_0 \cdot S_0 \cdot \frac{2 - q_a}{2} \cdot \Big[ -M_{13} \cdot a_c \cdot S_2 - M_{12} \cdot a_s \cdot S_2 - \frac{1}{2} \cdot M_{32} \cdot A_1 \cdot q_b \cdot b_s \cdot a_c \cdot S_1 + \frac{1}{2} \cdot M_{32} \cdot A_1 \cdot q_b \cdot b_s \cdot a_s \cdot S_2 \ldots + \frac{-1}{2} \cdot M_{23} \cdot A_1 \cdot q_b \cdot b_c \cdot a_s \cdot S_1 - \frac{1}{2} \cdot M_{23} \cdot A_1 \cdot q_b \cdot b_c \cdot a_c \cdot S_2 + A_3 \cdot M_{42} \cdot a_s \cdot$$
$$S_2 \ldots + A_3 \cdot M_{43} \cdot a_c \cdot S_2 \ldots + \frac{1}{2} \cdot M_{33} \cdot A_1 \cdot q_b \cdot b_s \cdot a_s \cdot S_1 + \frac{1}{2} \cdot M_{33} \cdot A_1 \cdot q_b \cdot b_s \cdot a_c \cdot S_2 - \frac{1}{2} \cdot M_{33} \cdot A_2 \cdot q_b \cdot b_c \cdot a_s \cdot S_1 \ldots + \frac{1}{2} \cdot M_{32} \cdot A_2 \cdot q_b \cdot b_c \cdot a_c \cdot S_1 - \frac{1}{2} \cdot M_{32} \cdot A_2 \cdot$$
$$q_b \cdot b_c \cdot a_s \cdot S_2 + A_3 \cdot M_{42} \cdot q_b \cdot a_c \cdot S_1 \ldots + -A_3 \cdot M_{42} \cdot q_b \cdot a_s \cdot S_2 + M_{12} \cdot a_c \cdot S_1 - \frac{1}{2} \cdot M_{22} \cdot A_2 \cdot q_b \cdot b_s \cdot a_s \cdot S_2 \ldots + \frac{1}{2} \cdot M_{22} \cdot A_2 \cdot q_b \cdot b_s \cdot a_c \cdot S_1 \ldots + \frac{-1}{2} \cdot M_{22} \cdot A_1 \cdot q_b \cdot b_c \cdot a_s \cdot$$
$$S_2 + \frac{1}{2} \cdot M_{22} \cdot A_1 \cdot q_b \cdot b_c \cdot a_c \cdot S_1 - A_3 \cdot M_{42} \cdot a_c \cdot S_1 \ldots + \frac{-1}{2} \cdot M_{23} \cdot A_2 \cdot q_b \cdot b_s \cdot a_s \cdot S_1 - \frac{1}{2} \cdot M_{23} \cdot A_2 \cdot q_b \cdot b_s \cdot a_c \cdot S_2 - \frac{1}{2} \cdot M_{33} \cdot A_2 \cdot q_b \cdot b_c \cdot a_c \cdot S_2 \ldots + -A_3 \cdot M_{43} \cdot q_b \cdot$$
$$a_s \cdot S_1 - A_3 \cdot M_{43} \cdot q_b \cdot a_c \cdot S_2 + A_3 \cdot M_{43} \cdot a_s \cdot S_1 - M_{13} \cdot a_s \cdot S_1 \Big]$$

$$a_{04} = A_0 \cdot S_0 \cdot \frac{2 - q_a}{2} \cdot \Big[ -M_{13} \cdot a_s \cdot S_2 - M_{13} \cdot a_c \cdot S_1 - M_{12} \cdot a_c \cdot S_2 - M_{12} \cdot a_s \cdot S_1 - A_3 \cdot M_{43} \cdot q_b \cdot a_c \cdot S_1 \ldots + A_3 \cdot M_{43} \cdot a_s \cdot S_2 - A_3 \cdot M_{43} \cdot q_b \cdot a_s \cdot S_2 - \frac{1}{2} \cdot M_{33} \cdot A_2 \cdot q_b \cdot b_c \cdot a_c \cdot$$
$$S_1 \ldots + \frac{1}{2} \cdot M_{33} \cdot A_2 \cdot q_b \cdot b_c \cdot a_s \cdot S_2 + A_3 \cdot M_{43} \cdot a_c \cdot S_1 + \frac{1}{2} \cdot M_{32} \cdot A_1 \cdot q_b \cdot b_s \cdot a_s \cdot S_1 \ldots + \frac{1}{2} \cdot M_{32} \cdot A_1 \cdot q_b \cdot b_s \cdot a_c \cdot S_2 - \frac{1}{2} \cdot M_{22} \cdot A_2 \cdot q_b \cdot b_s \cdot a_c \cdot S_2 - A_3 \cdot M_{42} \cdot q_b \cdot a_s \cdot$$
$$S_1 \ldots + -\frac{1}{2} \cdot M_{22} \cdot A_1 \cdot q_b \cdot b_c \cdot a_c \cdot S_2 - \frac{1}{2} \cdot M_{22} \cdot A_2 \cdot q_b \cdot b_s \cdot a_s \cdot S_1 - \frac{1}{2} \cdot M_{22} \cdot A_1 \cdot q_b \cdot b_c \cdot a_s \cdot S_1 \ldots + -\frac{1}{2} \cdot M_{33} \cdot A_1 \cdot q_b \cdot b_s \cdot a_s \cdot S_2 - \frac{1}{2} \cdot M_{23} \cdot A_2 \cdot q_b \cdot b_s \cdot a_c \cdot S_1 +$$
$$\frac{1}{2} \cdot M_{33} \cdot A_1 \cdot q_b \cdot b_s \cdot a_c \cdot S_1 \ldots + \frac{1}{2} \cdot M_{23} \cdot A_2 \cdot q_b \cdot b_s \cdot a_s \cdot S_2 - \frac{1}{2} \cdot M_{23} \cdot A_1 \cdot q_b \cdot b_c \cdot a_c \cdot S_1 + \frac{1}{2} \cdot M_{23} \cdot A_1 \cdot q_b \cdot b_c \cdot a_s \cdot S_2 \ldots + -A_3 \cdot M_{42} \cdot q_b \cdot a_c \cdot S_2 + A_3 \cdot M_{42} \cdot a_s \cdot$$
$$S_1 - \frac{1}{2} \cdot M_{32} \cdot A_2 \cdot q_b \cdot b_c \cdot a_c \cdot S_2 \ldots + \frac{-1}{2} \cdot M_{32} \cdot A_2 \cdot q_b \cdot b_c \cdot a_s \cdot S_1 + A_3 \cdot M_{42} \cdot a_c \cdot S_2 \Big]$$

-continued

Rotating Compensation/Rotating Compensator $$a_{10} = A_0 \cdot S_0 \cdot \left[\begin{array}{l} -M_{31} \cdot s_b \cdot b_s - M_{21} \cdot s_b \cdot b_c + A_2 \cdot r_b \cdot M_{41} - A_1 \cdot s_b \cdot M_{11} + S_3 \cdot A_1 \cdot s_b \cdot M_{14} \ldots + -S_3 \cdot M_{24} \cdot s_b \cdot b_c \cdot q_a \ldots + S_3 \cdot M_{24} \cdot s_b \cdot b_c - S_3 \cdot A_2 \cdot r_b \cdot M_{44} - S_3 \cdot A_1 \cdot s_b \cdot M_{14} \cdot q_a - S_3 \cdot M_{24} \cdot A_3 \cdot r_b \cdot \\ b_s \cdot q_a \ldots + S_3 \cdot M_{24} \cdot A_3 \cdot r_b \cdot b_s - S_3 \cdot M_{34} \cdot s_b \cdot b_s \cdot q_a + S_3 \cdot M_{34} \cdot s_b \cdot b_s - \frac{1}{2} \cdot M_{33} \cdot A_3 \cdot r_b \cdot b_c \cdot a_c \cdot q_a \cdot S_2 \ldots + -\frac{1}{2} \cdot A_2 \cdot r_b \cdot M_{43} \cdot a_s \cdot q_a \cdot S_1 - S_3 \cdot M_{34} \cdot A_3 \cdot r_b \cdot b_c \cdot q_a + S_3 \cdot M_{34} \cdot \\ A_3 \cdot r_b \cdot b_c \ldots + S_3 \cdot A_2 \cdot r_b \cdot M_{44} \cdot q_a \ldots + -\frac{1}{2} \cdot A_1 \cdot s_b \cdot M_{13} \cdot a_c \cdot q_a \cdot S_2 - \frac{1}{2} \cdot M_{33} \cdot s_b \cdot b_s \cdot a_c \cdot q_a \cdot S_2 + \frac{1}{2} \cdot M_{33} \cdot s_b \cdot b_s \cdot a_s \cdot q_a \cdot S_1 \ldots + \frac{1}{2} \cdot M_{33} \cdot A_3 \cdot r_b \cdot b_c \cdot a_s \cdot q_a \cdot S_1 - \frac{1}{2} \cdot \\ M_{23} \cdot A_3 \cdot r_b \cdot b_s \cdot a_c \cdot q_a \cdot S_2 + \frac{1}{2} \cdot M_{23} \cdot A_3 \cdot r_b \cdot b_s \cdot a_s \cdot q_a \cdot S_1 \ldots + \frac{-1}{2} \cdot M_{23} \cdot s_b \cdot b_c \cdot a_c \cdot q_a \cdot S_2 + \frac{1}{2} \cdot M_{23} \cdot s_b \cdot b_c \cdot a_s \cdot q_a \cdot S_1 + \frac{1}{2} \cdot A_1 \cdot s_b \cdot M_{13} \cdot a_s \cdot q_a \cdot S_1 \ldots + \frac{1}{2} \cdot A_2 \cdot \\ r_b \cdot M_{42} \cdot a_s \cdot q_a \cdot S_2 - \frac{1}{2} \cdot M_{32} \cdot A_3 \cdot r_b \cdot b_c \cdot a_s \cdot q_a \cdot S_2 + \frac{1}{2} \cdot A_2 \cdot r_b \cdot M_{42} \cdot a_c \cdot q_a \cdot S_1 \ldots + \frac{-1}{2} \cdot M_{32} \cdot s_b \cdot b_s \cdot a_s \cdot q_a \cdot S_2 - \frac{1}{2} \cdot M_{32} \cdot A_3 \cdot r_b \cdot b_c \cdot a_c \cdot q_a \cdot S_1 - \frac{1}{2} \cdot M_{32} \cdot s_b \cdot b_s \cdot \\ a_c \cdot q_a \cdot S_1 \ldots + \frac{-1}{2} \cdot M_{22} \cdot A_3 \cdot r_b \cdot b_s \cdot a_s \cdot q_a \cdot S_2 - \frac{1}{2} \cdot M_{22} \cdot A_3 \cdot r_b \cdot b_s \cdot a_c \cdot q_a \cdot S_1 - \frac{1}{2} \cdot M_{22} \cdot s_b \cdot b_c \cdot a_s \cdot q_a \cdot S_2 \ldots + \frac{-1}{2} \cdot M_{22} \cdot s_b \cdot b_c \cdot a_c \cdot q_a \cdot S_1 - \frac{1}{2} \cdot A_1 \cdot s_b \cdot M_{12} \cdot \\ a_c \cdot q_a \cdot S_1 - \frac{1}{2} \cdot A_1 \cdot s_b \cdot M_{12} \cdot a_s \cdot q_a \cdot S_2 \ldots + -M_{31} \cdot A_3 \cdot r_b \cdot b_c + -M_{21} \cdot A_3 \cdot r_b \cdot b_s + \frac{1}{2} \cdot A_2 \cdot r_b \cdot M_{43} \cdot a_c \cdot q_a \cdot S_2 \end{array}\right]$$

$$a_{11} = A_0 \cdot S_0 \cdot \left[\begin{array}{l} -M_{33} \cdot s_b \cdot b_s \cdot a_s \cdot s_a - M_{33} \cdot s_b \cdot b_s \cdot a_c \cdot r_a \cdot S_3 + r_a \cdot S_2 \cdot M_{34} \cdot s_b \cdot b_s + r_a \cdot S_2 \cdot M_{34} \cdot A_3 \cdot r_b \cdot b_c \ldots + -M_{23} \cdot s_b \cdot b_c \cdot a_c \cdot r_a \cdot S_3 - M_{23} \cdot A_3 \cdot r_b \cdot b_s \cdot a_s \cdot s_a - M_{33} \cdot A_3 \cdot r_b \cdot b_c \cdot a_s \cdot s_a + r_a \cdot S_2 \cdot \\ A_1 \cdot s_b \cdot M_{14} \ldots + r_a \cdot S_2 \cdot M_{24} \cdot s_b \cdot b_c - M_{33} \cdot A_3 \cdot r_b \cdot b_c \cdot a_c \cdot r_a \cdot S_3 + A_2 \cdot r_b \cdot M_{43} \cdot a_s \cdot s_a + A_2 \cdot r_b \cdot M_{43} \cdot a_c \cdot r_a \cdot S_3 \ldots + A_1 \cdot s_b \cdot M_{12} \cdot a_c \cdot s_a + M_{22} \cdot s_b \cdot b_c \cdot a_c \cdot s_a + s_a \cdot S_1 \cdot M_{31} \cdot A_3 \cdot r_b \cdot \\ b_c - s_a \cdot S_1 \cdot A_2 \cdot r_b \cdot M_{41} \ldots + s_a \cdot S_1 \cdot M_{21} \cdot A_3 \cdot r_b \cdot b_s + s_a \cdot S_1 \cdot M_{31} \cdot s_b \cdot b_s + s_a \cdot S_1 \cdot A_1 \cdot s_b \cdot M_{11} - M_{23} \cdot s_b \cdot b_c \cdot a_s \cdot s_a \ldots + -M_{23} \cdot A_3 \cdot r_b \cdot b_s \cdot a_c \cdot r_a \cdot S_3 - A_1 \cdot s_b \cdot M_{13} \cdot a_c \cdot r_a \cdot S_3 - A_1 \cdot \\ s_b \cdot M_{13} \cdot a_s \cdot s_a \ldots + -A_1 \cdot s_b \cdot M_{12} \cdot a_s \cdot r_a \cdot S_3 + A_2 \cdot r_b \cdot M_{42} \cdot a_s \cdot r_a \cdot S_3 - M_{32} \cdot A_3 \cdot r_b \cdot b_c \cdot a_s \cdot r_a \cdot S_3 \ldots + -A_2 \cdot r_b \cdot M_{42} \cdot a_c \cdot s_a + M_{32} \cdot A_3 \cdot r_b \cdot b_c \cdot a_c \cdot s_a + M_{32} \cdot s_b \cdot b_s \cdot a_c \cdot s_a - M_{32} \cdot \\ s_b \cdot b_s \cdot a_s \cdot r_a \cdot S_3 \ldots + -M_{22} \cdot A_3 \cdot r_b \cdot b_s \cdot a_s \cdot r_a \cdot S_3 - M_{22} \cdot s_b \cdot b_c \cdot a_s \cdot r_a \cdot S_3 + M_{22} \cdot A_3 \cdot r_b \cdot b_s \cdot a_c \cdot s_a \ldots + s_a \cdot S_1 \cdot M_{21} \cdot s_b \cdot b_c + r_a \cdot S_2 \cdot M_{24} \cdot A_3 \cdot r_b \cdot b_s - r_a \cdot S_2 \cdot A_2 \cdot r_b \cdot M_{44} \end{array}\right]$$

$$a_{12} = A_0 \cdot S_0 \cdot \left[\begin{array}{l} A_1 \cdot s_b \cdot M_{13} \cdot a_s \cdot r_a \cdot S_3 + M_{23} \cdot s_b \cdot b_c \cdot a_s \cdot r_a \cdot S_3 - r_a \cdot S_1 \cdot A_2 \cdot r_b \cdot M_{44} + r_a \cdot S_1 \cdot M_{34} \cdot s_b \cdot b_s \ldots + r_a \cdot S_1 \cdot M_{34} \cdot A_3 \cdot r_b \cdot b_c + M_{23} \cdot A_3 \cdot r_b \cdot b_s \cdot a_s \cdot r_a \cdot S_3 + M_{33} \cdot s_b \cdot b_s \cdot a_s \cdot r_a \cdot S_3 \ldots + \\ -A_2 \cdot r_b \cdot M_{43} \cdot a_s \cdot r_a \cdot S_3 \ldots + r_a \cdot S_1 \cdot A_1 \cdot s_b \cdot M_{14} + r_a \cdot S_1 \cdot M_{24} \cdot s_b \cdot b_c + r_a \cdot S_1 \cdot M_{24} \cdot A_3 \cdot r_b \cdot b_s - M_{32} \cdot A_3 \cdot r_b \cdot b_c \cdot a_s \cdot s_a \ldots + -M_{23} \cdot s_b \cdot b_c \cdot a_c \cdot s_a - M_{22} \cdot s_b \cdot b_c \cdot a_s \cdot s_a - A_1 \cdot s_b \cdot M_{12} \cdot \\ a_c \cdot r_a \cdot S_3 + s_a \cdot S_2 \cdot A_2 \cdot r_b \cdot M_{41} \ldots + -A_1 \cdot s_b \cdot M_{12} \cdot a_s \cdot s_a - s_a \cdot S_2 \cdot M_{31} \cdot A_3 \cdot r_b \cdot b_c - s_a \cdot S_2 \cdot M_{31} \cdot s_b \cdot b_s - s_a \cdot S_2 \cdot M_{21} \cdot A_3 \cdot r_b \cdot b_s \ldots + -s_a \cdot S_2 \cdot A_1 \cdot s_b \cdot M_{11} - s_a \cdot S_2 \cdot M_{21} \cdot \\ s_b \cdot b_c - M_{23} \cdot A_3 \cdot r_b \cdot b_s \cdot a_c \cdot s_a - M_{33} \cdot A_3 \cdot r_b \cdot b_c \cdot a_c \cdot s_a \ldots + M_{33} \cdot A_3 \cdot r_b \cdot b_c \cdot a_s \cdot r_a \cdot S_3 + A_2 \cdot r_b \cdot M_{43} \cdot a_c \cdot s_a + A_2 \cdot r_b \cdot M_{42} \cdot a_c \cdot r_a \cdot S_3 - A_1 \cdot s_b \cdot M_{13} \cdot a_c \cdot s_a \ldots + -M_{32} \cdot A_3 \cdot r_b \cdot b_c \cdot a_c \cdot \\ r_a \cdot S_3 + A_2 \cdot r_b \cdot M_{42} \cdot a_s \cdot s_a - M_{22} \cdot A_3 \cdot r_b \cdot b_s \cdot a_c \cdot r_a \cdot S_3 \ldots + -M_{32} \cdot s_b \cdot b_s \cdot a_c \cdot r_a \cdot S_3 - M_{33} \cdot s_b \cdot b_s \cdot a_c \cdot s_a - M_{22} \cdot s_b \cdot b_c \cdot a_c \cdot r_a \cdot S_3 - M_{22} \cdot A_3 \cdot r_b \cdot b_s \cdot a_s \cdot s_a \ldots + -M_{32} \cdot s_b \cdot b_s \cdot a_s \cdot s_a \end{array}\right]$$

$$a_{13} = A_0 \cdot S_0 \cdot \frac{2 - q_a}{2} \cdot \left[\begin{array}{l} -A_1 \cdot s_b \cdot M_{12} \cdot a_c \cdot S_1 + A_1 \cdot s_b \cdot M_{12} \cdot a_s \cdot S_2 - M_{22} \cdot s_b \cdot b_c \cdot a_c \cdot S_1 + M_{22} \cdot s_b \cdot b_c \cdot a_s \cdot S_2 \ldots + -M_{22} \cdot A_3 \cdot r_b \cdot b_s \cdot a_c \cdot S_1 + M_{22} \cdot A_3 \cdot r_b \cdot b_s \cdot a_s \cdot S_2 - M_{32} \cdot s_b \cdot b_s \cdot a_c \cdot S_1 \ldots + M_{32} \cdot \\ s_b \cdot b_s \cdot a_s \cdot S_2 \ldots + -M_{32} \cdot A_3 \cdot r_b \cdot b_c \cdot a_c \cdot S_1 + M_{32} \cdot A_3 \cdot r_b \cdot b_c \cdot a_s \cdot S_2 + A_2 \cdot r_b \cdot M_{42} \cdot a_c \cdot S_1 \ldots + -A_2 \cdot r_b \cdot M_{42} \cdot a_s \cdot S_2 \ldots + A_1 \cdot s_b \cdot M_{13} \cdot a_s \cdot S_1 + A_1 \cdot s_b \cdot M_{13} \cdot a_c \cdot S_2 + M_{23} \cdot \\ s_b \cdot b_c \cdot a_s \cdot S_1 + M_{23} \cdot s_b \cdot b_c \cdot a_c \cdot S_2 \ldots + M_{23} \cdot A_3 \cdot r_b \cdot b_s \cdot a_s \cdot S_1 + M_{23} \cdot A_3 \cdot r_b \cdot b_s \cdot a_c \cdot S_2 + M_{33} \cdot s_b \cdot b_s \cdot a_s \cdot S_1 \ldots + M_{33} \cdot s_b \cdot b_s \cdot a_c \cdot S_2 + M_{33} \cdot A_3 \cdot r_b \cdot b_c \cdot a_s \cdot S_1 + M_{33} \cdot A_3 \cdot \\ r_b \cdot b_c \cdot a_c \cdot S_2 \ldots + -A_2 \cdot r_b \cdot M_{43} \cdot a_s \cdot S_1 - A_2 \cdot r_b \cdot M_{43} \cdot a_c \cdot S_2 \end{array}\right]$$

$$a_{14} = A_0 \cdot S_0 \cdot \frac{2 - q_a}{2} \cdot \left[\begin{array}{l} A_1 \cdot s_b \cdot M_{12} \cdot a_s \cdot S_1 + A_1 \cdot s_b \cdot M_{12} \cdot a_c \cdot S_2 + M_{22} \cdot s_b \cdot b_c \cdot a_s \cdot S_1 + M_{22} \cdot s_b \cdot b_c \cdot a_c \cdot S_2 \ldots + M_{22} \cdot A_3 \cdot r_b \cdot b_s \cdot a_s \cdot S_1 + M_{22} \cdot A_3 \cdot r_b \cdot b_s \cdot a_c \cdot S_2 + M_{32} \cdot s_b \cdot b_s \cdot a_s \cdot S_1 \ldots + M_{32} \cdot \\ s_b \cdot b_s \cdot a_c \cdot S_2 + M_{32} \cdot A_3 \cdot r_b \cdot b_c \cdot a_s \cdot S_1 + M_{32} \cdot A_3 \cdot r_b \cdot b_c \cdot a_c \cdot S_2 \ldots + -A_2 \cdot r_b \cdot M_{42} \cdot a_s \cdot S_1 - A_2 \cdot r_b \cdot M_{42} \cdot a_c \cdot S_2 + A_1 \cdot s_b \cdot M_{13} \cdot a_c \cdot S_1 \ldots + -A_1 \cdot s_b \cdot M_{13} \cdot a_s \cdot S_2 + M_{23} \cdot \\ s_b \cdot b_c \cdot a_c \cdot S_1 - M_{23} \cdot s_b \cdot b_c \cdot a_s \cdot S_2 \ldots + M_{23} \cdot A_3 \cdot r_b \cdot b_s \cdot a_c \cdot S_1 - M_{23} \cdot A_3 \cdot r_b \cdot b_s \cdot a_s \cdot S_2 + M_{33} \cdot s_b \cdot b_s \cdot a_c \cdot S_1 \ldots + -M_{33} \cdot s_b \cdot b_s \cdot a_s \cdot S_2 + M_{33} \cdot A_3 \cdot r_b \cdot b_c \cdot a_c \cdot S_1 - M_{33} \cdot A_3 \cdot \\ r_b \cdot b_c \cdot a_s \cdot S_2 \ldots + -A_2 \cdot r_b \cdot M_{43} \cdot a_c \cdot S_1 + A_2 \cdot r_b \cdot M_{43} \cdot a_s \cdot S_2 \end{array}\right]$$

-continued

Rotating Compensation/Rotating Compensator $$a_{20} = A_0 \cdot S_0 \cdot \left[\begin{array}{l}
M_{31} \cdot s_b \cdot b_c + A_1 \cdot r_b \cdot M_{41} + A_2 \cdot s_b \cdot M_{11} - S_3 \cdot A_2 \cdot s_b + M_{14} + S_3 \cdot M_{24} \cdot A_3 \cdot r_b \cdot b_c \ldots + S_3 \cdot M_{24} \cdot s_b \cdot b_s \cdot q_a - S_3 \cdot M_{24} \cdot s_b \cdot b_s + S_3 \cdot A_2 \cdot s_b \cdot M_{14} \cdot q_a - S_3 \cdot M_{24} \cdot A_3 \cdot r_b \cdot b_c \cdot q_a \ldots + -S_3 \cdot \\
M_{34} \cdot A_3 \cdot r_b \cdot b_s \cdot q_a + S_3 \cdot M_{34} \cdot A_3 \cdot r_b \cdot b_s + S_3 \cdot M_{34} \cdot s_b \cdot b_c \cdot q_a \ldots + \frac{1}{2} \cdot A_2 \cdot s_b \cdot M_{12} \cdot a_s \cdot q_a \cdot S_2 + \frac{1}{2} \cdot M_{22} \cdot s_b \cdot b_s \cdot a_c \cdot q_a \cdot S_1 + \frac{1}{2} \cdot A_2 \cdot s_b \cdot M_{12} \cdot a_c \cdot q_a \cdot S_1 \ldots + -M_{31} \cdot A_3 \cdot r_b \cdot b_s - \\
M_{21} \cdot A_3 \cdot r_b \cdot b_c + M_{21} \cdot s_b \cdot b_s + \frac{1}{2} \cdot A_1 \cdot r_b \cdot M_{43} \cdot a_c \cdot q_a \cdot S_2 \ldots + \frac{1}{2} \cdot M_{33} \cdot s_b \cdot b_c \cdot a_c \cdot q_a \cdot S_s - \frac{1}{2} \cdot A_1 \cdot r_b \cdot M_{43} \cdot a_s \cdot q_a \cdot S_1 \ldots + \frac{-1}{2} \cdot M_{33} \cdot A_3 \cdot r_b \cdot b_s \cdot a_c \cdot q_a \cdot S_2 + \frac{1}{2} \cdot M_{33} \cdot A_3 \cdot \\
r_b \cdot b_s \cdot a_s \cdot q_a \cdot S_1 + \frac{1}{2} \cdot A_1 \cdot r_b \cdot M_{42} \cdot a_c \cdot q_a \cdot S_1 \ldots + \frac{1}{2} \cdot M_{23} \cdot s_b \cdot b_s \cdot a_c \cdot q_a \cdot S_2 - \frac{1}{2} \cdot M_{33} \cdot s_b \cdot b_c \cdot a_s \cdot q_a \cdot S_1 - \frac{1}{2} \cdot M_{23} \cdot s_b \cdot b_s \cdot a_s \cdot q_a \cdot S_1 \ldots + \frac{-1}{2} \cdot M_{23} \cdot A_3 \cdot r_b \cdot b_c \cdot a_c \cdot q_a \cdot \\
S_2 + \frac{1}{2} \cdot A_2 \cdot s_b \cdot M_{13} \cdot a_c \cdot q_a \cdot S_2 - \frac{1}{2} \cdot A_2 \cdot s_b \cdot M_{13} \cdot a_s \cdot q_a \cdot S_1 \ldots + \frac{1}{2} \cdot A_1 \cdot r_b \cdot M_{42} \cdot a_s \cdot q_a \cdot S_2 - \frac{1}{2} \cdot M_{22} \cdot A_3 \cdot r_b \cdot b_c \cdot a_c \cdot q_a \cdot S_1 + \frac{1}{2} \cdot M_{32} \cdot s_b \cdot b_c \cdot a_s \cdot q_a \cdot S_2 \ldots + \frac{1}{2} \cdot M_{32} \cdot s_b \cdot \\
b_c \cdot a_c \cdot q_a \cdot S_1 - \frac{1}{2} \cdot M_{32} \cdot A_3 \cdot r_b \cdot b_s \cdot a_s \cdot q_a \cdot S_2 + \frac{1}{2} \cdot M_{23} \cdot A_3 \cdot r_b \cdot b_c \cdot a_s \cdot q_a \cdot S_1 \ldots + \frac{1}{2} \cdot M_{22} \cdot s_b \cdot b_s \cdot a_s \cdot q_a \cdot S_2 - \frac{1}{2} \cdot M_{22} \cdot A_3 \cdot r_b \cdot b_c \cdot a_s \cdot q_a \cdot S_2 - \frac{1}{2} \cdot M_{32} \cdot A_3 \cdot r_b \cdot b_s \cdot a_c \cdot q_a \cdot \\
S_1 \ldots + -S_3 \cdot M_{34} \cdot s_b \cdot b_c + S_3 \cdot A_1 \cdot r_b \cdot M_{44} \cdot q_a - S_3 \cdot A_1 \cdot r_b \cdot M_{44}
\end{array}\right]$$

$$a_{21} = A_0 \cdot S_0 \cdot \left[\begin{array}{l}
-s_a \cdot S_1 \cdot A_2 + s_b \cdot M_{11} + A_1 \cdot r_b \cdot M_{43} \cdot a_c \cdot r_a \cdot S_3 + r_a + S_2 \cdot M_{34} \cdot A_3 \cdot r_b \cdot b_s - r_a \cdot S_2 \cdot M_{34} \cdot s_b \cdot b_c \ldots + r_a \cdot S_2 \cdot A_1 \cdot r_b \cdot M_{44} - M_{23} \cdot A_3 \cdot r_b \cdot b_c \cdot a_c \cdot r_a \cdot S_3 + M_{23} \cdot s_b \cdot b_s \cdot a_s \cdot s_a - M_{23} \cdot A_3 \cdot \\
r_b \cdot b_c \cdot a_s \cdot s_a \ldots + A_1 \cdot r_b \cdot M_{43} \cdot a_s \cdot s_a + M_{32} \cdot s_b \cdot b_c \cdot a_s \cdot r_a \cdot S_3 - s_a \cdot S_1 \cdot A_1 \cdot r_b \cdot M_{41} - A_2 \cdot s_b \cdot M_{12} \cdot a_c \cdot s_a \ldots + -s_a \cdot S_1 \cdot M_{31} \cdot s_b \cdot b_c + s_a \cdot S_1 \cdot M_{31} \cdot A_3 \cdot r_b \cdot b_s + s_a \cdot S_1 \cdot M_{21} \cdot A_3 \cdot r_b \cdot \\
b_c - s_a \cdot S_1 \cdot M_{21} \cdot s_b \cdot b_s \ldots + M_{23} \cdot s_b \cdot b_s \cdot a_c \cdot r_a \cdot S_3 - M_{33} \cdot A_3 \cdot r_b \cdot b_s \cdot a_s \cdot s_a - M_{33} \cdot A_3 \cdot r_b \cdot b_s \cdot a_c \cdot r_a \cdot S_3 \ldots + M_{33} \cdot s_b \cdot b_c \cdot a_s \cdot s_a + A_2 \cdot s_b \cdot M_{13} \cdot a_c \cdot r_a \cdot S_3 - r_a \cdot S_2 \cdot A_2 \cdot s_b \cdot M_{14} + \\
A_1 \cdot r_b \cdot M_{42} \cdot a_s \cdot r_a \cdot S_3 \ldots + A_2 \cdot s_b \cdot M_{13} \cdot a_s \cdot s_a + -A_1 \cdot r_b \cdot M_{42} \cdot a_c \cdot s_a - r_a \cdot S_2 \cdot M_{24} \cdot s_b \cdot b_s - M_{32} \cdot A_3 \cdot r_b \cdot b_s \cdot a_s \cdot r_a \cdot S_3 \ldots + -M_{22} \cdot s_b \cdot b_s \cdot a_c \cdot s_a + M_{32} \cdot A_3 \cdot r_b \cdot b_s \cdot a_c \cdot s_a + M_{22} \cdot s_b \cdot \\
b_s \cdot a_s \cdot r_a \cdot S_3 - M_{32} \cdot s_b \cdot b_c \cdot a_c \cdot s_a \ldots + M_{22} \cdot A_3 \cdot r_b \cdot b_c \cdot a_c \cdot s_a - M_{22} \cdot A_3 \cdot r_b \cdot b_c \cdot a_s \cdot r_a \cdot S_3 + A_2 \cdot s_b \cdot M_{12} \cdot a_s \cdot r_a \cdot S_3 \ldots + M_{33} \cdot s_b \cdot b_c \cdot a_c \cdot r_a \cdot S_3 + r_a \cdot S_2 \cdot M_{24} \cdot A_3 \cdot r_b \cdot b_c
\end{array}\right]$$

$$a_{22} = A_0 \cdot S_0 \cdot \left[\begin{array}{l}
-M_{32} \cdot A_3 \cdot r_b \cdot b_s \cdot a_c \cdot r_a \cdot S_3 + M_{32} \cdot s_b \cdot b_c \cdot a_s \cdot s_a \ldots + M_{22} \cdot s_b \cdot b_s \cdot a_c \cdot r_a \cdot S_3 - M_{32} \cdot A_3 \cdot r_b \cdot b_s \cdot a_s \cdot s_a \ldots + -M_{22} \cdot A_3 \cdot r_b \cdot b_c \cdot a_c \cdot r_a + S_3 + M_{22} \cdot s_b \cdot b_s \cdot a_s \cdot s_a \ldots + r_a \cdot S_1 \cdot M_{24} \cdot A_3 \cdot \\
r_b \cdot b_c - r_a \cdot S_1 \cdot M_{24} \cdot s_b \cdot b_s \ldots + r_a \cdot S_1 \cdot M_{34} \cdot A_3 \cdot r_b \cdot b_s - r_a \cdot S_1 \cdot M_{34} \cdot s_b \cdot b_c - r_a \cdot S_1 \cdot A_1 \cdot r_b \cdot M_{44} - M_{33} \cdot s_b \cdot b_c \cdot a_s \cdot r_a \cdot S_3 \ldots + A_1 \cdot r_b \cdot M_{43} \cdot a_c \cdot s_a - A_1 \cdot r_b \cdot M_{43} \cdot a_s \cdot r_a \cdot S_3 + M_{33} \cdot \\
s_b \cdot b_c \cdot a_c \cdot s_a - r_a \cdot S_1 \cdot A_2 \cdot s_b \cdot M_{14} \ldots + -M_{23} \cdot s_b \cdot b_s \cdot a_s \cdot r_a \cdot S_3 - M_{33} \cdot A_3 \cdot r_b \cdot b_s \cdot a_c \cdot s_a \ldots + M_{33} \cdot A_3 \cdot r_b \cdot b_s \cdot a_s \cdot r_a \cdot S_3 + M_{32} \cdot s_b \cdot b_c \cdot a_c \cdot r_a \cdot S_3 \ldots + A_1 \cdot r_b \cdot M_{42} \cdot a_s \cdot s_a - A_2 \cdot \\
s_b \cdot M_{13} \cdot a_s \cdot r_a \cdot S_3 \ldots + -M_{23} \cdot A_3 \cdot r_b \cdot b_c \cdot a_c \cdot s_a + A_1 \cdot r_b \cdot M_{42} \cdot a_c \cdot r_a \cdot S_3 \ldots + A_2 \cdot s_b \cdot M_{13} \cdot a_c \cdot s_a + A_2 \cdot s_b \cdot M_{12} \cdot a_c \cdot r_a \cdot S_3 - M_{22} \cdot A_3 \cdot r_b \cdot b_c \cdot a_s \cdot s_a + s_a \cdot S_2 \cdot M_{21} \cdot s_b \cdot b_s \ldots + s_a \cdot \\
S_2 \cdot A_1 \cdot r_b \cdot M_{41} + A_2 \cdot s_b \cdot M_{12} \cdot a_s \cdot s_a + s_a \cdot S_2 \cdot M_{31} \cdot s_b \cdot b_c - s_a \cdot S_2 \cdot M_{31} \cdot A_3 \cdot r_b \cdot b_s \ldots + -s_a \cdot S_2 \cdot M_{21} \cdot A_3 \cdot r_b \cdot b_c + M_{23} \cdot A_3 \cdot r_b \cdot b_c \cdot a_s \cdot r_a \cdot S_3 \ldots + M_{23} \cdot s_b \cdot b_s \cdot a_c \cdot s_a + s_a \cdot S_2 \cdot \\
A_2 \cdot s_b \cdot M_{11}
\end{array}\right]$$

$$a_{23} = A_0 \cdot S_0 \cdot \frac{2 - q_a}{2} \cdot \left[\begin{array}{l}
A_2 \cdot s_b \cdot M_{12} \cdot a_c \cdot S_1 - A_2 \cdot s_b \cdot M_{12} \cdot a_s \cdot S_2 \ldots + -M_{22} \cdot A_3 \cdot r_b \cdot b_c \cdot a_c \cdot S_1 + M_{22} \cdot A_3 \cdot r_b \cdot b_c \cdot a_s \cdot S_2 \ldots + M_{22} \cdot s_b \cdot b_s \cdot a_c \cdot S_1 - M_{22} \cdot s_b \cdot b_s \cdot a_s \cdot S_2 \ldots + -M_{32} \cdot A_3 \cdot r_b \cdot b_s \cdot \\
a_c \cdot S_1 + M_{32} \cdot A_3 \cdot r_b \cdot b_s \cdot a_s \cdot S_2 \ldots + M_{32} \cdot s_b \cdot b_c \cdot a_c \cdot S_1 - M_{32} \cdot s_b \cdot b_c \cdot a_s \cdot S_2 + A_1 \cdot r_b \cdot M_{42} \cdot a_c \cdot S_1 - A_1 \cdot r_b \cdot M_{42} \cdot a_s \cdot S_2 \ldots + -A_2 \cdot s_b \cdot M_{13} \cdot a_s \cdot S_1 - A_2 \cdot s_b \cdot M_{13} \cdot a_c \cdot S_2 + \\
M_{23} \cdot A_3 \cdot r_b \cdot b_c \cdot a_s \cdot S_1 \ldots + M_{23} \cdot A_3 \cdot r_b \cdot b_c \cdot a_c \cdot S_2 - M_{23} \cdot s_b \cdot b_s \cdot a_s \cdot S_1 \ldots + -M_{23} \cdot s_b \cdot b_s \cdot a_c \cdot S_2 + M_{33} \cdot A_3 \cdot r_b \cdot b_s \cdot a_s \cdot S_1 \ldots + M_{33} \cdot A_3 \cdot r_b \cdot b_s \cdot a_c \cdot S_2 - M_{33} \cdot s_b \cdot b_c \cdot \\
a_s \cdot S_1 - M_{33} \cdot s_b \cdot b_c \cdot a_c \cdot S_2 \ldots + -A_1 \cdot r_b \cdot M_{43} \cdot a_s \cdot S_1 - A_1 \cdot r_b \cdot M_{43} \cdot a_c \cdot S_2
\end{array}\right]$$

$$a_{24} = A_0 \cdot S_0 \cdot \frac{2 - q_a}{2} \cdot \left[\begin{array}{l}
-A_2 \cdot s_b \cdot M_{12} \cdot a_s \cdot S_1 - A_2 \cdot s_b \cdot M_{12} \cdot a_c \cdot S_2 + M_{22} \cdot A_3 \cdot r_b \cdot b_c \cdot a_s \cdot S_1 \ldots + M_{22} \cdot A_3 \cdot r_b \cdot b_c \cdot a_c \cdot S_2 - M_{22} \cdot s_b \cdot b_s \cdot a_s \cdot S_1 \ldots + -M_{22} \cdot s_b \cdot b_s \cdot a_c \cdot S_2 + M_{32} \cdot A_3 \cdot r_b \cdot b_s \cdot \\
a_s \cdot S_1 + M_{32} \cdot A_3 \cdot r_b \cdot b_s \cdot a_c \cdot S_2 - M_{32} \cdot s_b \cdot b_c \cdot a_s \cdot S_1 \ldots + -M_{32} \cdot s_b \cdot b_c \cdot a_c \cdot S_2 - A_1 \cdot r_b \cdot M_{42} \cdot a_s \cdot S_1 \ldots + -A_1 \cdot r_b \cdot M_{42} \cdot a_c \cdot S_2 - A_2 \cdot s_b \cdot M_{13} \cdot a_c \cdot S_1 \ldots + A_2 \cdot s_b \cdot \\
M_{13} \cdot a_s \cdot S_2 + M_{23} \cdot A_3 \cdot r_b \cdot b_c \cdot a_c \cdot S_1 \ldots + -M_{23} \cdot A_3 \cdot r_b \cdot b_c \cdot a_s \cdot S_2 - M_{23} \cdot s_b \cdot b_s \cdot a_c \cdot S_1 + M_{23} \cdot s_b \cdot b_s \cdot a_s \cdot S_2 \ldots + M_{33} \cdot A_3 \cdot r_b \cdot b_s \cdot a_c \cdot S_1 - M_{33} \cdot A_3 \cdot r_b \cdot b_s \cdot a_s \cdot \\
S_2 - M_{33} \cdot s_b \cdot b_c \cdot a_c \cdot S_1 \ldots + M_{33} \cdot s_b \cdot b_c \cdot a_s \cdot S_2 - A_1 \cdot r_b \cdot M_{43} \cdot a_c \cdot S_1 + A_1 \cdot r_b \cdot M_{43} \cdot a_s \cdot S_2
\end{array}\right]$$

-continued

Rotating Compensation/Rotating Compensator $$a_{30}=A_0\cdot S_0\cdot\frac{2-q_b}{2}\cdot\left[\begin{aligned}&-M_{31}\cdot A_2\cdot b_c+M_{31}\cdot A_1\cdot b_s-M_{21}\cdot A_2\cdot b_s+M_{21}\cdot A_1\cdot b_c-S_3\cdot M_{24}\cdot A_1\cdot b_c\ldots+S_3\cdot M_{24}\cdot A_1\cdot b_c\cdot q_a+\frac{1}{2}\cdot M_{22}\cdot A_1\cdot b_c\cdot a_s\cdot q_a\cdot S_2-\frac{1}{2}\cdot M_{22}\cdot A_2\cdot b_s\cdot a_c\cdot q_a\cdot S_1\ldots+\frac{1}{2}\cdot\\&M_{33}\cdot A_1\cdot b_s\cdot a_c\cdot q_a\cdot S_2+\frac{1}{2}\cdot M_{33}\cdot A_2\cdot b_c\cdot a_s\cdot q_a\cdot S_1-\frac{1}{2}\cdot M_{33}\cdot A_1\cdot b_s\cdot a_s\cdot q_a\cdot S_1\ldots+\frac{-1}{2}\cdot M_{23}\cdot A_2\cdot b_s\cdot a_c\cdot q_a\cdot S_2+\frac{1}{2}\cdot M_{23}\cdot A_2\cdot b_s\cdot a_s\cdot q_a\cdot S_1+\frac{1}{2}\cdot M_{23}\cdot A_1\cdot\\&b_c\cdot a_c\cdot q_a\cdot S_2\ldots+\frac{-1}{2}\cdot M_{23}\cdot A_1\cdot b_c\cdot a_s\cdot q_a\cdot S_1-\frac{1}{2}\cdot M_{32}\cdot A_2\cdot b_c\cdot a_s\cdot q_a\cdot S_2-\frac{1}{2}\cdot M_{32}\cdot A_2\cdot b_c\cdot a_c\cdot q_a\cdot S_1\ldots+\frac{1}{2}\cdot M_{32}\cdot A_1\cdot b_s\cdot a_s\cdot q_a\cdot S_2+\frac{1}{2}\cdot M_{32}\cdot A_1\cdot b_s\cdot a_c\cdot\\&q_a\cdot S_1+\frac{1}{2}\cdot M_{22}\cdot A_1\cdot b_c\cdot a_c\cdot q_a\cdot S_1\ldots+-S_3\cdot M_{24}\cdot A_2\cdot b_s\cdot q_a+S_3\cdot M_{34}\cdot A_2\cdot b_c-S_3\cdot M_{34}\cdot A_1\cdot b_s-S_3\cdot M_{34}\cdot A_2\cdot b_c\cdot q_a\ldots+S_3\cdot M_{34}\cdot A_1\cdot b_s\cdot q_a+S_3\cdot M_{24}\cdot A_2\cdot b_s-\frac{1}{2}\cdot\\&M_{22}\cdot A_2\cdot b_s\cdot a_s\cdot q_a\cdot S_2\ldots+\frac{-1}{2}\cdot M_{33}\cdot A_2\cdot b_c\cdot a_c\cdot q_a\cdot S_2\end{aligned}\right]$$

$$a_{31}=A_0\cdot S_0\cdot\frac{2-q_b}{2}\cdot\left[\begin{aligned}&-s_a\cdot S_1\cdot M_{21}\cdot A_1\cdot b_c+s_a\cdot S_1\cdot M_{21}\cdot A_2\cdot b_s-s_a\cdot S_1\cdot M_{31}\cdot A_1\cdot b_s+s_a\cdot S_1\cdot M_{31}\cdot A_2\cdot b_c\ldots+-M_{22}\cdot A_1\cdot b_c\cdot a_c\cdot s_a+M_{22}\cdot A_1\cdot b_c\cdot a_s\cdot r_a\cdot S_3\ldots+M_{22}\cdot A_2\cdot b_s\cdot a_c\cdot s_a-M_{22}\cdot A_2\cdot\\&b_s\cdot a_s\cdot r_a\cdot S_3\ldots+-M_{32}\cdot A_1\cdot b_s\cdot a_c\cdot s_a+M_{32}\cdot A_1\cdot b_s\cdot a_s\cdot r_a\cdot S_3\ldots+M_{32}\cdot A_2\cdot b_c\cdot a_c\cdot s_a-M_{32}\cdot A_2\cdot b_c\cdot a_s\cdot r_a\cdot S_3\ldots+M_{23}\cdot A_1\cdot b_c\cdot a_s\cdot s_a+M_{23}\cdot A_1\cdot b_c\cdot a_c\cdot r_a\cdot S_3\ldots+\\&-M_{23}\cdot A_2\cdot b_s\cdot a_s\cdot s_a-M_{23}\cdot A_2\cdot b_s\cdot a_c\cdot r_a\cdot S_3\ldots+M_{33}\cdot A_1\cdot b_s\cdot a_s\cdot s_a+M_{33}\cdot A_1\cdot b_s\cdot a_c\cdot r_a\cdot S_3-M_{33}\cdot A_2\cdot b_c\cdot a_s\cdot s_a\ldots+-M_{33}\cdot A_2\cdot b_c\cdot a_c\cdot r_a\cdot S_3-r_a\cdot S_2\cdot M_{24}\cdot A_1\cdot b_c\ldots+\\&r_a\cdot S_2\cdot M_{24}\cdot A_2\cdot b_s-r_a\cdot S_2\cdot M_{34}\cdot A_1\cdot b_s+r_a\cdot S_2\cdot M_{34}\cdot A_2\cdot b_c\end{aligned}\right]$$

$$a_{32}=A_0\cdot S_0\cdot\frac{2-q_b}{2}\cdot\left[\begin{aligned}&s_a\cdot S_2\cdot M_{21}\cdot A_1\cdot b_c-s_a\cdot S_2\cdot M_{21}\cdot A_2\cdot b_s+s_a\cdot S_2\cdot M_{31}\cdot A_1\cdot b_s-s_a\cdot S_2\cdot M_{31}\cdot A_2\cdot b_c\ldots+M_{22}\cdot A_1\cdot b_c\cdot a_s\cdot s_a+M_{22}\cdot A_1\cdot b_c\cdot a_c\cdot r_a\cdot S_3\ldots+-M_{22}\cdot A_2\cdot b_s\cdot a_s\cdot s_a-M_{22}\cdot A_2\cdot\\&b_s\cdot a_c\cdot r_a\cdot S_3\ldots+M_{32}\cdot A_1\cdot b_s\cdot a_s\cdot s_a+M_{32}\cdot A_1\cdot b_s\cdot a_c\cdot r_a\cdot S_3\ldots+-M_{32}\cdot A_2\cdot b_c\cdot a_s\cdot s_a-M_{32}\cdot A_2\cdot b_c\cdot a_c\cdot r_a\cdot S_3\ldots+M_{23}\cdot A_1\cdot b_c\cdot a_c\cdot s_a-M_{23}\cdot A_1\cdot b_c\cdot a_s\cdot r_a\cdot S_3\ldots+\\&-M_{23}\cdot A_2\cdot b_s\cdot a_c\cdot s_a+M_{23}\cdot A_2\cdot b_s\cdot a_s\cdot r_a\cdot S_3\ldots+M_{33}\cdot A_1\cdot b_s\cdot a_c\cdot s_a-M_{33}\cdot A_1\cdot b_s\cdot a_s\cdot r_a\cdot S_3-M_{33}\cdot A_2\cdot b_c\cdot a_c\cdot s_a\ldots+M_{33}\cdot A_2\cdot b_c\cdot a_s\cdot r_a\cdot S_3-r_a\cdot S_1\cdot M_{24}\cdot A_1\cdot b_c\ldots+\\&r_a\cdot S_1\cdot M_{24}\cdot A_2\cdot b_s-r_a\cdot S_1\cdot M_{34}\cdot A_1\cdot b_s+r_a\cdot S_1\cdot M_{34}\cdot A_2\cdot b_c\end{aligned}\right]$$

$$a_{33}=A_0\cdot S_0\cdot\frac{2-q_b}{2}\cdot\frac{2-q_a}{2}\cdot\left[\begin{aligned}&M_{22}\cdot A_1\cdot b_c\cdot a_c\cdot S_1-M_{22}\cdot A_1\cdot b_c\cdot a_s\cdot S_2-M_{22}\cdot A_2\cdot b_s\cdot a_c\cdot S_1\ldots+M_{22}\cdot A_2\cdot b_s\cdot a_s\cdot S_2+M_{32}\cdot A_1\cdot b_s\cdot a_c\cdot S_1\ldots+-M_{32}\cdot A_1\cdot b_s\cdot a_s\cdot S_2-M_{32}\cdot A_2\cdot\\&b_c\cdot a_c\cdot S_1\ldots+M_{32}\cdot A_2\cdot b_c\cdot a_s\cdot S_2-M_{23}\cdot A_1\cdot b_c\cdot a_s\cdot S_1\ldots+-M_{23}\cdot A_1\cdot b_c\cdot a_c\cdot S_2+M_{23}\cdot A_2\cdot b_s\cdot a_s\cdot S_1\ldots+M_{23}\cdot A_2\cdot b_s\cdot a_c\cdot S_2-M_{33}\cdot A_1\cdot b_s\cdot a_s\cdot S_1\ldots+\\&-M_{33}\cdot A_1\cdot b_s\cdot a_c\cdot S_2+M_{33}\cdot A_2\cdot b_c\cdot a_s\cdot S_1\ldots+M_{33}\cdot A_2\cdot b_c\cdot a_c\cdot S_2\end{aligned}\right]$$

$$a_{34}=A_0\cdot S_0\cdot\frac{2-q_b}{2}\cdot\frac{2-q_a}{2}\cdot\left[\begin{aligned}&-M_{22}\cdot A_1\cdot b_c\cdot a_s\cdot S_1-M_{22}\cdot A_1\cdot b_c\cdot a_c\cdot S_2+M_{22}\cdot A_2\cdot b_s\cdot a_s\cdot S_1\ldots+M_{22}\cdot A_2\cdot b_s\cdot a_c\cdot S_2-M_{32}\cdot A_1\cdot b_s\cdot a_s\cdot S_1-M_{32}\cdot A_1\cdot b_s\cdot a_c\cdot S_2\ldots+M_{32}\cdot A_2\cdot b_c\cdot\\&a_s\cdot S_1+M_{32}\cdot A_2\cdot b_c\cdot a_c\cdot S_2-M_{23}\cdot A_1\cdot b_c\cdot a_c\cdot S_1\ldots+M_{23}\cdot A_1\cdot b_c\cdot a_s\cdot S_2+M_{23}\cdot A_2\cdot b_s\cdot a_c\cdot S_1-M_{23}\cdot A_2\cdot b_s\cdot a_s\cdot S_2\ldots+-M_{33}\cdot A_1\cdot b_s\cdot a_c\cdot S_1\ldots+\\&M_{33}\cdot A_1\cdot b_s\cdot a_s\cdot S_2+M_{33}\cdot A_2\cdot b_c\cdot a_c\cdot S_1-M_{33}\cdot A_2\cdot b_c\cdot a_s\cdot S_2\end{aligned}\right]$$

$$a_{40}=A_0\cdot S_0\cdot\frac{2-q_b}{2}\cdot\left[\begin{aligned}&-M_{31}\cdot A_1\cdot b_c-M_{31}\cdot A_2\cdot b_s-M_{21}\cdot A_1\cdot b_s-M_{21}\cdot A_2\cdot b_c-\frac{1}{2}\cdot M_{33}\cdot A_1\cdot b_c\cdot a_c\cdot q_a\cdot S_2\ldots+\frac{1}{2}\cdot M_{33}\cdot A_1\cdot b_c\cdot a_s\cdot q_a\cdot S_1-\frac{1}{2}\cdot M_{33}\cdot A_2\cdot b_s\cdot a_c\cdot q_a\cdot S_2+\frac{1}{2}\cdot M_{33}\cdot A_2\cdot b_s\cdot\\&a_s\cdot q_a\cdot S_1\ldots+-\frac{1}{2}\cdot M_{23}\cdot A_1\cdot b_s\cdot a_c\cdot q_a\cdot S_2+S_3\cdot M_{34}\cdot A_1\cdot b_c\ldots+-S_3\cdot M_{34}\cdot A_1\cdot b_c\cdot q_a-S_3\cdot M_{34}\cdot A_2\cdot b_s\cdot q_a\ldots+-S_3\cdot M_{24}\cdot A_1\cdot b_s\cdot q_a+\frac{1}{2}\cdot M_{23}\cdot A_1\cdot b_s\cdot a_s\cdot q_a\cdot S_1-\\&\frac{1}{2}\cdot M_{23}\cdot A_2\cdot b_c\cdot a_c\cdot q_a\cdot S_2\ldots+-S_3\cdot M_{24}\cdot A_2\cdot b_c\cdot q_a+\frac{1}{2}\cdot M_{23}\cdot A_2\cdot b_c\cdot a_s\cdot q_a\cdot S_1-\frac{1}{2}\cdot M_{32}\cdot A_1\cdot b_c\cdot a_s\cdot q_a\cdot S_2\ldots+S_3\cdot M_{34}\cdot A_2\cdot b_s+S_3\cdot M_{24}\cdot A_1\cdot b_s-\frac{1}{2}\cdot M_{32}\cdot\\&A_1\cdot b_c\cdot a_c\cdot q_a\cdot S_1\ldots+\frac{-1}{2}\cdot M_{32}\cdot A_2\cdot b_s\cdot a_s\cdot q_a\cdot S_2\ldots+\frac{-1}{2}\cdot M_{32}\cdot A_2\cdot b_s\cdot a_c\cdot q_a\cdot S_1-\frac{1}{2}\cdot M_{22}\cdot A_1\cdot b_s\cdot a_s\cdot q_a\cdot S_2+S_3\cdot M_{24}\cdot A_2\cdot b_c\ldots+\frac{-1}{2}\cdot M_{22}\cdot A_1\cdot b_s\cdot\\&a_c\cdot q_a\cdot S_1-\frac{1}{2}\cdot M_{22}\cdot A_2\cdot b_c\cdot a_s\cdot q_a\cdot S_2-\frac{1}{2}\cdot M_{22}\cdot A_2\cdot b_c\cdot a_c\cdot q_a\cdot S_1\end{aligned}\right]$$

-continued

Rotating Compensation/Rotating Compensator $$a_{41} = A_0 \cdot S_0 \cdot \frac{2-q_b}{2} \cdot \left[ \begin{array}{l} s_a \cdot S_1 \cdot M_{21} \cdot A_2 \cdot b_c + s_a \cdot S_1 \cdot M_{21} \cdot A_1 \cdot b_s + s_a \cdot S_1 \cdot M_{31} \cdot A_2 \cdot b_s + s_a \cdot S_1 \cdot M_{31} \cdot A_1 \cdot b_c \ldots + M_{22} \cdot A_2 \cdot b_c \cdot a_c \cdot s_a - M_{22} \cdot A_2 \cdot b_c \cdot a_s \cdot r_a \cdot S_3 \ldots + M_{22} \cdot A_1 \cdot b_s \cdot a_c \cdot s_a - \\ M_{22} \cdot A_1 \cdot b_s \cdot a_s \cdot r_a \cdot S_3 \ldots + M_{32} \cdot A_2 \cdot b_s \cdot a_c \cdot s_a - M_{32} \cdot A_2 \cdot b_s \cdot a_s \cdot r_a \cdot S_3 + M_{32} \cdot A_1 \cdot b_c \cdot a_c \cdot s_a \ldots + -M_{32} \cdot A_1 \cdot b_c \cdot a_s \cdot r_a \cdot S_3 - M_{23} \cdot A_2 \cdot b_c \cdot a_s \cdot s_a - M_{23} \cdot A_2 \cdot b_c \cdot \\ a_c \cdot r_a \cdot S_3 \ldots + -M_{23} \cdot A_1 \cdot b_s \cdot a_s \cdot s_a - M_{23} \cdot A_1 \cdot b_s \cdot a_c \cdot r_a \cdot S_3 \ldots + -M_{33} \cdot A_2 \cdot b_s \cdot a_s \cdot s_a - M_{33} \cdot A_2 \cdot b_s \cdot a_c \cdot r_a \cdot S_3 \ldots + -M_{33} \cdot A_1 \cdot b_c \cdot a_s \cdot s_a - M_{33} \cdot A_1 \cdot b_c \cdot \\ a_c \cdot r_a \cdot S_3 \ldots + r_a \cdot S_2 \cdot M_{24} \cdot A_2 \cdot b_c + r_a \cdot S_2 \cdot M_{24} \cdot A_1 \cdot b_s \ldots + r_a \cdot S_2 \cdot M_{34} \cdot A_2 \cdot b_s + r_a \cdot S_2 \cdot M_{34} \cdot A_1 \cdot b_c \end{array} \right]$$

$$a_{42} = A_0 \cdot S_0 \cdot \frac{2-q_b}{2} \cdot \left[ \begin{array}{l} -s_a \cdot S_2 \cdot M_{21} \cdot A_2 \cdot b_c - s_a \cdot S_2 \cdot M_{21} \cdot A_1 \cdot b_s - s_a \cdot S_2 \cdot M_{31} \cdot A_2 \cdot b_s - s_a \cdot S_2 \cdot M_{31} \cdot A_1 \cdot b_c \ldots + -M_{22} \cdot A_2 \cdot b_c \cdot a_s \cdot s_a - M_{22} \cdot A_2 \cdot b_c \cdot a_c \cdot r_a \cdot S_3 \ldots + -M_{22} \cdot A_1 \cdot b_s \cdot a_s \cdot s_a - \\ M_{22} \cdot A_1 \cdot b_s \cdot a_c \cdot r_a \cdot S_3 - M_{32} \cdot A_2 \cdot b_s \cdot a_s \cdot s_a \ldots + -M_{32} \cdot A_2 \cdot b_s \cdot a_c \cdot r_a - S_3 - M_{32} \cdot A_1 \cdot b_c \cdot a_s \cdot s_a - M_{32} \cdot A_1 \cdot b_c \cdot a_c \cdot r_a \cdot S_3 \ldots + -M_{32} \cdot A_2 \cdot b_c \cdot a_c \cdot s_a + M_{23} \cdot A_2 \cdot b_c \cdot a_s \cdot \\ r_a \cdot S_3 - M_{23} \cdot A_1 \cdot b_s \cdot a_c \cdot s_a \ldots + M_{23} \cdot A_1 \cdot b_s \cdot a_s \cdot r_a \cdot S_3 - M_{23} \cdot A_2 \cdot b_s \cdot a_c \cdot s_a + M_{33} \cdot A_2 \cdot b_s \cdot a_s \cdot r_a \cdot S_3 \ldots + -M_{33} \cdot A_1 \cdot b_c \cdot a_c \cdot s_a + M_{33} \cdot A_1 \cdot b_c \cdot a_s \cdot r_a \cdot S_3 \ldots + r_a \cdot \\ S_1 \cdot M_{24} \cdot A_2 \cdot b_c \cdot r_a \cdot S_1 + M_{24} \cdot A_1 \cdot b_s + r_a \cdot S_1 \cdot M_{34} \cdot A_2 \cdot b_s + r_a \cdot S_1 \cdot M_{34} \cdot A_1 \cdot b_c \end{array} \right]$$

$$a_{43} = A_0 \cdot S_0 \cdot \frac{2-q_b}{2} \cdot \frac{2-q_a}{2} \cdot \left[ \begin{array}{l} -M_{22} \cdot A_2 \cdot b_c \cdot a_c \cdot S_1 + M_{22} \cdot A_2 \cdot b_c \cdot a_s \cdot S_2 - M_{22} \cdot A_1 \cdot b_s \cdot a_c \cdot S_1 \ldots + M_{22} \cdot A_1 \cdot b_s \cdot a_s \cdot S_2 - M_{32} \cdot A_2 \cdot b_s \cdot a_c \cdot S_1 + M_{32} \cdot A_2 \cdot b_s \cdot a_s \cdot S_2 \ldots + -M_{32} \cdot A_1 \cdot b_c \cdot \\ a_c \cdot S_1 + M_{32} \cdot A_1 \cdot b_c \cdot a_s \cdot S_2 + M_{23} \cdot A_2 \cdot b_c \cdot a_s \cdot S_1 \ldots + M_{23} \cdot A_2 \cdot b_c \cdot a_c \cdot S_2 + M_{23} \cdot A_1 \cdot b_s \cdot a_s \cdot S_1 + M_{23} \cdot A_1 \cdot b_s \cdot a_c \cdot S_2 \ldots + M_{33} \cdot A_2 \cdot b_s \cdot a_s \cdot S_1 + M_{33} \cdot A_2 \cdot \\ b_s \cdot a_c \cdot S_2 + M_{33} \cdot A_1 \cdot b_c \cdot a_s \cdot S_1 \ldots + M_{33} \cdot A_1 \cdot b_c \cdot a_c \cdot S_2 \end{array} \right]$$

$$a_{44} = A_0 \cdot S_0 \cdot \frac{2-q_b}{2} \cdot \frac{2-q_a}{2} \cdot \left[ \begin{array}{l} M_{22} \cdot A_2 \cdot b_c \cdot a_s \cdot S_1 + M_{22} \cdot A_2 \cdot b_c \cdot a_c \cdot S_2 + M_{22} \cdot A_1 \cdot b_s \cdot a_s \cdot S_1 \ldots + M_{22} \cdot A_1 \cdot b_s \cdot a_c \cdot S_2 + M_{32} \cdot A_2 \cdot b_s \cdot a_s \cdot S_1 + M_{32} \cdot A_2 \cdot b_s \cdot a_c \cdot S_2 \ldots + M_{32} \cdot A_1 \cdot b_c \cdot a_s \cdot S_1 + \\ M_{32} \cdot A_1 \cdot b_c \cdot a_c \cdot S_2 \ldots + M_{23} \cdot A_2 \cdot b_c \cdot a_c \cdot S_1 - M_{23} \cdot A_2 \cdot b_c \cdot a_s \cdot S_2 + M_{23} \cdot A_1 \cdot b_s \cdot a_c \cdot S_1 \ldots + -M_{23} \cdot A_1 \cdot b_s \cdot a_s \cdot S_2 + M_{33} \cdot A_2 \cdot b_s \cdot a_c \cdot S_1 - M_{33} \cdot A_2 \cdot b_s \cdot a_s \cdot \\ S_2 \ldots + M_{33} \cdot A_1 \cdot b_c \cdot a_c \cdot S_1 - M_{33} \cdot A_1 \cdot b_c \cdot a_s \cdot S_2 \end{array} \right]$$

CALIBRATION PARAMETER CONTAINING EQUATION REGRESSION DIRECTLY ONTO MEASURED INTENSITY VALUES

It is also to be appreciated that while requiring more computation time, any of the described approaches, (ie. (RPRA), (RPRC),(RARC) and (RCRC)), to evaluating Calibration Parameters which Compensate Non-Idealities in Mathematical Representations of Rotated and Non-Rotated Components of a Sample System Investigating System, can be performed without the intermediate step involving Multiple Fourier Series Coefficient Values provided from empirically measured data, and Analytically Determining Calibration Parameter Containing Equations for each said Multiple Fourier Series Coefficient. That is, a Regression can be performed on Directly Empirically Measured Intensity Values and Analytically Derived Analogically Equivalent Calibration Parameter containing Equations therefore. Said Analogically equivalent Derived Equations can be arrived at by a straight forward multiplication of a properly sequenced series of Matrix representations for a specific Sample System Investigating System. Said Analytically Derived Analogically equivalent Calibration Parameter containing Equations can be of any form, such as a Multiple Fourier, or other Mathematical Series. As presented infra, in the "GENERALIZED ELLIPSOMETER OR POLARIMETER SYSTEM" herein by Eqs. 1 & 4, such an Intensity Equation can be generally represented as:

$$I(\Theta a,\Theta b) = A*R(\Theta b)*Mb(-\Theta b)*R(-\Theta bs)*Ms*R(\Theta as)*R(\Theta a)*Ma*R(-\Theta a)*S; \qquad \text{EQ. 1}$$

$$\begin{aligned} I(\Theta a,\Theta b) = {} & a00 + a01*COS(2\Theta a) + a02*SIN(2\Theta a) + \qquad \text{EQ. 4} \\ & a03*COS(4\Theta a) + a04*SIN(4\Theta a) + a10*COS(2\Theta b) + \\ & a11*COS(2\Theta b)*COS(2\Theta a) + a12*COS(2\Theta b)*SIN(2\Theta a) + \\ & a13*COS(2\Theta b)*COS(4\Theta a) + a14*COS(2\Theta b)*SIN(40a) + \\ & a20*SIN(2\Theta b) + a21*SIN(2\theta b)*COS(2\Theta a) + \\ & a22*SIN(2\Theta b)*SIN(2\Theta a) + a23*SIN(2\Theta b)*COS(4\Theta a) + \\ & a24*SIN(2\Theta b)*SIN(40a) + a30*COS(4\Theta b) + \\ & a31*COS(4\Theta b)*COS(2\Theta a) + a32*COS(4\Theta b)*Sin(2\Theta a) + \\ & a33*COS(4\Theta b)*COS(4\Theta a) + a34*COS(4\Theta b)*SIN(4\Theta a) + \\ & a40*SIN(4\Theta b) + a41*SIN(4\Theta b)*COS(2\Theta a) + \\ & a42*SIN(4\Theta b)*SIN(2\Theta a) + a43*SIN(4\Theta b)*COS(4\Theta a) + \\ & a44*SIN(4\Theta b)*SIN(4\Theta a). \end{aligned}$$

where I(θa, θb) is an Intensity and where Θa and Θb are Azimuthal Rotation angles of two Sample System Investigating System Components and application of said equations is also identified by wavelength utilized.

This Method of Calibrating a Sample System Investigating System described directly is also applicable to Ellipsometers and Polarimeters which can be sequentially comprised of a Source of a Beam of Electromagnetic wavelengths, a Polarizer means, typically for imposing a state of polarization upon said Beam of Electromagnetic wavelengths, a Stage for supporting a Sample System, an Analyzer means, typically for selecting a state of polarization in said Beam of Electromagnetic wavelengths and a Detector System. In addition, such a Sample System Investigating System can be further comprised of at least a First Compensator means, said at least a First Compensator means being positioned in said Sample System Investigating System at a location selected from the group consisting of, before and after, said Stage for supporting said Sample System. The Sample System Investigating System can also optionally comprise a Second Compensator means positioned in said Sample System Investigating System at a location complementary to said First Compensator means, said position being selected from the group consisting of, respectively, after and before, said Stage for supporting said Sample System.

An exemplary Intensity Equation Based Calibration Method comprises the steps of:

Step a. Empirically obtaining Intensity Value data sets measured by said Detector system, said Intensity value Data Sets being a function of wavelength and of rotated settings of Azimuthal angles of at least two of said Sample System Investigating System components, which Sample System Investigating System components are selected from the group consisting of said Polarizer means, said Analyzer means and present Compensator means. At least one of which Intensity value Data Sets is obtained with said Sample System Investigating System oriented in a "Sample Present" configuration and at least one of which Data Sets is obtained with said Sample System Investigating System oriented in a configuration selected from the group consisting of an "Alternative Sample-Present" configuration and a "Straight-Through" configuration. Said "Straight-Through" configuration resulting from orienting said Sample System Investigating System such that a Beam of Electromagnetic wavelengths provided by said Source of a Beam of Electromagnetic wavelengths is caused to pass through said Polarization means, through said Analyzer means and into said Detector system. And said "Sample-Present" configuration resulting from orienting said Sample System Investigating System such that a Beam of Electromagnetic wavelengths provided by said Source of a Beam of Electromagnetic wavelengths is caused to pass through said Polarization means, interact with an arbitrary Sample System supported by said Stage for supporting a Sample System, pass through said Analyzer means and into said Detector system. In either of said "Straight-Through" or "Sample-Present" configurations of said Sample System investigating system, said Beam of Electromagnetic wavelengths is also caused to pass through present Compensator means.

Step b. Effectively deriving Analytical Non-ideality Compensating Calibration Parameter containing Intensity Equations for said Sample System Investigating System which correspond to each of said empirically obtained Intensities, such as by multiplying Calibration Parameter containing Matrix representations of each Sample System Investigating System Component, and Rotation Matrices, in a Sample System Investigating System representing sequence.

Step c. Performing a simultaneous Mathematical Regression of the empirically obtained Intensity values and the effectively Analytically derived Calibration Parameter containing equations obtained in steps a. and b.

The end result being that Non-Ideality Compensating Calibration Parameters in said effective Non-Ideality Compensating Calibration Parameter containing Analytically Derived Equations are simultaneously Evaluated, based upon an error reducing criteria.

Said method of Calibrating a Sample System Investigating System can further comprise, in conjunction with Step a., the obtaining of at least one additional Intensity Value Data Set measured by said Detector system, which Intensity values are a function of the rotated settings of Azimuthal angles of at least two of said Sample System Investigating System components in said Sample System Investigating System, which at least one additional Data Set is/are however, obtained from a Sample System investigation system configuration selected from the group consisting of; (wherein at least one of the Sample System Investigating System components originally present, is removed, and wherein an "Alternative Sample-System" replaces a "Sample-System" previously present. The obtaining of said at least one additional Intensity Value Data Set being followed by the effective Derivation of Analytical Non-Ideality Compensating Calibration Parameter containing Equation (s) corresponding to said at least one additional Data Set of Intensity Values and including said additional Empirically Determined Intensity Values and effective analogically equivalent Analytical Derived Non-Ideality Compensating Calibration Parameter containing equation(s) in the simultaneous Mathematical Regression in Step c.

The purpose of said additional Data Set being to allow obtaining Component Individuated PSI and DELTA'S of the Components of a "Lumped" combination of Sample System Investigating System Components, such as a Compensator and a "Sample-System" per se. in a (RPRA) system. In said case said "Sample-System" and said Compensator retain a constant Azimuthal Angle with respect to one another during investigation, thereby making the "Sample-System" and Compensator appear as a single Component. The "Sample-System" Investigating System Component removed in said case, while obtaining said additional Data Set, is then the Compensator. Alternatively an "Alternative Sample-System" could replace the previously present "Sample-System".

It is to be understood that suitable error reducing criteria for use in any foregoing described Mathematical Regression, include Least-Square Error and Mean-Square Error techniques wherein values of variable Calibration Parameters are simultaneously varied to the end that errors between measured data and data calculated from an analogically corresponding Analytically effectively derived equation are reduced. Such techniques are well known in the literature, with one rather suitable one being known as the "Marquard-Levenburg" technique.

APPLICATION OF CALIBRATED IR ELLIPSOMETER SYSTEM TO CHARACTERIZE SAMPLES

In use, said Calibrated System Component Characterizing Matrices are utilized to allow calculation of PSI and DELTA, (or perhaps Mueller Matrix), values which characterize the optical and microstructural physical properties of Sample Systems under investigation. However, in evaluating the PSI and DELTA values of Sample-Systems, Empirical Data is typically collected with only one Rotatable Element set in Rotation, (preferably the Compensator means, but possibly the Polarizer means or Analyzer means). In addition, Sample System Characterizing PSI and DELTA, (or Mueller Matrix), Data is acquired at a number, (eg. three (3)), Angles of Incidence of the Investigating Polarized Electromagnetic Beam to the normal to the Sample System Surface. It is possible, however, to collect Data while two Ellipsometer or Polarimeter etc. System Components are rotated.

It is to be noted that Sample System Characterization, (eg. PSI and DELTA), determination can be achieved after acquiring the above described data by use of WVASE (Registered Trademark of J. A. Woollam Co. Inc.) Software, (and/or its various upgrades). The Application manual for said Software is published by distribution to customers of the J. A. Woollam Co. Inc. and is available at the J. A. Woollam CO. Inc. Said WVASE(™) Instruction Manual is incorporated by reference herein.

Another aspect of the present invention which requires mention is that use of a dual Rotating Component, (eg. RCRC), configuration during data acquisition, (rather than a single Rotating Component configuration), allows investigation of Anisotropic and Depolarizing Sample Systems because the elements of a Sample System representing Mueller Matrix can be achieved, rather than simple PSI and DELTA values for a Sample System.

The present invention will be better understood, especially as regards the by geometrical shape of the preferred Compensator, by reference to the Detailed Description Section of this Disclosure, and the accompanying Drawings.

SUMMARY OF THE INVENTION

It is therefore a primary purpose of the present invention to provide an IR Ellipsometer or Polarimeter System for use in investigating Sample Systems with Electromagnetic Wavelenghts in the Infrared range.

It is yet another primary purpose of the present invention to teach a Method of Calibrating Mathematical Representations of IR Ellipsometer/Polarimeter System Components, (eg. Electromagnetic Wave Source, Polarizer means, Compensator means, Analyzer means, and Detector), for Non-Idealities in said Rotated and Non-Rotated IR Ellipsometer System Components, which Nonidealities become especially pronounced when Infrared Range Wavelengths are utilized. Said Method involves error reducing regression based evaluation of Calibration Parameters present in typically Matrix Multiplication provided analytically derived equations, and said regression being onto empirically obtained analogically corresponding data.

Additional purposes will become evident by reference to other portions of this Disclosure.

DETAILED DESCRIPTION

Figure 1A:
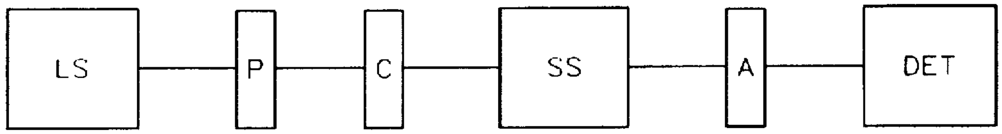
FIG. 1*a* is a diagramatic representation of one configuration of the present invention system.
Figure 1B:
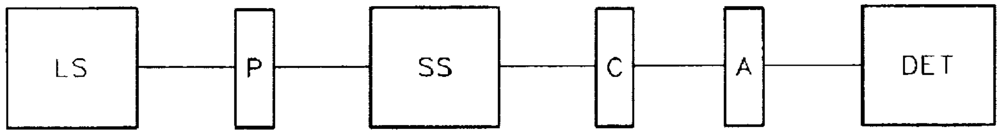
FIG. 1*b* is a diagramatic representation of an alternative configuration of the present invention system.

Turning now to the Drawings, there is shown diagramatically, in FIGS. 1*a* and 1*b*, two demonstrative variations of the system of the present invention. FIG. 1*a* shows a Source of Infrared light, (LS), (eg. a Michaelson Blackbody Continuous IR Wavelength Source), followed in sequence by a Polarizer means (P), a Compensator means (C), a Sample System (SS), an Analyzer means (A) and a Detector System (DET). FIG. 1*b* is similar except that the Compensator means (C) is shown after, rather than before the Sample System (SS). While FIGS. 1*a* and 1*b* show two major present invention System Configurations, it is to be understood that other system configurations are also within the scope of the present invention. For instance, another particularly relevant present invention System Configuration provides that two Compensator means be present, one before and one after a Sample System (SS).

Figure 1C:
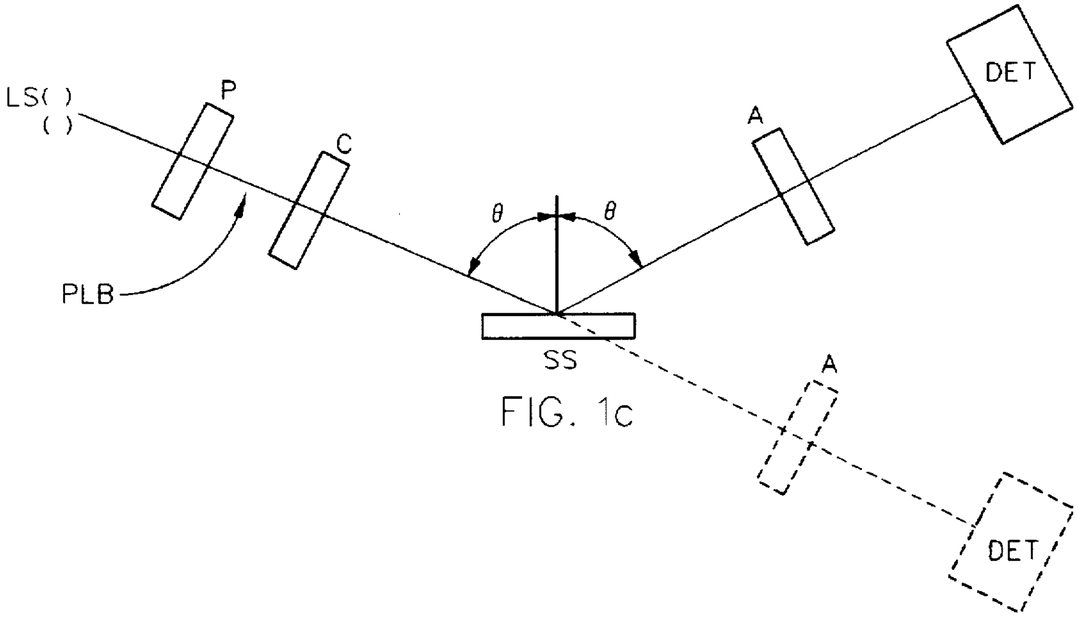
FIG. 1*c* is a more geometrically revealing representation of the present invention system shown in FIG. 1*a*.

FIG. 1*c* shows a more geometrically correct representation of the system of a present invention System Configuration when configured to investigate a Sample System (SS). The Light Source (LS) typically provides essentially unpolarized Electromagnetic Wavelengths in the Infrared range. Some of said Electromagnetic Wavelengths are caused to pass through a Polarizer means (P) and emerge therefrom as a Polarized Beam of Electromagnetic Wavelengths (PLB), which Polarized Beam of Electromagnetic Wavelengths (PLB) is directed so as to pass through a Compensator means (C). Said Polarizer means (P), (and said Compensator means (C)), serve to impose a State of Polarization upon said Beam of Electromagnetic Wavelengths prior to its being directed to impinge upon a Sample System (SS) at an Angle of Incidence (AOI) (θ) to a normal to the surface thereof. Said Polarized Beam of Electromagnetic Wavelengths is shown to then reflect from, (transmit through), said Sample System (SS), pass through an Analyzer means (A), and enter a Detector System (DET), wherein a signal representative of the Intensity of said Beam of Polarized Electromagnetic Wavelengths entering thereto is developed.

Figure 1D:
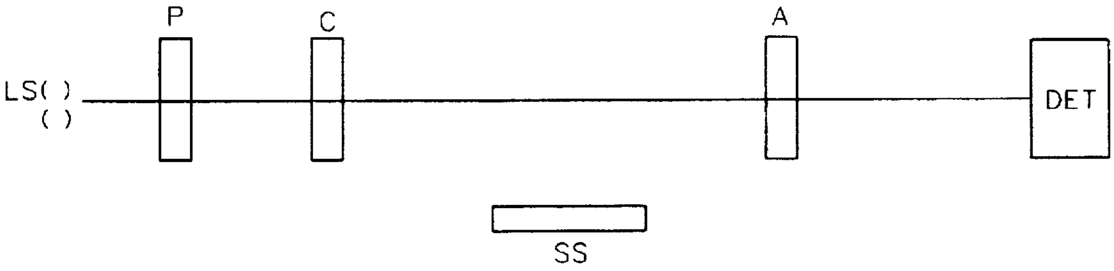
FIG. 1*d* is a more geometrically revealing representation of the present invention system shown in FIG. 1*a*, oriented in a "straight-through" configuration.

FIG. 1*d* shows the system of FIG. 1*c*, oriented in a "Straight-Through" configuration wherein said Polarized Beam of Electromagnetic Wavelengths (PLB) is not caused to interact with a Sample System (SS), but rather passes from said Compensator means (C) directly through said Analyzer means (A) and into said Detector System (DET).

It is to be understood that FIGS. 1*c* and 1*d* are directly derived from the IR Ellipsometer System shown in FIG. 1*a*. It is to be understood that a similar set of Figures could be presented which would derive from FIG. 1*b*. That is the Compensator means (C) could also be shown following a Sample System (SS) in Figures similar to FIGS. 1*c* and 1*d*, or Compensator means (C) could be present both before and after a Sample System (SS).

As described in the Disclosure of the Invention Section herein, both the configurations such as represented by FIGS. 1*c*, (Sample System (SS) present), and 1*d*, (Straight Through), are typically utilized in Calibrating the present invention IR Ellipsometer System. Said Disclosure of the Invention Section herein also makes clear that, typically, two of the present invention System Components (eg. selected from the group consisting of the Polarizer means (P), one or two Compensator means (C) and Analyzer means (A) are caused to be stepwise rotated during said Calibration Procedure), with Intensity readings being obtained at a multiplicity of Azimuthal Angle Settings of each of said Rotated Components. Said Intensity measurements are utilized to determine Element Values in a Two Dimensional Matrix, which Two (2) Dimensional Matrix Elements represents a Coefficients of a Double Fourier Series. (The equations which allow arriving at said Two (2) Dimensional Matrix Double Fourier Series Element representing values, utilizing said measured Intensity values at said multiplicity Azimuthal settings of each of two present invention System Components, are provided in said Disclosure of the Invention Section herein). Following determination of said Two (2) Dimensional Matrix Element Values, one said Matrix Element value is typically chosen, (eg. the Matrix Element corresponding to the product of Fourier Series D.C. Terms from the two (2) Fourier Series represented), and the remaining Element Values normalized thereto. The present invention Calibration Procedure provides that Two (2) Dimensional Matrices be produced at a multiplicity of Wavelengths.

The Calibration Procedure, it must be appreciated, serves to arrive at values of Calibration Parameters in Matrix Element Value Determining Equations, which Matrices Mathematically represent various present invention System Components, or Lumped Combinations of present invention System Components. Matrix Element Determining Mathematical Equations containing said Compensating Calibration Parameters are obtained by performing Matrix Multiplication of IR Ellipsometer System Matrices which represent present invention IR Ellipsometer System Components, said Matrix Multiplication being performed in an order appropriate for a utilized present invention IR Ellipsometer System Configuration, (eg. two of which Configurations are shown by FIGS. 1*a* and 1*b*). (Note that Rotation Matrices are also included in said Matrix Multiplication Procedure, which Rotation Matrices serve to place a Polarized Electromagnetic Beam exiting one IR Ellipsometer System Component in an Azimuth appropriate for application to a succeeding IR Ellipsometer System Component. For instance, a Rotation Matrix would be present between said Polarizer representing Matrix and said Compensator representing Matrix, and another Rotation Matrix would be present between said Compensator representing Matrix and said Sample System representing Matrix and so on). Now, said present invention System Component Compensating Calibration Parameter containing Matrix Element Defining Mathematical Equations arrived at by said Matrix Multiplication, are analogically associated with Numerical Values for Elements in an Empirically arrived at Two (2) Dimensional Matrix, and regression of said Calibration Parameter containing Mathematical Equations which determine Matrix Elements, onto analogically corresponding Elements in said Two (2) Dimensional Empirically Determined Matrix Element Values allows obtaining a simultaneous reduced Square Error fit to said Calibration Parameters. (Typically, in present invention practice, a Mean Square Error reducing approach has been practiced).

To understand why the described Calibration procedure works, it must be understood that said Calibration Parameter containing Mathematical Equations arrived at by multiplication of IR Ellipsometer System Component representing Matrices are in fact representations of Coefficients of terms, typically in a Two Dimensional Fourier Series, (other mathematical series could be utilized), and Said Calibration Parameter containing Equations are analogically equivalent to Elements in said Empirically arrived at Two (2) Dimensional Matrix. To better describe why said approach is valid, it is to be understood that each Empirically determined Two (2) Dimensional Matrix could be expanded into a series of Terms, each of which has one of the (Normalized) Empirically arrived at Matrix Element Values associated therewith as a Coefficient. An analogically similar series of terms can also be arrived at by Matrix multiplication of IR Ellipsometer System Component representing, and Rotation, Matrices, in an appropriate IR Ellipsometer System representing order. Simple comparison of the two resulting summation of terms series which result will easily show which Empirically arrived at Two (2) Dimensional Matrix Elements, and Calibration Parameter containing IR Ellipsometer System Matrix Element Determining Mathematical Equations resulting from said Matrix Multiplication of System Component Representing, and Rotation, Matrices, are analogically similar. It is pointed out that the present invention Method does not require that said analogically similar summation of terms series be actually determined. The preferred embodiment of the present invention arrives at Calibration Parameter containing Matrix Element Determining Mathematical Equations which are analogically equivalent to Empirically determined Values for Elements in a Two Dimensional Fourier Series representing Matrix, by an approach which reduces the complexity of the mathematics involved. This is better described in the Disclosure of the Invention Section herein.

For convenience, FIGS. *6a* and *6b* provide Flow Charts for the Calibration Procedure of the present invention. The right hand side column in each is focused on derivation of an IR Ellipsometer System Matrix Based Theoretical Model, effective Equations for Elements of which IR Ellipsometer System representing Matrices contain Calibration Parameters. The Matrix Element Determining Equations represent Fourier Series Coefficients in the FIG. *6a* diagram and Intensities in the FIG. *6b* diagram. The left hand column in each of FIGS. *6a* and *6b* identifies a Measurement based Empirical approach to obtaining Double Fourier Series Matrix Elements, or simply Intensity values respectively, which in practice are simply Numerical Values determined from measured Intensity Values for various Azimuthal Angle settings of two (2) IR Ellipsometer System Components. (Note, the terminology Fourier Elements is with respect to FIG. *6a*, rather than Fourier Coefficient, only because the terms on point are Elements in Matrices). Next, regarding the FIG. *6a* diagram, analogically corresponding Empirically determined Double Fourier Series Matrix Element Numerical Values, and effective Analytically derived IR Ellipsometer System Matrix Element Determining Equations which contain Calibration Parameters, are simultaneously subjected to a Regression Procedure, (eg. Levenberg-Marquard), and Numerical Values obtained for the various Calibration Parameters. Regarding the FIG. *6b* diagram, it is simply the measured Intensity values and analogically equivalent effective Analytically derived Calibration Parameters containing Equations which are subjected to the simultaneous Mathematical Regression Procedure. Once acceptable Numerical Values for the various Calibration Parameters are obtained by application of said Regression Procedure, said Numerical Values are assigned to said Calibration Parameters in the IR Ellipsometer System Representing Matrices containing them, in appropriate Elements thereof. Thus are arrived at Shell Form Matrices for each IR Ellipsometer System Component. That is, a Calibrated Matrix Based Mathematical Model for each IR Ellipsometer System Component, (eg. Polarizer means (P), Compensator means (C), Analyzer means (A)), in the IR Ellipsometer System, which IR Ellipsometer System Component Representing Matrices are each Calibrated for Non-idealities associated with each said IR Ellipsometer System Component.

Note that said Calibration Procedure, in either the FIG. *6a* or *6b* approach, serves to simultaneously provide numerical values for Calibration Parameters in both Rotated and Non-Rotated Sample System Investigating System Component representing Matrices.

With said Matrix based Mathematical Model available it becomes possible to calculate what the response of the IR Ellipsometer System should be to a Polarized Electromagnetic Beam. When a Sample System (SS) is then investigated by the IR Ellipsometer System, and Theoretically and Empirically obtained data are subjected to a Regression Procedure, values for Sample System (SS) characterizing PSI and DELTA Values, (at specified Wavelengths and Angles Of Incidence of a Polarized Electromagnetic Beam), can be accurately obtained. It should be noted that Utilization of the Calibrated IR Ellipsometer System is, thus, not significantly different from utilization of any other Ellipsometer System once the Calibration Procedure is completed.

It is to be noted that while the foregoing discussion assumes that two (2) Components of a present invention System are simultaneously rotated during practice of said Calibration Procedure, in general any number of present invention System Components could be simultaneously rotated. The scope of the present invention Calibration Procedure is thus, in general terms, sufficiently broad to include a Multi-Dimensional Fourier Series based approach. It has been found in practice, however, that it is generally not necessary to confront the added complexity associated with rotating more than two (2) present invention System Components, to arrive at sufficiently accurate present invention Matrix Representing System Component contained Compensating Calibration Parameter values.

FIG. *7a* exemplifies a Surface Contour Plot showing Arbitrary Intensity vs. two (2) IR Ellipsometer System Azimuthal Angles. FIG. *7b* exemplifies an Intensity vs. Wavelength plot which can be achieved by practice of the present invention Method. Both FIGS. *7a* and *7b* provide visual aides, but are not absolutely necessary to the evaluation of Calibration Parameters.

FIGS. *8a* and *8b* show PSI and DELTA Plots for a Polycarbonate Sample System achieved utilizing an IR Ellipsometer System Calibrated by the Method of the present invention. As well, FIGS. *9a* and *9b* show Real and Imaginary Parts of Optical Constants of said Polycarbonate Sample System. It should be noted that Dielectric Functions are constants of a Sample System, and that data were obtained at three (3) different Angles of Incidence (see the angle (θ) in FIG. *1c*). The Real and Imaginary Parts of a Dielectric Function of a material characterize the speed at which electromagnetic wavelength will pass therethrough, and how the energy present will be absorbed thereby. That the Real and Imaginary Parts of the Dielectric Function results at all three (3) Angles of Incidence are coincident, shows that the Calibration procedure has operated properly.

Figure 2A:
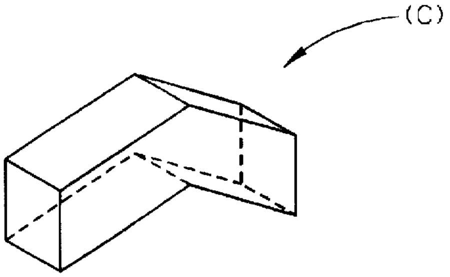
FIG. 2*a* is a three-dimensional perspective view of the dual-rhomb shaped compensator of the present invention.
Figure 2B:
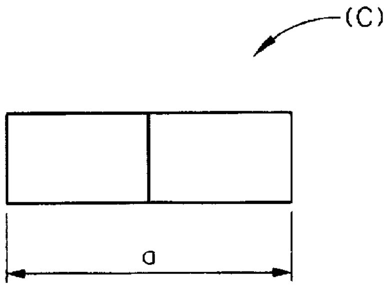
FIG. 2*b* is a top view of the dual-rhomb shaped compensator of the present invention.
Figure 2C:
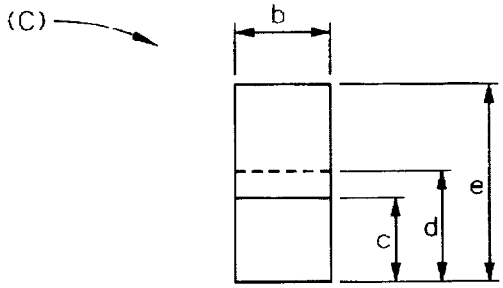
FIG. 2*c* is a side elevational view of the dual-rhomb shaped compensator of the present invention.

Turning now to FIGS. 2*a*, 2*b*, 2*c*, 2*d* and FIG. 3, there is shown a preferred embodiment of the present invention Compensator means (C) Component. Said Compensator means (C) is typically constructed of Zinc-Selenide or Zinc-Sulfide, and is essentially "Achromatic" in use, (that is, over a range of wavelengths from two (2) microns to fourteen (14) microns, a variation of only approximately seven (7%) percent occurs). Said present invention Compensator means (C) is of a Dual-Rhomb design, which can be described as that System Configuration which results from the abutting of the short sides of two similarly sized Three-Dimensional Parallelograms. FIG. 2*a* shows a Three-Dimensional perspective view of the preferred embodiment of the present invention Compensator means (C), while FIG. 2*b* shows a Top view, FIG. 2*c* a Side Elevational view and FIG. 2*d* a Front Elevational view. Present invention embodiment dimensions are indicated in FIGS. 2*a*–2*d* as ((a), (b), (c), (d), (e) & (f)). Preferred values thereof are:

(a)—1.7272;
(b)—0.5;
(c)—0.55;
(d)—0.6794;
(e)—1.2294;
(f)—0.8636;

with each dimension being in centimeters.

Figure 2D:
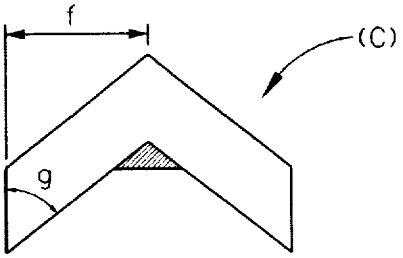
FIG. 2*d* is a front elevational view of the dual-rhomb shaped compensator of the present invention.

Also shown in FIG. 2*d* is a present invention preferred embodiment acute angle (g) between the long and short sides of said Parallelogram shaped Compensator means, as viewed in Front Elevation, said acute angle being:

(g)—51.806 degrees.

It is also noted that the index of refraction of the material form which the present invention Dual-Rhomb Compensator means is made (eg. Zinc Sulfide or Zinc Selenide) is typically between 2.38 and 2.45.

Figure 3:
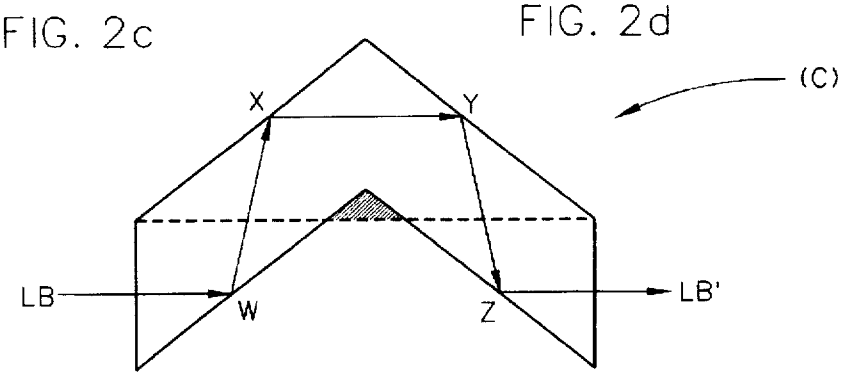
FIG. 3 is a front elevational view of the dual-rhomb shaped compensator of the present invention, with a polarized beam of electromagnetic wavelengths shown passing therethrough.

Turning now to FIG. 3, there is shown a Polarized Beam of Electromagnetic Wavelengths (LB) entering said Compensator means (C), and, after undergoing four (4) internal reflections, (at (W), (X), (Y) & (Z)), exiting said Compensator means as Polarized Beam of Electromagnetic Wavelengths (LB'). The most significant point demonstrated in FIG. 3 is that essentially no deviation in the Direction of Propagation of said Polarized Beam of Electromagnetic Wavelengths (LB)–(LB') is effected by said Compensator means (C). That is, the Direction of Propagation of both entering (LB) and exiting (LB') Polarized Beams is essentially the same. This is very important in the context of the present invention because the Compensator means is caused to rotate during the Method of the Calibration Procedure described infra. Were the Direction of Propagation of said Polarized Beam of Electromagnetic Wavelengths caused to deviate by passage through said Compensator (C), rotation thereof would introduce complexities into analysis which would be extremely difficult, if not impossible, to compensate out. It is noted that the inventor knows of no previous use of such a Non-Propagation Direction Deviation causing Rotatable Essentially Achromatic Compensator in the context of an Ellipsometer System utilizing an Infrared range of Wavelengths.

It is noted that the region of the Compensator means (C) shown in FIG. 2*d* and FIG. 3, which is identified with hash lines, is not critical to the operation of the Compensator means (C).

Figure 4:
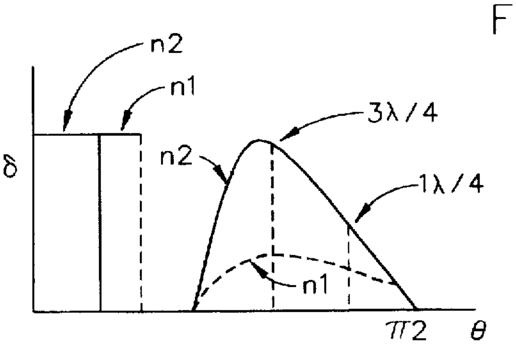
FIG. 4 shows a plot of the phase shift provided between quadrature components in a polarized electromagnetic beam by an internal reflection in a rhomb-type compensator, as a function of the angle of incidence said polarized electromagnetic beam makes to the internal surface of said rhomb-type compensator at the point of said internal reflection.
Figure 5A:
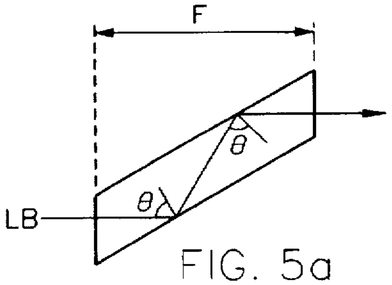
FIGS. 5*a* and 5*b* show, respectively, the relative overall lengths of Rhomb-type compensator sections which, when combined into dual rhomb systems, serve to provide (3*λ/4) and (LAMBDA/4) phase shifts between quadrature components of a polarized electromagnetic beam passed therethrough in use.
Figure 5B:
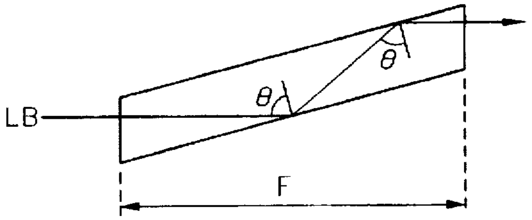
Figure 6A:
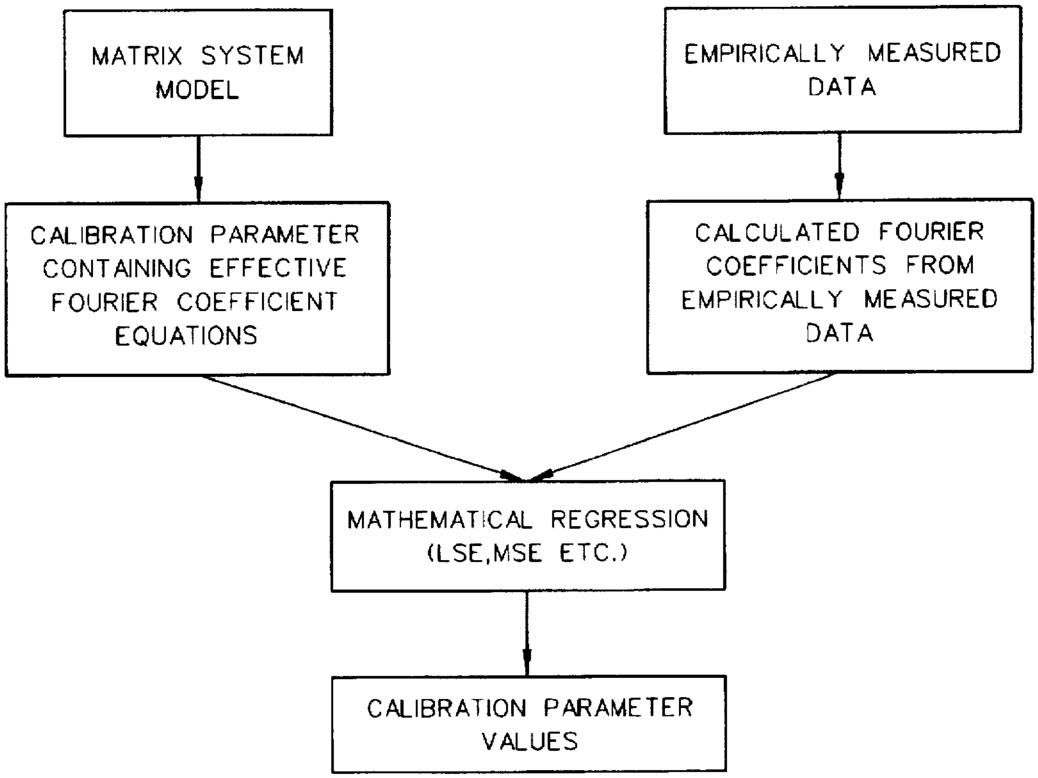
FIGS. 6*a* & 6*b* show a flow charts for the calibration procedure of the present invention.
Figure 6B:
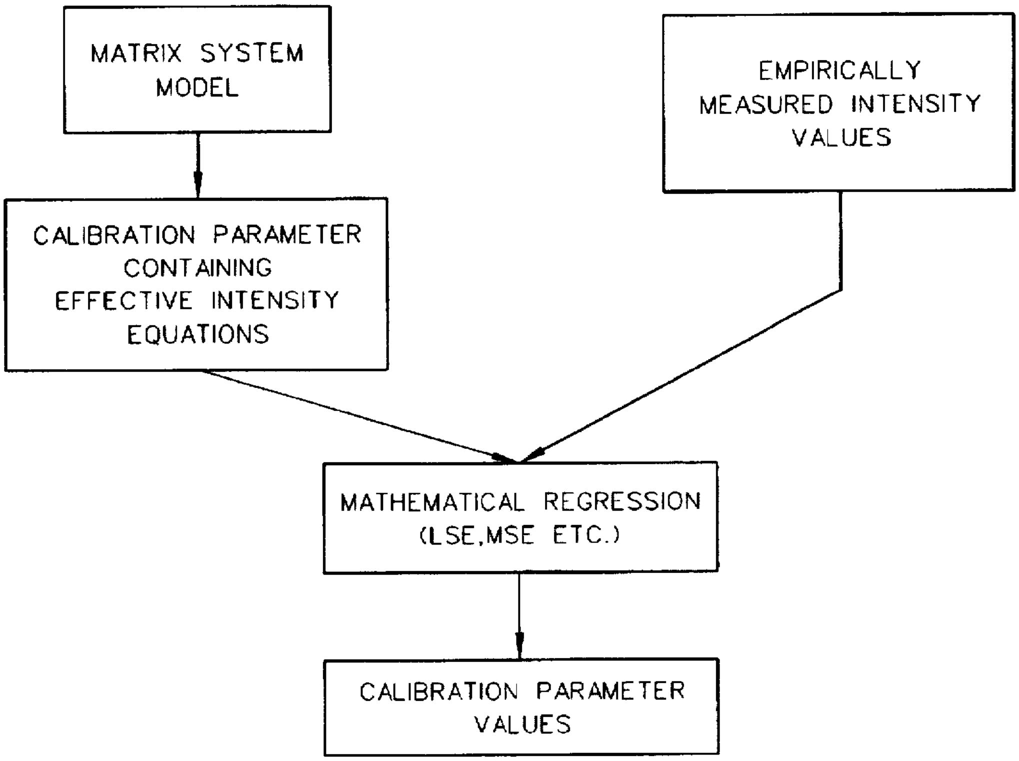
Figure 7A:
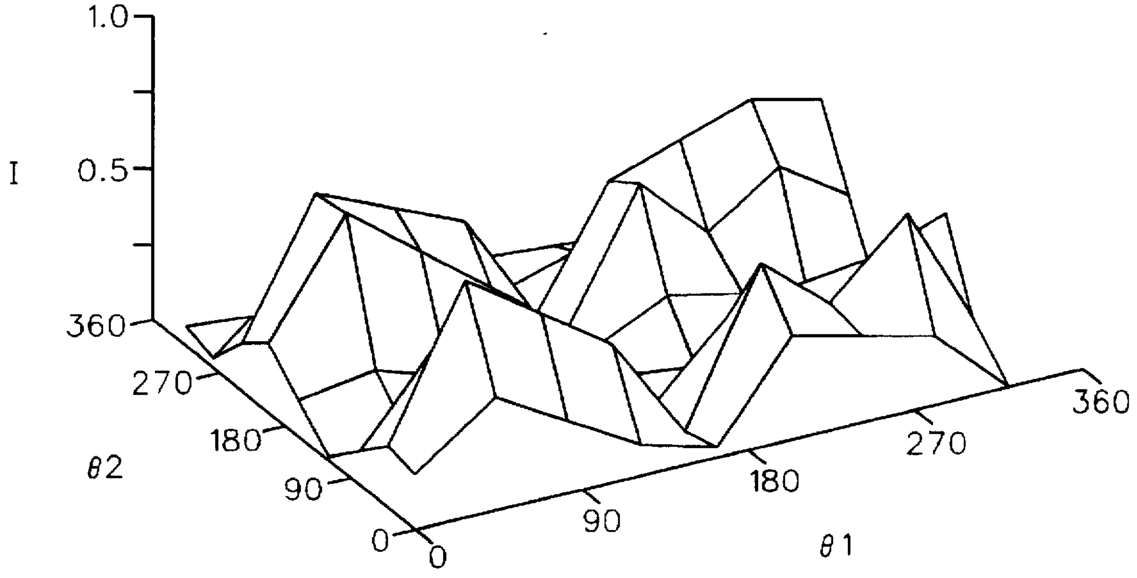
FIGS. 7*a* and 7*b* show three-dimensional and two-dimensional Plots relevant to practice of the present invention.
Figure 7B:
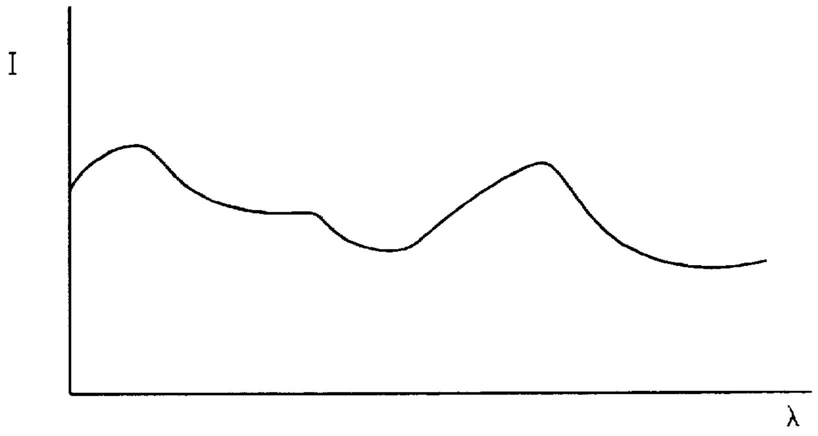
Figure 8A:
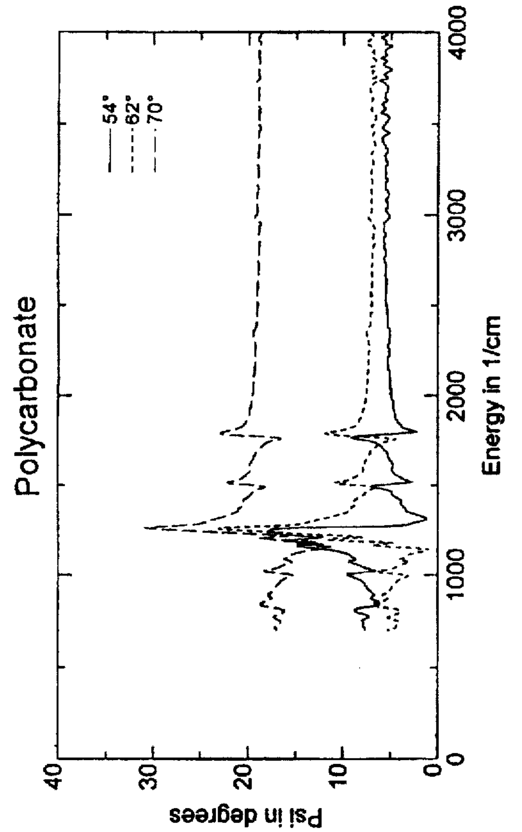
FIGS. 8*a* and 8*b* show actual PSI and DELTA plots for a Polycarbonate Sample System which were achieved by use of a calibrated present invention IR ellipsometer system.
Figure 8B:
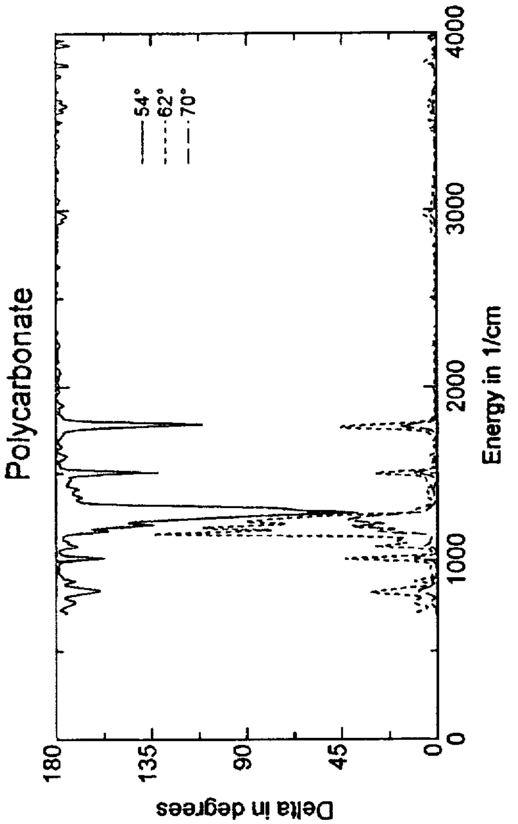
Figure 9A:
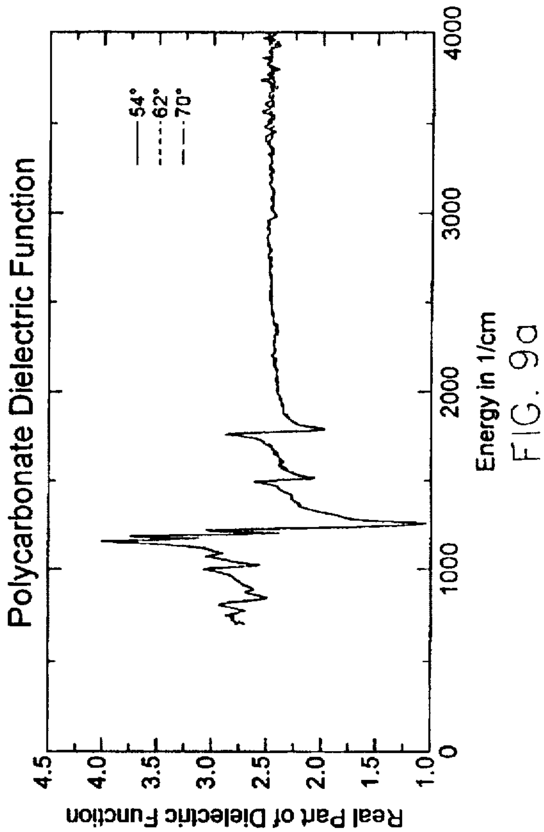
FIGS. 9*a* and 9*b* real and imaginary parts of the dielectric function for a polycarbonate sample system which were achieved by use of a present invention calibration method, calibrated, present invention IR ellipsometer system.
Figure 9B:
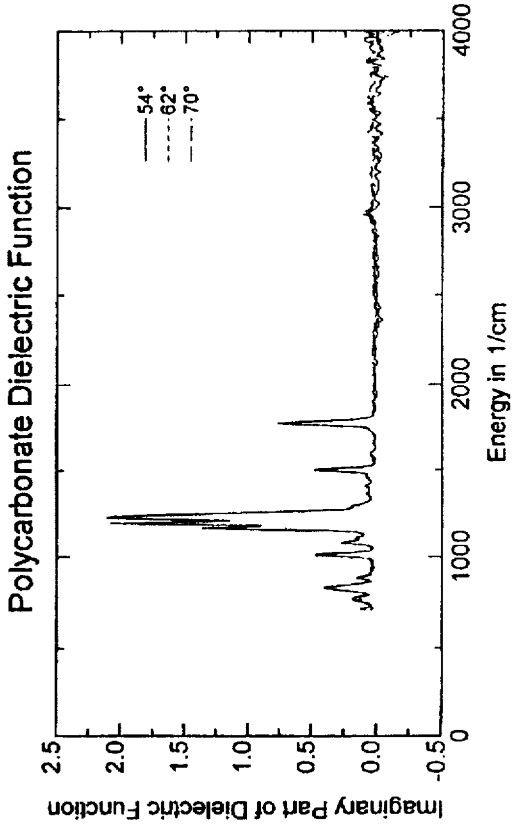

It is further disclosed that the effect of the four (4) internal reflections at ((W), (X), (Y) & (Z)), is to introduce a phase shift between quadrature components in Polarized Beam of Electromagnetic Wavelengths (LB') exiting said Compensator means of $(3*\lambda/4)$, as compared to the phase angle between quadrature components of entering Polarized Beam of Electromagnetic Wavelengths (LB), (where $\lambda$ is the Wavelength present). It is to be understood that this is provides a relative $(\lambda/4)$ phase shift between quadrature components of a Polarized Beam of Electromagnetic Wavelengths (LB) passed therethrough because the magnitude of $((3*\lambda/4)$–LAMBDA) is equal to the magnitude of $(\lambda/4)$, and that it is said relative phase shift which is of interest. The reason the approach to providing the relative phase shift between quadrature components of a Polarized Beam of Electromagnetic Wavelengths (LB) described is utilized is because the overall length (e.g. "f" in FIG. 2*d*), of a Rhomb Section can be significantly shorter as compared to the length thereof if a direct $(\lambda/4)$ phase shift is imposed. Why this is the case can be understood by reference to FIGS. 4, 5*a* & 5*b*. FIG. 4 shows the amount of phase shift provided between quadrature components of a Polarized Electromagnetic Beam by an internal reflection, (such as at W, X, Y and Z in FIG. 3), as a function of the Angle Of Incidence ($\theta$) said Polarized Electromagnetic Beam. Identified are the Angles Of Incidence ($\Theta$) necessary to effect overall $(3*\lambda/4)$ and $(\lambda/4)$ phase shifts, for two Indicies of Refraction (n1 and n2, where (n1 is greater than n2). (Note, each reflection individually provides $(3*\lambda/16)$ and (LAMBDA/16) phase shift). The Angle Of Incidence ($\Theta$) is seen to be greater where the overall $(\lambda/4)$ result is achieved as compared to that where the $(3*\lambda/4)$ result is achieved. Reference to FIGS. 5*a* and 5*b* show that a smaller Angle Of Incidence ($\Theta$) as is effected in the FIG. 5*a* case, allows a shorter Rhomb Length "F" than is present in the FIG. 5*b* case, wherein a larger Angle Of Incidence ($\Theta$) is effected. A smaller overall size Compensator means (C) is desirable as use in systems wherein space is tight is made possible.

It is to be understood that any Compensator which performs a similar function is to be considered equivalent. For instance, a Dual-Rhomb shape can be effected by properly combining four (4) Triangular Prisms, (wherein each Rhomb shape is effected by proper combination of two of said Triangular Shaped Prisms). Any Compensator which effects four (4) internal reflections each of which reflections effect a $(3*\lambda/16)$ or (LAMBDA/16) phase shift, and which does not cause deviation in the Direction of Propagation of said Polarized Beam of Electromagnetic Wavelengths passed through said Compensator, is to be considered withing the scope of the present invention for the purposes of claim interpretation.

It is to be kept in mind when reading the claims that an Element of a Matrix as described above, is identically a Coefficient of a term in a Mathematical, (eg. Fourier), Series.

It is also to be kept in mind that a while the preferred embodiment provides that Calibration Parameter evaluation is achieved by a regression of analogically equivalent Calibration Parameter containing Analytically derived equations for Multiple Fourier Series Coefficients, it is possible to skip the intermediate step of determining Coefficients of a Multiple Fourier Series. That is, while working with Multiple Fourier Series Coefficients provides utility in the form of enhanced calculation speed, it is also possible to regress analogically corresponding Analytically Derived Calibration Parameter containing Equations for Intensity Values, directly onto Empirically Determined Intensity values. Both approaches are within the scope of the present invention.

It is also to be understood that the term "Intensity", as measured by a Detector System, is generally understood to represent a value which results from squaring an Electric Field. In the claims, the term "Intensity" is to be interpreted sufficiently broad to include such essentially equivalent values which could be alternatively be measured by a Detector System.

It is also noted that while a Reflecting Sample System was demonstrated in the foregoing, it is possible to practice Ellipsometry utilizing a Transmission through a Sample System as the Source Polarization State Change Data. Claim language will utilize the terminology "Interaction With" when referring to Polarized Beam of Electromagnetic Wavelengths which are caused to be incident upon a Sample System, whether Data is obtained from a Reflected or Transmitted Polarized Beam.

As well, it is to be understood that an "Alternative Sample System" can be formed by combination with a "Lumped" Sample System, (which "Lumping" occurs between, for instance, an added Compensator and a present Sample System, rather than by replacement of a Sample System per se.

It is also to be understood that while a Multiple Fourier Series was used as an example of a Coefficient providing Series in the foregoing, other Coefficient providing Mathematical Series could be substituted therefore in practice of the present invention. That is, the Method of the present invention can utilize any suitable Coefficient containing Mathematical Series and is not limited to use of a Multiple Fourier Series to provide Calibration Parameter containing Coefficient Equations, which Calibration Parameters are evaluated by a Regression Procedure of said Calibration Parameter containing Equations onto empirically derived analogically equivalent numerical values. (Note, the word empirical is to be understood as indicating that experimental techniques are involved).

It is further noted that, while work by the Inventor has been focused on application of the present invention Calibration Procedure to Rotating Component Sample System Investigating Systems, the present invention Calibration Procedure can be applied to Sample System Investigating Systems which are comprised of Components which are "set" by Rotation, Tilting and/or application of Electric or Magnetic Fields. Such Sample System Investigating Systems include Rotating Component, and Phase Modulation Component containing Ellipsometers and Polarimeters. The claims, where applicable, should be interpreted to include said possibilities.

It is also to be understood that a Polarizer means can be a Light Source per se, without external polarization means present, and that a "Polarized" beam of electromagnetic wavelengths need not be near one-hundred (100%) percent polarized.

Finally, it is emphasized that no known Calibration procedure for application to Ellipsometer or Polarimeter and the like Systems, allows for evaluation of Calibration Parameters in Elements of Matrix Representations of System Components which are "Rotated", as well as System Components which are "Non-Rotated", during the Calibration Procedure. As well, no known such Calibration Procedure utilizes data obtained with Sample System Analysis Systems oriented in both Straight-Through and "Sample Present" configurations. In that alone, the present invention provides novelty. As well, no known regression based approach to Ellipsometer or Polarimeter and the like Systems allows simultaneous evaluation of Calibration Parameters for all present System Components, emphasis added.

Having hereby disclosed the subject matter of this invention, it should be obvious than many modifications, substitutions, and variations of the present invention are possible in light thereof. It is therefore to be understood that the present invention may be practiced other than as specifically described, and should be limited in breadth and scope only by the claims.

We claim:

1. A sample system investigating system, which sample system investigating system is sequentially comprised of a source of a beam of electromagnetic wavelengths, a polarizer means, a stage for supporting a sample system, an analyzer means and a detector system, which sample system investigating system is further comprised of at least a first compensator means, said at least first compensator means being positioned in said sample system investigating system at a location selected from the group consisting of, before and after, said stage for supporting a sample system, and which sample system investigating system optionally comprises a second compensator means positioned in said sample system investigating system at a location complementary to said first compensator means, said position being selected from the group consisting of, respectively, after and before, said stage for supporting said sample system; said at least first compensator means in said sample system investigation system being essentially achromatic and of a dual-rhomb construction, such that a polarized beam of electromagnetic wavelengths caused to pass therethrough in use experiences four internal reflections, each of which internal reflections causes a retardance between quadrature components of said polarized beam of electromagnetic wavelengths, selected from the group consisting of one-sixteenth and of three-sixteenths of a wavelength, which at least first compensator means effects essentially no deviation or displacement in the direction of propagation of said beam of electromagnetic wavelenghts caused to pass therethrough, even when said at least first compensator means is caused to rotate.

2. A sample system investigating system as in claim 1, in which said at least first compensator means is made of a material with an index of refraction of 1.8 and above, selected from the group consisting of zinc-selenide, zinc-sulfide, silver-chloride, diamond, cadnium-sulfide, titanium-oxide, amorphous selenium, silicon, germanium, tellurium and indium-antimony, arsenic-selenide, irtran-2, irtran-4, irtran-6 and KRS-6, such that said sample system investigating system is configured for use in the infrared range of the electromagnetic spectrum.

3. A sample system investigating system as in claim 1, in which said at least first compensator means is accurately described as being two three-dimensional parallelograms, each comprised of long and short sides, in which at least first compensator means a short side of each three-dimensional parallelogram are in abutted connection with one another; wherein the acute angle between long and short sides of each three-dimensional parallelogram is 51.806 degrees; and wherein the overall length dimension, as viewed in frontal elevation is 1.7272 centimeters; and wherein the overall height dimension, as viewed in side elevation is 1.2294 centimeters; and wherein the overall width as viewed in side elevation is 0.5 centimeters; and which wherein the index of refraction is between 2.38 and 2.45.

4. A method of calibrating for nonidealities in mathematical representations of rotated and non-rotated components of a sample system investigating system, which sample system investigating system is sequentially comprised of a source of a beam of electromagnetic wavelengths, a polarizer means, a stage for supporting a sample system, an analyzer means and a detector system, which sample system investigating system is further comprised of at least a first compensator means, said at least a first compensator means being positioned in said sample system investigating system at a location selected from the group consisting of, before and after, said stage for supporting a sample system, and which sample system investigating system optionally comprises a second compensator means positioned in said sample system investigating system at a location complementary to said first compensator means, said position being selected from the group consisting of, respectively, after and before, said stage for supporting said sample system;

said method comprising the steps of:

a. empirically obtaining at least two data sets, each of which data sets consists of intensity values measured by said detector system, said intensity values being a function wavelength and of settings of at least two of said sample system investigating system components, which sample system investigating system components are selected from the group consisting of said polarizer means, said analyzer means and present compensator means; at least one of which data sets is obtained with said sample system investigating system oriented in a "sample-present" configuration and another of which data sets is obtained with said sample system investigating system oriented in a configuration selected from the group consisting of a "alternative sample-present" and a "straight-through" configuration; which "straight-through" configuration results from orienting said sample system investigating system such that a beam of electromagnetic wavelengths provided by said source of a beam of electromagnetic wavelengths is caused to pass through said polarization means, through said analyzer means and into said detector system; and which "sample-present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that in either of said "straight-through" or "sample-present" configurations of said sample system investigating system, said beam of electromagnetic wavelengths is also caused to pass through present compensator means;

b. applying mathematical formula to said data sets to provide empirically derived numerical values for coefficients of multi-dimensional mathematical series, said dimension of said multi-dimensional mathematical series being determined by the number of sample system investigating system components which were caused to assume various settings during the obtaining of data sets in step a., said sample system investigating system components being selected from the group consisting of said polarizer means, said analyzer means and present compensator means;

c. effectively deriving analytical non-ideality compensating calibration parameter containing equations for multi-dimensional mathematical series coefficients, each of which analytically derived non-ideality compensating calibration parameter containing equations for multi-dimensional mathematical series coefficients is analogically equivalent to numerical values for corresponding multi-dimensional mathematical series coefficients empirically determined by applying mathematical formula to the data sets as in Step b., said effective analogically equivalent non-ideality compensating calibration parameter containing equations for multi-dimensional mathematical series coefficients being achievable by performing matrix multiplication of non-ideality compensating calibration parameter containing matrices which represent sample system investigating system components and rotation matrices, each thereof being oriented in a series of said sample system investigating system component and rotation matrices to appropriately represent a "straight-through" or a "sample-present" configuration of said sample system investigating system;

d. performing a simultaneous mathematical regression of Step c., effective analytically arrived at non-ideality compensating calibration parameter containing equations for coefficients of multi-dimensional mathematical series, onto analogically equivalent numerical values for multi-dimensional mathematical series coefficients as arrived at in Step b.;

such that non-ideality compensating calibration parameters in said effective non-ideality compensating calibration parameter containing equations for multi-dimensional mathematical series coefficients are simultaneously evaluated, based upon an error reducing criteria.

5. A method of calibrating for nonidealities as in claim 4, which further comprises, in conjunction with Step a., the obtaining of at least one additional data set of intensity values measured by said detector system, which intensity values are a function of wavelength and of the settings of at least two of said sample system investigating system components in said sample system investigating system, which at least one additional data set is/are however, obtained from a sample system investigation system configuration selected from the group consisting of (wherein at least one of the sample system investigating system components originally present, is removed, and wherein an alternative sample system replaces an originally present sample system); the obtaining of said at least one additional data set being followed by application of mathematical formula to said at least one additional data set to provide empirically derived numerical values for coefficients of multi-dimensional mathematical series, said dimension of said multi-dimensional mathematical series being determined by the number of sample system investigating system components which are caused to assume various settings during the obtaining of said at least one additional data set; said method further comprising the derivation of effective analytical non-ideality compensating calibration parameter containing equations for coefficients of multi-dimensional mathematical series coefficients, which effective analytically derived non-ideality compensating calibration parameter containing equations for multi-dimensional mathematical series coefficients are analogically equivalent to numerical values for the multi-dimensional mathematical series coefficients empirically determined by the application of mathematical formula to said at least one additional data set; and including said additional empirically determined numerical values and analogically equivalent effective analytically derived non-ideality compensating calibration parameter containing equations for multi-dimensional mathematical series coefficients in said simultaneous mathematical regression in Step d.

6. A method of calibrating for nonidealities as in claim 5, wherein the step of performing a simultaneous mathematical regression such that each non-ideality compensating calibration parameter in each effective non-ideality compensating calibration parameter containing equation for coefficients of said multi-dimensional mathematical series, involves a multi-dimensional Fourier series.

7. A method of calibrating for nonidealities as in claim 4, in which the procedure for achieving the setting of said at least one of said sample system investigating system components in said sample system investigating system is selected from the group consisting of: rotation of, tilting of, sliding of, application of an electrical field, and application of a magnetic field to a sample system investigating system component.

8. A method of calibrating for nonidealities as in claim 4, wherein the step of performing a simultaneous mathematical regression such that each non-ideality compensating calibration parameter in each effective non-ideality compensating calibration parameter containing equation for coefficients of said multi-dimensional mathematical series, involves a multi-dimensional Fourier series.

9. A method of calibrating for nonidealities in mathematical representations of rotated and non-rotated components in a sample system investigating system, which sample system investigating system is sequentially comprised of a source of a beam of electromagnetic wavelengths, a polarizer means, a stage for supporting a sample system, an analyzer means and a detector system, which sample system investigating system is further comprised of at least a first compensator means, said at least a first compensator means being positioned in said sample system investigating system at a location selected from the group consisting of, before and after, said stage for supporting a sample system, and which sample system investigating system optionally comprises a second compensator means positioned in said sample system investigating system at a location complementary to said first compensator means, said position being selected from the group consisting of, respectively, after and before, said stage for supporting said sample system; said at least first compensator means in said sample system investigation system being essentially achromatic and of a dual-rhomb construction such that a polarized beam of electromagnetic wavelengths caused to pass therethrough in use, experiences four internal reflections, each of which internal reflections causes a retardance between quadrature components of said polarized beam of electromagnetic wavelengths, selected from the group consisting of one-sixteenth and of three-sixteenths of a wavelength, but which at least first compensator means effects essentially no deviation in the direction of propagation of said beam of electromagnetic wavelengths caused to pass therethrough, even when said at least one compensator means is caused to rotate;

said method comprising the steps of:

a. empirically obtaining at least two data sets, each of which data sets consists of intensity values measured by said detector system, said intensity values being a function wavelength and of settings of at least two of said sample system investigating system components, which sample system investigating system components are selected from the group consisting of said polarizer means, said analyzer means and present compensator means; at least one of which data sets is obtained with said sample system investigating system oriented in a "sample-present" configuration and another of which data sets is obtained with said sample system investigating system oriented in a configuration selected from the group consisting of "alternative sample-present" and a "straight-through" configuration; which "straight-through" configuration results from orienting said sample system investigating system such that a beam of electromagnetic wavelengths provided by said source of a beam of electromagnetic wavelengths is caused to pass through said polarization means, through said analyzer means and into said detector system; and which "sample-present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that in either of said "straight-through" or "sample-present" configurations of said sample system investigating system, said beam of electromagnetic wavelengths is also caused to pass through present compensator means;

b. applying mathematical formula to said data sets to provide empirically derived numerical values for coefficients of multi-dimensional mathematical series, said dimension of said multi-dimensional mathematical series being determined by the number of sample system investigating system components which were caused to assume various azimuthal angle settings during the obtaining of data sets in step a., said sample system investigating system components, the azimuthal angles of which were variously set during acquisition of said data sets, being selected from the group consisting of said polarizer means, said analyzer means and present compensator means;

c. effectively deriving analytical non-ideality compensating calibration parameter containing equations for multi-dimensional mathematical series coefficients, each of which effective analytically derived non-ideality compensating calibration parameter containing equations for multi-dimensional mathematical series coefficients is analogically equivalent to numerical values for corresponding multi-dimensional mathematical series coefficients empirically determined by applying mathematical formula to the data sets as in Step b., said analogically equivalent non-ideality compensating calibration parameter containing equations for multi-dimensional mathematical series coefficients being achievable by performing matrix multiplication of non-ideality compensating calibration parameter containing matrices which represent sample system investigating system components and rotation matrices, each thereof being oriented in a series of said sample system investigating system component and rotation matrices to appropriately represent a "straight-through" or a "sample-present" configuration of said sample system investigating system;

d. performing a simultaneous mathematical regression of Step c., analytically arrived at effective non-ideality compensating calibration parameter containing equations for coefficients of multi-dimensional mathematical series, onto analogically equivalent numerical value for multi-dimensional mathematical series coefficients as arrived at in Step b.;

such that non-ideality compensating calibration parameters in said effective non-ideality compensating calibration parameter containing equations for a multi-dimensional mathematical series coefficients are simultaneously evaluated, based upon an error reducing criteria.

10. A method of calibrating for nonidealities as in claim 9, which further comprises, in conjunction with Step a., the obtaining of at least one additional data set of intensity values measured by said detector system, which intensity values are a function of wavelength and of the settings of at least two of said sample system investigating system components in said sample system investigating system, which at least one additional data set is/are however, obtained from a sample system investigation system configuration selected from the group consisting of (wherein at least one of the sample system investigating system components originally present, is removed, and wherein an alternative sample system replaces the originally present sample system); the obtaining of said at least one additional data set being followed by application of mathematical formula to said at least one additional data set to provide empirically derived numerical values for coefficients of multi-dimensional mathematical series, said dimension of said multi-dimensional mathematical series being determined by the number of sample system investigating system components which are caused to assume various settings during the obtaining of said at least one additional data set; said method further comprising the derivation of effective analytical non-ideality compensating calibration parameter containing equations for coefficients of multi-dimensional mathematical series coefficients, which effective analytically derived non-ideality compensating calibration parameter containing equations for multi-dimensional mathematical series coefficients are analogically equivalent to numerical values for the multi-dimensional mathematical series coefficients empirically determined by the application of mathematical formula to said at least one additional data set; and including said additional empirically determined numerical values and analogically equivalent effective analytically derived non-ideality compensating calibration parameter containing equations for multi-dimensional mathematical series coefficients in said simultaneous mathematical regression in Step d.

11. A method of calibrating for nonidealities as in claim 10, wherein the step of performing a simultaneous mathematical regression such that each non-ideality compensating calibration parameter in each effective non-ideality compensating calibration parameter containing equation for coefficients of said multi-dimensional mathematical series, involves a multi-dimensional Fourier series.

12. A method of calibrating for nonidealities as in claim 9, wherein the step of performing a simultaneous mathematical regression such that each non-ideality compensating calibration parameter in each effective non-ideality compensating calibration parameter containing equation for coefficients of said multi-dimensional mathematical series, involves a multi-dimensional Fourier series.

13. A method of calibrating for nonidealities in mathematical representations of rotated and nonrotated components of a sample system investigating system, which sample system investigating system is sequentially comprised of a source of a beam of electromagnetic wavelengths, a polarizer means, a stage for supporting a sample system, an analyzer means and a detector system, which sample system investigating system is further comprised of at least a first compensator means, said at least a first compensator means being positioned in said sample system investigating system at a location selected from the group consisting of, before and after, said stage for supporting a sample system, and which sample system investigating system optionally comprises a second compensator means positioned in said sample system investigating system at a location complementary to said first compensator means, said position being selected from the group consisting of, respectively, after and before, said stage for supporting said sample system; said method comprising the steps of:

a. empirically obtaining at least two data sets, each of which data sets consists of intensity values measured by said detector system, said intensity values being a function of wavelength and of rotated settings of azimuthal angles of said analyzer means and said polarizer means of said sample system investigating system; one of which data sets is obtained with said sample system investigating system oriented in a "sample-present" configuration such that in one case a compensator means is present and in the other case a present compensator means is not present; which "sample-present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that said beam of electromagnetic wavelengths is also caused to pass through any present compensator means;
b. applying mathematical formula to said data sets to provide empirically derived numerical values for coefficients of two-dimensional mathematical series, said dimension of said two-dimensional mathematical series being determined by the number of sample system investigating system components, namely the analyzer means and the polarizer means, which were caused to assume various azimuthal angle settings during the obtaining of data sets in step a.;
c. effectively deriving analytical non-ideality compensating calibration parameter containing equations for two-dimensional mathematical series coefficients, each of which effective analytically derived non-ideality compensating calibration parameter containing equations for two-dimensional mathematical series coefficients is analogically equivalent to numerical values for corresponding two-dimensional mathematical series coefficients empirically determined by applying mathematical formula to the data sets as in Step b., said analogically equivalent non-ideality compensating calibration parameter containing equations for two-dimensional mathematical series coefficients being achievable by performing matrix multiplication of non-ideality compensating calibration parameter containing matrices which represent sample system investigating system components and rotation matrices, each thereof being oriented in a series of said sample system investigating system component and rotation matrices to appropriately represent a "straight-through" or a "sample-present" configuration of said sample system investigating system;
d. performing a simultaneous mathematical regression of Step c., analytically arrived at effective non-ideality compensating calibration parameter containing equations for coefficients of two-dimensional mathematical series, onto analogically equivalent numerical value for two-dimensional mathematical series coefficients as arrived at in Step b.;

such that non-ideality compensating calibration parameters in said effective non-ideality compensating calibration parameter containing equations for two-dimensional mathematical series coefficients are simultaneously evaluated, based upon an error reducing criteria.

14. A method of calibrating for nonidealities as in claim 13, wherein the step of performing a simultaneous mathematical regression such that each non-ideality compensating calibration parameter in each effective non-ideality compensating calibration parameter containing equation for coefficients of said two-dimensional mathematical series, involves a two-dimensional Fourier series.

15. A method of calibrating for nonidealities in mathematical representations of rotated and non-rotated components of a sample system investigating system, which sample system investigating system is sequentially comprised of a source of a beam of electromagnetic wavelengths, a polarizer means, a stage for supporting a sample system, an analyzer means and a detector system, which sample system investigating system is further comprised of at least a first compensator means, said at least a first compensator means being positioned in said sample system investigating system at a location selected from the group consisting of, before and after, said stage for supporting a sample system, and which sample system investigating system optionally comprises a second compensator means positioned in said sample system investigating system at a location complementary to said first compensator means, said position being selected from the group consisting of, respectively, after and before, said stage for supporting said sample system; said method comprising the steps of:

a. empirically obtaining at least three data sets, each of which data sets consists of intensity values measured by said detector system, said intensity values being a function of wavelength and of rotated settings of azimuthal angles of said analyzer means and said polarizer means of said sample system investigating system; one of which data sets is obtained with said sample system investigating system oriented in a configuration selected from the group consisting of a "sample-present" and a "straight-through" configuration; a second of which data sets is obtained with said sample system investigating system oriented in an "alternative sample-present" configuration; and a third of which data sets is obtained with said sample system investigating system oriented in a configuration selected from the group consisting of, (wherein a present compensator means is removed, and wherein an "alternative sample-system" is substituted for a previously present sample-system); which "straight-through" configuration results from orienting said sample system investigating system such that a beam of electromagnetic wavelengths provided by said source of a beam of electromagnetic wavelengths is caused to pass through said polarization means, through said analyzer means and into said detector system; and which "sample-present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that in either of said "straight-through" or "sample-present" configurations of said sample system investigating system, said beam of electromagnetic wavelengths is also caused to pass through any present compensator means;

b. applying mathematical formula to said data sets to provide empirically derived numerical values for coefficients of two-dimensional mathematical series, said dimension of said two-dimensional mathematical series being determined by the number of sample system investigating system components, namely the analyzer means and the polarizer means, which were Caused to assume various azimuthal angle settings during the obtaining of data sets in step a.;

c. effectively deriving analytical non-ideality compensating calibration parameter containing equations for two-dimensional mathematical series coefficients, each of which effective analytically derived non-ideality compensating calibration parameter containing equations for two-dimensional mathematical series coefficients is analogically equivalent to numerical values for corresponding two-dimensional mathematical series coefficients empirically determined by applying mathematical formula to the data sets as in Step b., said analogically equivalent non-ideality compensating calibration parameter containing equations for two-dimensional mathematical series coefficients being achievable by performing matrix multiplication of non-ideality compensating calibration parameter containing matrices which represent sample system investigating system components and rotation matrices, each thereof being oriented in a series of said sample system investigating system component and rotation matrices to appropriately represent a "straight-through" or a "sample-present" configuration of said sample system investigating system;

d. performing a simultaneous mathematical regression of Step c., analytically arrived at effective non-ideality compensating calibration parameter containing equations for coefficients of two-dimensional mathematical series, onto analogically equivalent numerical value for two-dimensional mathematical series coefficients as arrived at in Step b.;

such that non-ideality compensating calibration parameters in said effective non-ideality compensating calibration parameter containing equations for two-dimensional mathematical series coefficients are simultaneously evaluated, based upon an error reducing criteria.

16. A method of calibrating for nonidealities as in claim 15, wherein the step of performing a simultaneous mathematical regression such that each non-ideality compensating calibration parameter in each effective non-ideality compensating calibration parameter containing equation for coefficients of said two-dimensional mathematical series, involves a two-dimensional Fourier series.

17. A method of calibrating for nonidealities in mathematical representations of rotated and non-rotated components of a sample system investigating system, which sample system investigating system is sequentially comprised of a source of a beam of electromagnetic wavelengths, a polarizer means, a stage for supporting a sample system, an analyzer means and a detector system, which sample system investigating system is further comprised of at least a first compensator means, said at least a first compensator means being positioned in said sample system investigating system at a location selected from the group consisting of, before and after, said stage for supporting a sample system, and which sample system investigating system optionally comprises a second compensator means positioned in said sample system investigating system at a location complementary to said first compensator means, said position being selected from the group consisting of, respectively, after and before, said stage for supporting said sample system; said method comprising the steps of:

a. empirically obtaining at least two data sets, each of which data sets consists of intensity values measured by said detector system, said intensity values being a function of wavelength and of rotated settings of azimuthal angles of a component selected from the group consisting of (said polarizer means and said analyzer means), and one said compensator means of said sample system investigating system; one of which data sets is obtained with said sample system investigating system oriented in a "sample-present" configuration, and one of which data is obtained with said sample system investigating system oriented in a configuration selected from the group consisting of "alternative sample-present" and "straight-through"; which "straight-through" configuration results from orienting said sample system investigating system such that a beam of electromagnetic wavelengths provided by said source of a beam of electromagnetic wavelengths is caused to pass through said polarization means, through said analyzer means and into said detector system; and which "sample-present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that in either of said "straight-through" or "sample-present" configurations of said sample system investigating system, said beam of electromagnetic wavelengths is also caused to pass through present compensator means;

b. applying mathematical formula to said data sets to provide empirically derived numerical values for coefficients of two-dimensional mathematical series, said dimension of said two-dimensional mathematical series being determined by the number of sample system investigating system components, namely the polarizer means and compensator means, which were caused to assume various azimuthal angle settings during the obtaining of data sets in step a.;

c. effectively deriving analytical non-ideality compensating calibration parameter containing equations for two-dimensional mathematical series coefficients, each of which effective analytically derived non-ideality compensation calibration parameter containing equations for two-dimensional mathematical series coefficients is analogically equivalent to numerical values for corresponding two-dimensional mathematical series coefficients empirically determined by applying mathematical formula to the data sets as in Step b., said analogically equivalent non-ideality compensating calibration parameter containing equations for two-dimensional mathematical series coefficients being achievable by performing matrix multiplication of non-ideality compensating calibration parameter containing matrices which represent sample system investigating system components and rotation matrices, each thereof being oriented in a series of said sample system investigating system component and rotation matrices to appropriately represent a "straight-through" or a "sample-present" configuration of said sample system investigating system;

d. performing a simultaneous mathematical regression of Step c., analytically arrived at effective non-ideality compensating calibration parameter containing equations for coefficients of two-dimensional mathematical series, onto analogically equivalent numerical value for two-dimensional mathematical series coefficients as arrived at in Step b.;

such that non-ideality compensating calibration parameters in said effective non-ideality compensating calibration parameter containing equations for two-dimensional mathematical series coefficients are simultaneously evaluated, based upon an error reducing criteria.

18. A method of calibrating for nonidealities as in claim 17, wherein the step of performing a simultaneous mathematical regression such that each non-ideality compensating calibration parameter in each effective non-ideality compensating calibration parameter containing equation for coefficients of said two-dimensional mathematical series, involves a two-dimensional Fourier series.

19. A method of calibrating for nonidealities in mathematical representations of rotated and non-rotated components of a sample system investigating system, which sample system investigating system is sequentially comprised of a source of a beam of electromagnetic wavelengths, a polarizer means, a stage for supporting a sample system, an analyzer means and a detector system, which sample system investigating system is further comprised of a first compensator means, said first compensator means being positioned in said sample system investigating system at a location selected from the group consisting of, before and after, said stage for supporting a sample system, and which sample system investigating system further comprises a second compensator means positioned in said sample system investigating system at a location complementary to said first compensator means, said position being selected from the group consisting of, respectively, after and before, said stage for supporting said sample system; said method comprising the steps of:

a. empirically obtaining at least two data sets, each of which data sets consists of intensity values measured by said detector system, said intensity values being a function of wavelength and of rotated settings of azimuthal angles of said first compensator means and said second compensator means of said sample system investigating system; one of which data sets is obtained with said sample system investigating system oriented in a "sample-present" configuration, and one of which data is obtained with said sample system investigating system oriented in a configuration selected from the group consisting of "alternative sample-present" and "straight-through"; which "straight-through" configuration results from orienting said sample system investigating system such that a beam of electromagnetic wavelengths provided by said source of a beam of electromagnetic wavelengths is caused to pass through said polarization means, through said analyzer means and into said detector system; and which "sample-present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that in either of said "straight-through" or "sample-present" configurations of said sample system investigating system, said beam of electromagnetic wavelengths is also caused to pass through present first and second compensator means;

b. applying mathematical formula to said data sets to provide empirically derived numerical values for coefficients of two-dimensional mathematical series, said dimension of said two-dimensional mathematical series being determined by the number of sample system investigating system components, namely the first compensator means and the second compensator means, which were caused to assume various rotated azimuthal angle settings during the obtaining of data sets in step a.;

c. effectively deriving analytical non-ideality compensating calibration parameter containing equations for two-dimensional mathematical series coefficients, each of which effective analytically derived non-ideality compensating calibration parameter containing equations for two-dimensional mathematical series coefficients is analogically equivalent to numerical values for corresponding two-dimensional mathematical series coefficients empirically determined by applying mathematical formula to the data sets as in Step b., said analogically equivalent non-ideality compensating calibration parameter containing equations for two-dimensional mathematical series coefficients being achievable by performing matrix multiplication of non-ideality compensating calibration parameter containing matrices which represent sample system investigating system components and rotation matrices, each thereof being oriented in a series of said sample system investigating system component and rotation matrices to appropriately represent a "straight-through" or a "sample-present" configuration of said sample system investigating system;

d. performing a simultaneous mathematical regression of Step c., analytically arrived at effective non-ideality compensating calibration parameter containing equations for coefficients of two-dimensional mathematical coefficients, onto analogically equivalent numerical value for two-dimensional mathematical series coefficients as arrived at in Step b.;

such that non-ideality compensating calibration parameters in said effective non-ideality compensating calibration parameter containing equations for two-dimensional mathematical series coefficients are simultaneously evaluated, based upon an error reducing criteria.

20. A method of calibrating for nonidealities as in claim 19, wherein the step of performing a simultaneous mathematical regression such that each non-ideality compensating calibration parameter in each effective non-ideality compensating calibration parameter containing equation for coefficients of said two-dimensional mathematical series, involves a two-dimensional Fourier series.

21. A method of calibrating for nonidealities in mathematical representations of rotated and non-rotated components of a sample system investigating system, which sample system investigating system is sequentially comprised of a source of a beam of electromagnetic wavelengths, a polarizer means, a stage for supporting a sample system, an analyzer means and a detector system, which sample system investigating system is further comprised of at least a first compensator means, said at least a first compensator means being positioned in said sample system investigating system at a location selected from the group consisting of, before and after, said stage for supporting a sample system, and which sample system investigating system optionally comprises a second compensator means positioned in said sample system investigating system at a location complementary to said first compensator means, said position being selected from the group consisting of, respectively, after and before, said stage for supporting said sample system;

said method comprising the steps of:

a. empirically obtaining intensity value data sets measured by said detector system, said intensity value data sets being a function of wavelength and of settings of at least two of said sample system investigating system components, which sample system investigating system components are selected from the group consisting of said polarizer means, said analyzer means and present compensator means; at least one of which intensity value data sets is obtained with said sample system investigating system oriented in a "sample-present" configuration and at least one of which data sets is obtained with said sample system investigating system oriented in a configuration selected from the group consisting of "alternative sample-present" and "straight-through"; which "straight-through" configuration results from orienting said sample system investigating system such that a beam of electromagnetic wavelengths provided by said source of a beam of electromagnetic wavelengths is caused to pass through said polarization means, through said analyzer means and into said detector system; and which "sample-present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that in either of said "straight-through" or "sample-present" configurations of said sample system investigating system, said beam of electromagnetic wavelengths is also caused to pass through present compensator means;

b. effectively deriving analytical non-ideality compensating calibration parameter containing intensity equations for said sample system investigating system which correspond to said empirically obtained intensities, said effective analytically derived non-ideality compensating calibration parameter containing intensity equations being achievable by multiplying calibration parameter containing matrix representations of each sample system investigating system component, and rotation matrices, in a sample system investigating system representing sequence; and c. performing a simultaneous mathematical regression of empirically obtained intensity values onto effective analogically equivalent analytically derived calibration parameter containing equations obtained in steps a. and b;

such that non-ideality compensating calibration parameters in said non-ideality compensating calibration parameter containing effective analytically derived equations are simultaneously evaluated, based upon an error reducing criteria.

22. A method of calibrating for nonidealities as in claim 21, which further comprises, in conjunction with Step a., the obtaining of at least one additional intensity value data set measured by said detector system, which intensity values are a function of wavelength and of the settings of at least two of said sample system investigating system components in said sample system investigating system, which at least one additional data set is/are however, obtained from a sample system investigation system configuration selected from the group consisting of (wherein at least one of the sample system investigating system components originally present, is removed, and wherein an alternative sample system replaces the originally present sample system); the obtaining of said at least one additional intensity value data set being accompanied by the effective derivation of analytical non-ideality compensating calibration parameter containing equations corresponding to said at least one additional data set of intensity values; and including said additional empirically determined intensity values and analogically equivalent effective analytical derived non-ideality compensating calibration parameter containing equations in the simultaneous mathematical regression in Step c.

23. A method of calibrating for nonidealities as in claim 21, in which the procedure for achieving the setting of said at least one of said sample system investigating system components in said sample system investigating system is selected from the group consisting of, rotation of, tilting of, sliding of, application of an electrical field, and application of a magnetic field to a sample system investigating system component.

24. A method of calibrating for nonidealities in mathematical representations of rotated and non-rotated components of a sample system investigating system, which sample system investigating system is sequentially comprised of a source of a beam of electromagnetic wavelengths, a polarizer means, a stage for supporting a sample system, an analyzer means for selecting a state of polarization in said beam of electromagnetic wavelengths and a detector system, which sample system investigating system is further comprised of at least a first compensator means, said at least a first compensator means being positioned in said sample system investigating system at a location selected from the group consisting of, before and after, said stage for supporting a sample system, and which sample system investigating system optionally comprises a second compensator means positioned in said sample system investigating system at a location complementary to said first compensator means, said position being selected from the group consisting of, respectively, after and before, said stage for supporting said sample system; said at least first compensator means in said sample system investigation system being essentially achromatic and of a dual-rhomb construction such that a polarized beam of electromagnetic wavelengths caused to pass therethrough in use, experiences four internal reflections, each of which internal reflections causes a retardance between quadrature components of said polarized beam of electromagnetic wavelengths, selected from the group consisting of one-sixteenth and of three-sixteenths of a wavelength, but which at least first compensator means effects essentially no deviation in the direction of propagation of said beam of electromagnetic wavelengths caused to pass therethrough, even when said at least one compensator means is caused to rotate;

said method comprising the steps of:

a. empirically obtaining intensity value data sets measured by said detector system, said intensity value data sets being a function of wavelength and of rotated settings of azimuthal angles of at least two of said sample system investigating system components, which sample system investigating system components are selected from the group consisting of said polarizer means, said analyzer means and present compensator means; at least one of which intensity value data sets is obtained with said sample system investigating system oriented in a "sample-present" configuration and at least one of which data sets is obtained with said sample system investigating system oriented in a configuration selected from the group consisting of a "alternative sample-present" and a "straight-through" configuration; which "straight-through" configuration results from orienting said sample system investigating system such that a beam of electromagnetic wavelengths provided by said source of a beam of electromagnetic wavelengths is caused to pass through said polarization means, through said analyzer means and into said detector system; and which "sample-present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that in either of said "straight-through" or "sample present" configurations of said sample system investigating system, said beam of electromagnetic wavelengths is also caused to pass through present compensator means;

b. effectively deriving analytical non-ideality compensating calibration parameter containing intensity equations for said sample system investigating system which correspond to said empirically obtained intensities, said effective analytically derived non-ideality compensating calibration parameter containing intensity equations being achievable by multiplying calibration parameter containing matrix representations of each sample system investigating system component, and rotation matrices, in a sample system investigating system representing sequence; and c. performing a simultaneous mathematical regression of empirically obtained intensity values onto effective analogically equivalent analytically derived calibration parameter containing equations obtained in steps a. and b;

such that non-ideality compensating calibration parameters in said effective non-ideality compensating calibration parameter containing analytically derived equations are simultaneously evaluated, based upon an error reducing criteria.

25. A method of calibrating for nonidealities as in claim 24, which further comprises, in conjunction with Step a., the obtaining of at least one additional intensity value data set measured by said detector system, which intensity values are a function of wavelength and of the rotated settings of azimuthal angles of at least two of said sample system investigating system components in said sample system investigating system, which at least one additional data set is/are however, obtained from a sample system investigation system configuration selected from the group consisting of (wherein at least one of the sample system investigating system components originally present, is removed, and wherein an alternative sample system replaces the originally present sample system); the obtaining of said at least one additional intensity value data set being accompanied by the effective derivation of analytical non-ideality compensating calibration parameter containing equations corresponding to said at least one additional data set of intensity values; and including said additional empirically determined intensity values and analogically equivalent analytical derived non-ideality compensating calibration parameter containing equations in the simultaneous mathematical regression in Step c.

26. A method of calibrating for nonidealities in mathematical representations of rotated and nonrotated components of a sample system investigating system, which sample system investigating system is sequentially comprised of a source of a beam of electromagnetic wavelengths, a polarizer means, a stage for supporting a sample system, an analyzer means and a detector system, which sample system investigating system is further comprised of at least a first compensator means, said at least a first compensator means being positioned in said sample system investigating system at a location selected from the group consisting of, before and after, said stage for supporting a sample system, and which sample system investigating system optionally comprises a second compensator means positioned in said sample system investigating system at a location complementary to said first compensator means, said position being selected from the group consisting of, respectively, after and before, said stage for supporting said sample system; said method comprising the steps of:

a. empirically obtaining at least two data sets, each of which data sets consists of intensity values measured by said detector system, said intensity values being a function of wavelength and of rotated settings of azimuthal angles of said analyzer means and said polarizer means of said sample system investigating system; one of which data sets is obtained with said sample system investigating system oriented in a "sample-present" configuration such that in one case a compensator means is present and in the other case a present compensator means is not present; which "sample-present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that said beam of electromagnetic wavelengths is also caused to pass through any present compensator means;

b. effectively deriving analytical non-ideality compensating calibration parameter containing intensity equations for said sample system investigating system which correspond to said empirically obtained intensities, said effective analytically derived non-ideality compensating calibration parameter containing intensity equations being achievable by multiplying calibration parameter containing matrix representations of each sample system investigating system component, and rotation matrices, in a sample system investigating system representing sequence; and c. performing a simultaneous mathematical regression of empirically obtained intensity values onto effective analogically equivalent analytically derived calibration parameter containing equations obtained in steps a. and b;

such that non-ideality compensating calibration parameter in said effective non-ideality compensating calibration parameter containing equations are simultaneously evaluated, based upon an error reducing criteria.

27. A method of calibrating for nonidealities in mathematical representations of rotated and non-rotated components of a sample system investigating system, which sample system investigating system is sequentially comprised of a source of a beam of electromagnetic wavelengths, a polarizer means, a stage for supporting a sample system, an analyzer means and a detector system, which sample system investigating system is further comprised of at least a first compensator means, said at least a first compensator means being positioned in said sample system investigating system at a location selected from the group consisting of, before and after, said stage for supporting a sample system, and which sample system investigating system optionally comprises a second compensator means positioned in said sample system investigating system at a location complementary to said first compensator means, said position being selected from the group consisting of, respectively, after and before, said stage for supporting said sample system; said method comprising the steps of:

a. empirically obtaining at least three data sets, each of which data sets consists of intensity values measured by said detector system, said intensity values being a function of wavelength and of rotated settings of azimuthal angles of said analyzer means and said polarizer means of said sample system investigating system; one of which data sets is obtained with said sample system investigating system oriented in a configuration selected from the group consisting of a "sample-present" and a "straight-through" configuration; a second of which data sets is obtained with said sample system investigating system oriented in an "alternative sample-present" configuration; and a third of which data sets is obtained with said sample system investigating system oriented in a configuration selected from the group consisting of, (wherein a present compensator means is removed, and wherein an "alternative sample-system" is substituted for a previously present "sample-system"); which "straight-through" configuration results from orienting said sample system investigating system such that a beam of electromagnetic wavelengths provided by said source of a beam of electromagnetic wavelengths is caused to pass through said polarization means, through said analyzer means and into said detector system; and which "sample-present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that in either of said "straight-through" or "sample-present" configurations of said sample system investigating system, said beam of electromagnetic wavelengths is also caused to pass through any present compensator means;

b. effectively deriving analytical non-ideality compensating calibration parameter containing intensity equations for said sample system investigating system which correspond to said empirically obtained intensities, said effective analytically derived non-ideality compensating calibration parameter containing intensity equations being achievable by multiplying calibration parameter containing matrix representations of each sample system investigating system component, and rotation matrices, in a sample system investigating system representing sequence; and c. performing a simultaneous mathematical regression of empirically obtained intensity values onto effective analogically equivalent analytically derived calibration parameter containing equations obtained in steps a. and b;

such that non-ideality compensating calibration parameters in said effective non-ideality compensating calibration parameter containing equations are simultaneously evaluated, based upon an error reducing criteria.

28. A method of calibrating for nonidealities in mathematical representations of rotated and non-rotated components of a sample system investigating system, which sample system investigating system is sequentially comprised of a source of a beam of electromagnetic wavelengths, a polarizer means, a stage for supporting a sample system, an analyzer means and a detector system, which sample system investigating system is further comprised of at least a first compensator means, said at least a first compensator means being positioned in said sample system investigating system at a location selected from the group consisting of, before and after, said stage for supporting a sample system, and which sample system investigating system optionally comprises a second compensator means positioned in said sample system investigating system at a location complementary to said first compensator means, said position being selected from the group consisting of, respectively, after and before, said stage for supporting said sample system; said method comprising the steps of:

a. empirically obtaining at least two data sets, each of which data sets consists of intensity values measured-by said detector system, said intensity values being a function of wavelength and of rotated settings of azimuthal angles of a component selected from the group consisting of (said polarizer means and said analyzer means), and one said compensator means of said sample system investigating system; one of which data sets is obtained with said sample system investigating system oriented in a "sample-present" configuration, and one of which data is obtained with said sample system investigating system oriented in a configuration selected from the group consisting of "alternative sample-present" and "straight-through"; which "straight-through" configuration results from orienting said sample system investigating system such that a beam of electromagnetic wavelengths provided by said source of a beam of electromagnetic wavelengths is caused to pass through said polarization means, through said analyzer means and into said detector system; and which "sample-present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that in either of said "straight-through" or "sample-present" configurations of said sample system investigating system, said beam of electromagnetic wavelengths is also caused to pass through present compensator means;

b. effectively deriving analytical non-ideality compensating calibration parameter containing intensity equations for said sample system investigating system which correspond to said empirically obtained intensities, said effective analytically derived non-ideality compensating calibration parameter containing intensity equations being achievable by multiplying calibration parameter containing matrix representations of each sample system investigating system component, and rotation matrices, in a sample system investigating system representing sequence; and c. performing a simultaneous mathematical regression of empirically obtained intensity values onto effective analogically equivalent analytically derived calibration parameter containing equations obtained in steps a. and b;

such that non-ideality compensating calibration parameters in said effective non-ideality compensating calibration parameter containing equations are simultaneously evaluated, based upon an error reducing criteria.

29. A method of calibrating for nonidealities in mathematical representations of rotated and non-rotated components of a sample system investigating system, which sample system investigating system is sequentially comprised of a source of a beam of electromagnetic wavelengths, a polarizer means, a stage for supporting a sample system, an analyzer means and a detector system, which sample system investigating system is further comprised of a first compensator means, said first compensator means being positioned in said sample system investigating system at a location selected from the group consisting of, before and after, said stage for supporting a sample system, and which sample system investigating system further comprises a second compensator means positioned in said sample system investigating system at a location complementary to said first compensator means, said position being selected from the group consisting of, respectively, after and before, said stage for supporting said sample system; said method comprising the steps of:

a. empirically obtaining at least two data sets, each of which data sets consists of intensity values measured by said detector system, said intensity values being a function of wavelength and of rotated settings of azimuthal angles of said first compensator means and said second compensator means of said sample system investigating system; one of which data sets is obtained with said sample system investigating system oriented in a "sample-present" configuration, and one of which data is obtained with said sample system investigating system oriented in a configuration selected from the group consisting of "alternative sample-present" and "straight-through"; which "straight-through" configuration results from orienting said sample system investigating system such that a beam of electromagnetic wavelengths provided by said source of a beam of electromagnetic wavelengths is caused to pass through said polarization means, through said analyzer means and into said detector system; and which "sample-present" configuration results from orienting said sample system investigating system such that a beam of electromagnetic wavelengths provided by said source of a beam of electromagnetic wavelengths is caused to pass through said polarization means, interact with an arbitrary sample system supported by said stage for supporting a sample system, pass through said analyzer means and into said detector system; such that in either of said "straight-through" or "sample-present" configurations of said sample system investigating system, said beam of electromagnetic wavelengths is also caused to pass through present first and second compensator means;

b. effectively deriving analytical non-ideality compensating calibration parameter containing intensity equations for said sample system investigating system which correspond to said empirically obtained intensities, said effective analytically derived non-ideality compensating calibration parameter containing intensity equations being achievable by multiplying calibration parameter containing matrix representations of each sample system investigating system component, and rotation matrices, in a sample system investigating system representing sequence; and c. performing a simultaneous mathematical regression of empirically obtained intensity values onto effective analogically equivalent analytically derived calibration parameter containing equations obtained in steps a. and b;

such that non-ideality compensating calibration parameters in said effective non-ideality compensating calibration parameter containing equations are simultaneously evaluated, based upon an error reducing criteria.

* * * * *